United States Patent [19]
Leppla et al.

[11] Patent Number: 5,677,274
[45] Date of Patent: Oct. 14, 1997

[54] ANTHRAX TOXIN FUSION PROTEINS AND RELATED METHODS

[75] Inventors: Stephen H. Leppla, Bethesda; Kurt R. Klimpel, Gaithersburg, both of Md.; Naveen Arora; Yogendra Singh, both of Delhi, India; Peter J. Nichols, Welling Kent, United Kingdom

[73] Assignee: The Government of the United States as represented by the Secretary of the Department of Health and Human Services, Washington, D.C.

[21] Appl. No.: 82,849

[22] Filed: Jun. 25, 1993

Related U.S. Application Data

[63] Continuation-in-part of Ser. No. 21,601, Feb. 12, 1993, Pat. No. 5,591,631.

[51] Int. Cl.$^6$ .................................................... A61K 39/00
[52] U.S. Cl. .................................................................. 514/2
[58] Field of Search ................................ 514/2; 424/1.69

[56] References Cited

PUBLICATIONS

Klimpel et al, "Modified Anthrax Toxin is Cleaved . . . by HIV-1 Protease" *J. Cell. Biochem*, Suppl. 18B:163, abstract J515 (Jan. 1994).
Friedlander, "Macrophages are Sensitive to Anthrax Lethal Toxin . . ." *J. Biol. Chem.* 261(16):7123–7126 (Jun. 1986).
Arora et al., *J. Bio. Chem.*, 267(22):15542–15548 (1992).
Arora et al. Abstract: *Third Internatl. Sympos. on Immunotoxins*, Orlando, FL (Jun. 19–21, 1992).
Quinn et al., *J. Bio. Chem.*, 266(30):20124–20130 (1991).
Oeltmann and Frankel, *News*, 5:2334–2337 (Jul. 1991).
Singh et al., *J. Bio. Chem.*, 266(23):15493–15497 (1991).
Singh et al., *J. Bio. Chem.*, 264(32):19103–19107 (1989).
Leppla et al. Abstract: *Fifth European Workshop on Bacterial Protein Toxins*, Veldhoven (Jun. 30–Jul. 5, 1991).
Klimpel et al. Abstract: *1992 ASM General Meeting*, New Orleans, LA (May 1992).
Novak, J.M., et al., "Functional Characterization of Protease–treated *Bacillus anthracis* Protective Antigen," *J. of Biological Chemistry*, 267(24):17186–17193 (Aug. 25, 1992).
Ivins, B.E., et al., "Cloning and Expression of the *Bacillus anthracis* Protective Antigen Gene in *Bacillus subtilis*," *Infection and Immunity*, 54(2):537–542 (Nov. 1986).
Molloy, S.S., et al, "Human Furin is a Calcium–dependent Serine Endoprotease That Recognizes the Sequence Arg–X–X–Arg and Efficiently Cleaves Anthrax Toxin Protective Antigen," *J. of Biological Chemistry*, 267(23):16396–16402 (Aug. 15, 1992).
Zhang, L., et al., "Inhibition of HIV-1 RNA Production by the Diphtheria Toxin–Related IL-2 Fusion Proteins $DAB_{486}IL$-2 and $DAB_{389}IL$-2," *J. of Acquired Immune Deficiency Syndromes*, 5(12):1181–1187 (1992).
O'Hare, M., et al., "Cytotoxicity of a recombinant ricin--A–chain fusion protein containing a proteolytically–cleavable spacer sequence," *FEBS Lett.* 273(1,2):200–204 (Oct. 1990).
Williams, D.P., et al., "Cellular Processing of the Interleukin–2 Fusion Toxin $DAB_{486}$–IL–2 and Efficient Delivery of Diphtheria Fragment A to the Cytosol of Target Cells Requires $Arg^{194}$," *J. of Biological Chemistry*, 265(33):20673–20677 (Nov. 25, 1990).
Ohishi, I., et al., "Visualizations of Binding and Internalization of Two Nonlinked Protein Components of Botulinum $C_2$ Toxin in Tissue Culture Cells," *Infection and Immunity*, 60(11):4648–4655 (Nov. 1992).
Arora, Navene., et al. (1992) "Potent hybrid cytotoxins of anthrax lethal factor and the ADP–ribosylation domain of *Pseudomonas exotoxin* A are translocated direct to the cytosol of mammalian cells", *Abstracts of the General Meeting of the American Society for Microbiology*, abstract n. B–33.
Cataldi, Angel, et al. (1992) "Regulation of pag gene expression in *Bacillus anthracis*: Use of a pag–lacZ transcriptional fusion", *FEMS Microbiology Letters*, 98(1–3):89–94.
Klimpel, Kurt R., et al. (1992) "Anthrax toxin protective antigen is activated by a cell surface protease with the sequence specificity and catalytic properties of furin", *Proceedings of the National Academy of Sciences of USA*, 89(21):10277–10281.
Arora, Navene, et al. (1993) "Residues 1–254 of anthrax toxin lethal factor are sufficient to cause cellular uptake of fused polypeptides", *Journal of Biological Chemistry*, 268(5):3334–3341.

*Primary Examiner*—Vasu S. Jagannathan
*Assistant Examiner*—David S. Romeo
*Attorney, Agent, or Firm*—Townsend and Townsend and Crew

[57] ABSTRACT

The present invention provides a nucleic acid encoding a fusion protein comprising a nucleotide sequence encoding the anthrax protective antigen (PA) binding domain of the native anthrax lethal factor (LF) protein and a nucleotide sequence encoding an activity inducing domain of a second protein. Also provided is a nucleic acid encoding a fusion protein comprising a nucleotide sequence encoding the translocation domain and LF binding domain of the native anthrax PA protein and a nucleotide sequence encoding a ligand domain which specifically binds a cellular target. Proteins encoded by the nucleic acid of the invention, vectors comprising the nucleic acids and hosts capable of expressing the protein encoded by the nucleic acids are also provided. A composition comprising the PA binding domain of the native LF protein chemically attached to a non-LF activity inducing moiety is further provided. A method for delivering an activity to a cell is provided. The steps of the method include a) administering to the cell a protein comprising the translocation domain and the LF binding domain of the native PA protein and a ligand domain, and b) administering to the cell a product comprising the PA binding domain of the native LF protein and a non-LF activity inducing moiety, whereby the product administered in step b) is internalized into the cell and performs the activity within the cell. The invention also provides proteins including an anthrax protective antigen which has been mutated to replace the trypsin cleavage site with residues recognized specifically by the HIV-1 protease.

12 Claims, 1 Drawing Sheet

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 3291 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus anthracis ( i x ) FEATURE:
  ( A ) NAME/KEY: CDS
  ( B ) LOCATION: 580..2907
  ( D ) OTHER INFORMATION: /product="Lethal Factor"

( x i ) SEQUENCE DESCRIPTION: SEQ ID NO:1:

| | | |
|---|---|---|
| AAATTAGGAT TTCGGTTATG TTTAGTATTT TTTTAAAATA ATAGTATTAA ATAGTGGAAT | 60 |
| GCAAATGATA AATGGGCTTT AAACAAAACT AATGAAATAA TCTACAAATG GAATTTCTCC | 120 |
| AGTTTTAGAT TAAACCATAC CAAAAAAATC ACACTGTCAA GAAAAATGAT AGAATCCCTA | 180 |
| CACTAATTAA CATAACCAAA TTGGTAGTTA TAGGTAGAAA CTTATTTATT TCTATAATAC | 240 |
| CATGCAAAAA AGTAAATATT CTGTTCCATA CTATTTTAGT AAATTATTTA GCAAGTAAAT | 300 |
| TTTGGTGTAT AAACAAAGTT TATCTTAATA TAAAAAATTA CTTTACTTTT ATACAGATTA | 360 |
| AAATGAAAAA TTTTTTATGA CAAGAAATAT TGCCTTTAAT TTATGAGGAA ATAAGTAAAA | 420 |
| TTTTCTACAT ACTTTATTTT ATTGTTGAAA TGTTCACTTA TAAAAAAGGA GAGATTAAAT | 480 |
| ATGAATATAA AAAAAGAATT TATAAAAGTA ATTAGTATGT CATGTTTAGT AACAGCAATT | 540 |
| ACTTTGAGTG GTCCCGTCTT TATCCCCCTT GTACAGGGG GCG GGC GGT CAT GGT | 594 |
|  | Ala Gly Gly His Gly |
|  | 1   5 |

| | | |
|---|---|---|
| GAT GTA GGT ATG CAC GTA AAA GAG AAA GAG AAA AAT AAA GAT GAG AAT | 642 |
| Asp Val Gly Met His Val Lys Glu Lys Glu Lys Asn Lys Asp Glu Asn |
|     10              15              20 |

| | | |
|---|---|---|
| AAG AGA AAA GAT GAA GAA CGA AAT AAA ACA CAG GAA GAG CAT TTA AAG | 690 |
| Lys Arg Lys Asp Glu Glu Arg Asn Lys Thr Gln Glu Glu His Leu Lys |
|     25              30              35 |

| | | |
|---|---|---|
| GAA ATC ATG AAA CAC ATT GTA AAA ATA GAA GTA AAA GGG GAG GAA GCT | 738 |
| Glu Ile Met Lys His Ile Val Lys Ile Glu Val Lys Gly Glu Glu Ala |
|         40              45              50 |

| | | |
|---|---|---|
| GTT AAA AAA GAG GCA GCA GAA AAG CTA CTT GAG AAA GTA CCA TCT GAT | 786 |
| Val Lys Lys Glu Ala Ala Glu Lys Leu Leu Glu Lys Val Pro Ser Asp |
|     55              60              65 |

| | | |
|---|---|---|
| GTT TTA GAG ATG TAT AAA GCA ATT GGA GGA AAG ATA TAT ATT GTG GAT | 834 |
| Val Leu Glu Met Tyr Lys Ala Ile Gly Gly Lys Ile Tyr Ile Val Asp |
| 70              75              80              85 |

| | | |
|---|---|---|
| GGT GAT ATT ACA AAA CAT ATA TCT TTA GAA GCA TTA TCT GAA GAT AAG | 882 |
| Gly Asp Ile Thr Lys His Ile Ser Leu Glu Ala Leu Ser Glu Asp Lys |
|             90              95             100 |

| | | |
|---|---|---|
| AAA AAA ATA AAA GAC ATT TAT GGG AAA GAT GCT TTA TTA CAT GAA CAT | 930 |
| Lys Lys Ile Lys Asp Ile Tyr Gly Lys Asp Ala Leu Leu His Glu His |
|         105             110             115 |

| | | |
|---|---|---|
| TAT GTA TAT GCA AAA GAA GGA TAT GAA CCC GTA CTT GTA ATC CAA TCT | 978 |
| Tyr Val Tyr Ala Lys Glu Gly Tyr Glu Pro Val Leu Val Ile Gln Ser |
|     120             125             130 |

| | | |
|---|---|---|
| TCG GAA GAT TAT GTA GAA AAT ACT GAA AAG GCA CTG AAC GTT TAT TAT | 1026 |
| Ser Glu Asp Tyr Val Glu Asn Thr Glu Lys Ala Leu Asn Val Tyr Tyr |
| 135             140             145 |

| | | |
|---|---|---|
| GAA ATA GGT AAG ATA TTA TCA AGG GAT ATT TTA AGT AAA ATT AAT CAA | 1074 |
| Glu Ile Gly Lys Ile Leu Ser Arg Asp Ile Leu Ser Lys Ile Asn Gln |
| 150             155             160             165 |

| | | |
|---|---|---|
| CCA TAT CAG AAA TTT TTA GAT GTA TTA AAT ACC ATT AAA AAT GCA TCT | 1122 |
| Pro Tyr Gln Lys Phe Leu Asp Val Leu Asn Thr Ile Lys Asn Ala Ser |
|             170             175             180 |

| | | |
|---|---|---|
| GAT TCA GAT GGA CAA GAT CTT TTA TTT ACT AAT CAG CTT AAG GAA CAT | 1170 |
| Asp Ser Asp Gly Gln Asp Leu Leu Phe Thr Asn Gln Leu Lys Glu His |
|         185             190             195 |

| | | |
|---|---|---|
| CCC ACA GAC TTT TCT GTA GAA TTC TTG GAA CAA AAT AGC AAT GAG GTA | 1218 |
| Pro Thr Asp Phe Ser Val Glu Phe Leu Glu Gln Asn Ser Asn Glu Val |

-continued

|  |  |  | 200 |  |  |  |  | 205 |  |  |  |  | 210 |  |  |  |
|---|---|---|---|---|---|---|---|---|---|---|---|---|---|---|---|---|
| CAA | GAA | GTA | TTT | GCG | AAA | GCT | TTT | GCA | TAT | TAT | ATC | GAG | CCA | CAG | CAT | 1266 |
| Gln | Glu | Val | Phe | Ala | Lys | Ala | Phe | Ala | Tyr | Tyr | Ile | Glu | Pro | Gln | His |  |
| 215 |  |  |  |  | 220 |  |  |  |  | 225 |  |  |  |  |  |  |
| CGT | GAT | GTT | TTA | CAG | CTT | TAT | GCA | CCG | GAA | GCT | TTT | AAT | TAC | ATG | GAT | 1314 |
| Arg | Asp | Val | Leu | Gln | Leu | Tyr | Ala | Pro | Glu | Ala | Phe | Asn | Tyr | Met | Asp |  |
| 230 |  |  |  |  | 235 |  |  |  |  | 240 |  |  |  |  | 245 |  |
| AAA | TTT | AAC | GAA | CAA | GAA | ATA | AAT | CTA | TCC | TTG | GAA | GAA | CTT | AAA | GAT | 1362 |
| Lys | Phe | Asn | Glu | Gln | Glu | Ile | Asn | Leu | Ser | Leu | Glu | Glu | Leu | Lys | Asp |  |
|  |  |  |  | 250 |  |  |  |  | 255 |  |  |  |  | 260 |  |  |
| CAA | CGG | ATG | CTG | TCA | AGA | TAT | GAA | AAA | TGG | GAA | AAG | ATA | AAA | CAG | CAC | 1410 |
| Gln | Arg | Met | Leu | Ser | Arg | Tyr | Glu | Lys | Trp | Glu | Lys | Ile | Lys | Gln | His |  |
|  |  |  | 265 |  |  |  |  | 270 |  |  |  |  | 275 |  |  |  |
| TAT | CAA | CAC | TGG | AGC | GAT | TCT | TTA | TCT | GAA | GAA | GGA | AGA | GGA | CTT | TTA | 1458 |
| Tyr | Gln | His | Trp | Ser | Asp | Ser | Leu | Ser | Glu | Glu | Gly | Arg | Gly | Leu | Leu |  |
|  |  | 280 |  |  |  |  | 285 |  |  |  |  | 290 |  |  |  |  |
| AAA | AAG | CTG | CAG | ATT | CCT | ATT | GAG | CCA | AAG | AAA | GAT | GAC | ATA | ATT | CAT | 1506 |
| Lys | Lys | Leu | Gln | Ile | Pro | Ile | Glu | Pro | Lys | Lys | Asp | Asp | Ile | Ile | His |  |
| 295 |  |  |  |  | 300 |  |  |  |  | 305 |  |  |  |  |  |  |
| TCT | TTA | TCT | CAA | GAA | GAA | AAA | GAG | CTT | CTA | AAA | AGA | ATA | CAA | ATT | GAT | 1554 |
| Ser | Leu | Ser | Gln | Glu | Glu | Lys | Glu | Leu | Leu | Lys | Arg | Ile | Gln | Ile | Asp |  |
| 310 |  |  |  |  | 315 |  |  |  |  | 320 |  |  |  |  | 325 |  |
| AGT | AGT | GAT | TTT | TTA | TCT | ACT | GAG | GAA | AAA | GAG | TTT | TTA | AAA | AAG | CTA | 1602 |
| Ser | Ser | Asp | Phe | Leu | Ser | Thr | Glu | Glu | Lys | Glu | Phe | Leu | Lys | Lys | Leu |  |
|  |  |  |  | 330 |  |  |  |  | 335 |  |  |  |  | 340 |  |  |
| CAA | ATT | GAT | ATT | CGT | GAT | TCT | TTA | TCT | GAA | GAA | GAA | AAA | GAG | CTT | TTA | 1650 |
| Gln | Ile | Asp | Ile | Arg | Asp | Ser | Leu | Ser | Glu | Glu | Glu | Lys | Glu | Leu | Leu |  |
|  |  |  | 345 |  |  |  |  | 350 |  |  |  |  | 355 |  |  |  |
| AAT | AGA | ATA | CAG | GTG | GAT | AGT | AGT | AAT | CCT | TTA | TCT | GAA | AAA | GAA | AAA | 1698 |
| Asn | Arg | Ile | Gln | Val | Asp | Ser | Ser | Asn | Pro | Leu | Ser | Glu | Lys | Glu | Lys |  |
|  |  | 360 |  |  |  |  | 365 |  |  |  |  | 370 |  |  |  |  |
| GAG | TTT | TTA | AAA | AAG | CTG | AAA | CTT | GAT | ATT | CAA | CCA | TAT | GAT | ATT | AAT | 1746 |
| Glu | Phe | Leu | Lys | Lys | Leu | Lys | Leu | Asp | Ile | Gln | Pro | Tyr | Asp | Ile | Asn |  |
| 375 |  |  |  |  | 380 |  |  |  |  | 385 |  |  |  |  |  |  |
| CAA | AGG | TTG | CAA | GAT | ACA | GGA | GGG | TTA | ATT | GAT | AGT | CCG | TCA | ATT | AAT | 1794 |
| Gln | Arg | Leu | Gln | Asp | Thr | Gly | Gly | Leu | Ile | Asp | Ser | Pro | Ser | Ile | Asn |  |
| 390 |  |  |  |  | 395 |  |  |  |  | 400 |  |  |  |  | 405 |  |
| CTT | GAT | GTA | AGA | AAG | CAG | TAT | AAA | AGG | GAT | ATT | CAA | AAT | ATT | GAT | GCT | 1842 |
| Leu | Asp | Val | Arg | Lys | Gln | Tyr | Lys | Arg | Asp | Ile | Gln | Asn | Ile | Asp | Ala |  |
|  |  |  |  | 410 |  |  |  |  | 415 |  |  |  |  | 420 |  |  |
| TTA | TTA | CAT | CAA | TCC | ATT | GGA | AGT | ACC | TTG | TAC | AAT | AAA | ATT | TAT | TTG | 1890 |
| Leu | Leu | His | Gln | Ser | Ile | Gly | Ser | Thr | Leu | Tyr | Asn | Lys | Ile | Tyr | Leu |  |
|  |  |  | 425 |  |  |  |  | 430 |  |  |  |  | 435 |  |  |  |
| TAT | GAA | AAT | ATG | AAT | ATC | AAT | AAC | CTT | ACA | GCA | ACC | CTA | GGT | GCG | GAT | 1938 |
| Tyr | Glu | Asn | Met | Asn | Ile | Asn | Asn | Leu | Thr | Ala | Thr | Leu | Gly | Ala | Asp |  |
|  |  | 440 |  |  |  |  | 445 |  |  |  |  | 450 |  |  |  |  |
| TTA | GTT | GAT | TCC | ACT | GAT | AAT | ACT | AAA | ATT | AAT | AGA | GGT | ATT | TTC | AAT | 1986 |
| Leu | Val | Asp | Ser | Thr | Asp | Asn | Thr | Lys | Ile | Asn | Arg | Gly | Ile | Phe | Asn |  |
| 455 |  |  |  |  | 460 |  |  |  |  | 465 |  |  |  |  |  |  |
| GAA | TTC | AAA | AAA | AAT | TTC | AAA | TAT | AGT | ATT | TCT | AGT | AAC | TAT | ATG | ATT | 2034 |
| Glu | Phe | Lys | Lys | Asn | Phe | Lys | Tyr | Ser | Ile | Ser | Ser | Asn | Tyr | Met | Ile |  |
| 470 |  |  |  |  | 475 |  |  |  |  | 480 |  |  |  |  | 485 |  |
| GTT | GAT | ATA | AAT | GAA | AGG | CCT | GCA | TTA | GAT | AAT | GAG | CGT | TTG | AAA | TGG | 2082 |
| Val | Asp | Ile | Asn | Glu | Arg | Pro | Ala | Leu | Asp | Asn | Glu | Arg | Leu | Lys | Trp |  |
|  |  |  |  | 490 |  |  |  |  | 495 |  |  |  |  | 500 |  |  |
| AGA | ATC | CAA | TTA | TCA | CCA | GAT | ACT | CGA | GCA | GGA | TAT | TTA | GAA | AAT | GGA | 2130 |
| Arg | Ile | Gln | Leu | Ser | Pro | Asp | Thr | Arg | Ala | Gly | Tyr | Leu | Glu | Asn | Gly |  |
|  |  |  | 505 |  |  |  |  | 510 |  |  |  |  | 515 |  |  |  |
| AAG | CTT | ATA | TTA | CAA | AGA | AAC | ATC | GGT | CTG | GAA | ATA | AAG | GAT | GTA | CAA | 2178 |
| Lys | Leu | Ile | Leu | Gln | Arg | Asn | Ile | Gly | Leu | Glu | Ile | Lys | Asp | Val | Gln |  |

```
                520                           525                           530
ATA ATT AAG CAA TCC GAA AAA GAA TAT ATA AGG ATT GAT GCG AAA GTA              2226
Ile Ile Lys Gln Ser Glu Lys Glu Tyr Ile Arg Ile Asp Ala Lys Val
    535                           540                           545

GTG CCA AAG AGT AAA ATA GAT ACA AAA ATT CAA GAA GCA CAG TTA AAT              2274
Val Pro Lys Ser Lys Ile Asp Thr Lys Ile Gln Glu Ala Gln Leu Asn
550                           555                           560                565

ATA AAT CAG GAA TGG AAT AAA GCA TTA GGG TTA CCA AAA TAT ACA AAG              2322
Ile Asn Gln Glu Trp Asn Lys Ala Leu Gly Leu Pro Lys Tyr Thr Lys
                    570                           575                       580

CTT ATT ACA TTC AAC GTG CAT AAT AGA TAT GCA TCC AAT ATT GTA GAA              2370
Leu Ile Thr Phe Asn Val His Asn Arg Tyr Ala Ser Asn Ile Val Glu
                585                           590                       595

AGT GCT TAT TTA ATA TTG AAT GAA TGG AAA AAT AAT ATT CAA AGT GAT              2418
Ser Ala Tyr Leu Ile Leu Asn Glu Trp Lys Asn Asn Ile Gln Ser Asp
            600                           605                       610

CTT ATA AAA AAG GTA ACA AAT TAC TTA GTT GAT GGT AAT GGA AGA TTT              2466
Leu Ile Lys Lys Val Thr Asn Tyr Leu Val Asp Gly Asn Gly Arg Phe
        615                           620                       625

GTT TTT ACC GAT ATT ACT CTC CCT AAT ATA GCT GAA CAA TAT ACA CAT              2514
Val Phe Thr Asp Ile Thr Leu Pro Asn Ile Ala Glu Gln Tyr Thr His
630                           635                       640                   645

CAA GAT GAG ATA TAT GAG CAA GTT CAT TCA AAA GGG TTA TAT GTT CCA              2562
Gln Asp Glu Ile Tyr Glu Gln Val His Ser Lys Gly Leu Tyr Val Pro
                    650                       655                       660

GAA TCC CGT TCT ATA TTA CTC CAT GGA CCT TCA AAA GGT GTA GAA TTA              2610
Glu Ser Arg Ser Ile Leu Leu His Gly Pro Ser Lys Gly Val Glu Leu
                665                       670                       675

AGG AAT GAT AGT GAG GGT TTT ATA CAC GAA TTT GGA CAT GCT GTG GAT              2658
Arg Asn Asp Ser Glu Gly Phe Ile His Glu Phe Gly His Ala Val Asp
            680                       685                       690

GAT TAT GCT GGA TAT CTA TTA GAT AAG AAC CAA TCT GAT TTA GTT ACA              2706
Asp Tyr Ala Gly Tyr Leu Leu Asp Lys Asn Gln Ser Asp Leu Val Thr
        695                       700                       705

AAT TCT AAA AAA TTC ATT GAT ATT TTT AAG GAA GAA GGG AGT AAT TTA              2754
Asn Ser Lys Lys Phe Ile Asp Ile Phe Lys Glu Glu Gly Ser Asn Leu
710                       715                       720                       725

ACT TCG TAT GGG AGA ACA AAT GAA GCG GAA TTT TTT GCA GAA GCC TTT              2802
Thr Ser Tyr Gly Arg Thr Asn Glu Ala Glu Phe Phe Ala Glu Ala Phe
                    730                       735                       740

AGG TTA ATG CAT TCT ACG GAC CAT GCT GAA CGT TTA AAA GTT CAA AAA              2850
Arg Leu Met His Ser Thr Asp His Ala Glu Arg Leu Lys Val Gln Lys
                745                       750                       755

AAT GCT CCG AAA ACT TTC CAA TTT ATT AAC GAT CAG ATT AAG TTC ATT              2898
Asn Ala Pro Lys Thr Phe Gln Phe Ile Asn Asp Gln Ile Lys Phe Ile
            760                       765                       770

ATT AAC TCA TAAGTAATGT ATTAAAAATT TTCAAATGGA TTTAATAATA                      2947
Ile Asn Ser
775

ATAATAATAA TAATAATAAC GGGACCAGCC ATTATGAAGC AACTAATTCT AGACTTGATA            3007
GTAATTCTTG GGAAGCACCA GATAGTGTAA AAGGTGGCAT TGCCAGAATG ATATTTTATG            3067
TGTTCGTTAG ATATGAAGGC AAAAACAATG ATCCTGACCT AGAACTTAAT GATAATGTTA            3127
TTAATAATTT AATGCCTTTT ATAGGAATAT TAGTAAAAGT GCCGAAAAGA TCCTGTTGCA            3187
AAGCTTTTAA AGAACATATT ATTCTATCAA GTGGCTGTAT ATTTTGTGTA ATTTTCAATA            3247
AATTTTGTAA TTAAGCATAC GTCAAAAAAC CGAAATCTGA GCTC                             3291
```

( 2 ) INFORMATION FOR SEQ ID NO:2:

(i) SEQUENCE CHARACTERISTICS:
   (A) LENGTH: 776 amino acids
   (B) TYPE: amino acid
   (D) TOPOLOGY: linear (ii) MOLECULE TYPE: protein (xi) SEQUENCE DESCRIPTION: SEQ ID NO:2:

| Ala | Gly | Gly | His | Gly | Asp | Val | Gly | Met | His | Val | Lys | Glu | Lys | Glu | Lys |
|---|---|---|---|---|---|---|---|---|---|---|---|---|---|---|---|
| 1 | | | | 5 | | | | | 10 | | | | | 15 | |

| Asn | Lys | Asp | Glu | Asn | Lys | Arg | Lys | Asp | Glu | Glu | Arg | Asn | Lys | Thr | Gln |
|---|---|---|---|---|---|---|---|---|---|---|---|---|---|---|---|
| | | | 20 | | | | | 25 | | | | | 30 | | |

| Glu | Glu | His | Leu | Lys | Glu | Ile | Met | Lys | His | Ile | Val | Lys | Ile | Glu | Val |
|---|---|---|---|---|---|---|---|---|---|---|---|---|---|---|---|
| | | | 35 | | | | 40 | | | | | 45 | | | |

| Lys | Gly | Glu | Glu | Ala | Val | Lys | Glu | Ala | Ala | Glu | Lys | Leu | Leu | Glu |
|---|---|---|---|---|---|---|---|---|---|---|---|---|---|---|
| | 50 | | | | | 55 | | | | | 60 | | | |

| Lys | Val | Pro | Ser | Asp | Val | Leu | Glu | Met | Tyr | Lys | Ala | Ile | Gly | Gly | Lys |
|---|---|---|---|---|---|---|---|---|---|---|---|---|---|---|---|
| 65 | | | | | 70 | | | | | 75 | | | | | 80 |

| Ile | Tyr | Ile | Val | Asp | Gly | Asp | Ile | Thr | Lys | His | Ile | Ser | Leu | Glu | Ala |
|---|---|---|---|---|---|---|---|---|---|---|---|---|---|---|---|
| | | | | 85 | | | | | 90 | | | | | 95 | |

| Leu | Ser | Glu | Asp | Lys | Lys | Lys | Ile | Lys | Asp | Ile | Tyr | Gly | Lys | Asp | Ala |
|---|---|---|---|---|---|---|---|---|---|---|---|---|---|---|---|
| | | | | 100 | | | | | 105 | | | | | 110 | |

| Leu | Leu | His | Glu | His | Tyr | Val | Tyr | Ala | Lys | Glu | Gly | Tyr | Glu | Pro | Val |
|---|---|---|---|---|---|---|---|---|---|---|---|---|---|---|---|
| | | | 115 | | | | | 120 | | | | | 125 | | |

| Leu | Val | Ile | Gln | Ser | Ser | Glu | Asp | Tyr | Val | Glu | Asn | Thr | Glu | Lys | Ala |
|---|---|---|---|---|---|---|---|---|---|---|---|---|---|---|---|
| | | 130 | | | | | 135 | | | | | 140 | | | |

| Leu | Asn | Val | Tyr | Tyr | Glu | Ile | Gly | Lys | Ile | Leu | Ser | Arg | Asp | Ile | Leu |
|---|---|---|---|---|---|---|---|---|---|---|---|---|---|---|---|
| 145 | | | | | 150 | | | | | 155 | | | | | 160 |

| Ser | Lys | Ile | Asn | Gln | Pro | Tyr | Gln | Lys | Phe | Leu | Asp | Val | Leu | Asn | Thr |
|---|---|---|---|---|---|---|---|---|---|---|---|---|---|---|---|
| | | | | 165 | | | | | 170 | | | | | 175 | |

| Ile | Lys | Asn | Ala | Ser | Asp | Ser | Asp | Gly | Gln | Asp | Leu | Leu | Phe | Thr | Asn |
|---|---|---|---|---|---|---|---|---|---|---|---|---|---|---|---|
| | | | 180 | | | | | 185 | | | | | 190 | | |

| Gln | Leu | Lys | Glu | His | Pro | Thr | Asp | Phe | Ser | Val | Glu | Phe | Leu | Glu | Gln |
|---|---|---|---|---|---|---|---|---|---|---|---|---|---|---|---|
| | | | 195 | | | | 200 | | | | | 205 | | | |

| Asn | Ser | Asn | Glu | Val | Gln | Glu | Val | Phe | Ala | Lys | Ala | Phe | Ala | Tyr | Tyr |
|---|---|---|---|---|---|---|---|---|---|---|---|---|---|---|---|
| | 210 | | | | | 215 | | | | | 220 | | | | |

| Ile | Glu | Pro | Gln | His | Arg | Asp | Val | Leu | Gln | Leu | Tyr | Ala | Pro | Glu | Ala |
|---|---|---|---|---|---|---|---|---|---|---|---|---|---|---|---|
| 225 | | | | | 230 | | | | | 235 | | | | | 240 |

| Phe | Asn | Tyr | Met | Asp | Lys | Phe | Asn | Glu | Gln | Glu | Ile | Asn | Leu | Ser | Leu |
|---|---|---|---|---|---|---|---|---|---|---|---|---|---|---|---|
| | | | | 245 | | | | | 250 | | | | | 255 | |

| Glu | Glu | Leu | Lys | Asp | Gln | Arg | Met | Leu | Ser | Arg | Tyr | Glu | Lys | Trp | Glu |
|---|---|---|---|---|---|---|---|---|---|---|---|---|---|---|---|
| | | | 260 | | | | | 265 | | | | | 270 | | |

| Lys | Ile | Lys | Gln | His | Tyr | Gln | His | Trp | Ser | Asp | Ser | Leu | Ser | Glu | Glu |
|---|---|---|---|---|---|---|---|---|---|---|---|---|---|---|---|
| | | 275 | | | | | 280 | | | | | 285 | | | |

| Gly | Arg | Gly | Leu | Leu | Lys | Lys | Leu | Gln | Ile | Pro | Ile | Glu | Pro | Lys | Lys |
|---|---|---|---|---|---|---|---|---|---|---|---|---|---|---|---|
| | 290 | | | | | 295 | | | | | 300 | | | | |

| Asp | Asp | Ile | Ile | His | Ser | Leu | Ser | Gln | Glu | Glu | Lys | Glu | Leu | Leu | Lys |
|---|---|---|---|---|---|---|---|---|---|---|---|---|---|---|---|
| 305 | | | | | 310 | | | | | 315 | | | | | 320 |

| Arg | Ile | Gln | Ile | Asp | Ser | Ser | Asp | Phe | Leu | Ser | Thr | Glu | Glu | Lys | Glu |
|---|---|---|---|---|---|---|---|---|---|---|---|---|---|---|---|
| | | | | 325 | | | | | 330 | | | | | 335 | |

| Phe | Leu | Lys | Lys | Leu | Gln | Ile | Asp | Ile | Arg | Asp | Ser | Leu | Ser | Glu | Glu |
|---|---|---|---|---|---|---|---|---|---|---|---|---|---|---|---|
| | | | 340 | | | | | 345 | | | | | 350 | | |

| Glu | Lys | Glu | Leu | Leu | Asn | Arg | Ile | Gln | Val | Asp | Ser | Ser | Asn | Pro | Leu |
|---|---|---|---|---|---|---|---|---|---|---|---|---|---|---|---|
| | | 355 | | | | | 360 | | | | | 365 | | | |

| Ser | Glu | Lys | Glu | Lys | Glu | Phe | Leu | Lys | Lys | Leu | Lys | Leu | Asp | Ile | Gln |

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 370 |     |     |     |     | 375 |     |     |     |     | 380 |
| Pro | Tyr | Asp | Ile | Asn | Gln | Arg | Leu | Gln | Asp | Thr | Gly | Gly | Leu | Ile | Asp |
| 385 |     |     |     |     | 390 |     |     |     |     | 395 |     |     |     |     | 400 |
| Ser | Pro | Ser | Ile | Asn | Leu | Asp | Val | Arg | Lys | Gln | Tyr | Lys | Arg | Asp | Ile |
|     |     |     |     | 405 |     |     |     |     | 410 |     |     |     |     | 415 |     |
| Gln | Asn | Ile | Asp | Ala | Leu | Leu | His | Gln | Ser | Ile | Gly | Ser | Thr | Leu | Tyr |
|     |     |     | 420 |     |     |     |     | 425 |     |     |     |     | 430 |     |     |
| Asn | Lys | Ile | Tyr | Leu | Tyr | Glu | Asn | Met | Asn | Ile | Asn | Asn | Leu | Thr | Ala |
|     |     | 435 |     |     |     |     | 440 |     |     |     |     | 445 |     |     |     |
| Thr | Leu | Gly | Ala | Asp | Leu | Val | Asp | Ser | Thr | Asp | Asn | Thr | Lys | Ile | Asn |
|     | 450 |     |     |     |     | 455 |     |     |     |     | 460 |     |     |     |     |
| Arg | Gly | Ile | Phe | Asn | Glu | Phe | Lys | Lys | Asn | Phe | Lys | Tyr | Ser | Ile | Ser |
| 465 |     |     |     |     | 470 |     |     |     |     | 475 |     |     |     |     | 480 |
| Ser | Asn | Tyr | Met | Ile | Val | Asp | Ile | Asn | Glu | Arg | Pro | Ala | Leu | Asp | Asn |
|     |     |     |     | 485 |     |     |     |     | 490 |     |     |     |     | 495 |     |
| Glu | Arg | Leu | Lys | Trp | Arg | Ile | Gln | Leu | Ser | Pro | Asp | Thr | Arg | Ala | Gly |
|     |     |     | 500 |     |     |     |     | 505 |     |     |     |     | 510 |     |     |
| Tyr | Leu | Glu | Asn | Gly | Lys | Leu | Ile | Leu | Gln | Arg | Asn | Ile | Gly | Leu | Glu |
|     |     | 515 |     |     |     |     | 520 |     |     |     |     | 525 |     |     |     |
| Ile | Lys | Asp | Val | Gln | Ile | Ile | Lys | Gln | Ser | Glu | Lys | Glu | Tyr | Ile | Arg |
|     | 530 |     |     |     |     | 535 |     |     |     |     | 540 |     |     |     |     |
| Ile | Asp | Ala | Lys | Val | Val | Pro | Lys | Ser | Lys | Ile | Asp | Thr | Lys | Ile | Gln |
| 545 |     |     |     |     | 550 |     |     |     |     | 555 |     |     |     |     | 560 |
| Glu | Ala | Gln | Leu | Asn | Ile | Asn | Gln | Glu | Trp | Asn | Lys | Ala | Leu | Gly | Leu |
|     |     |     |     | 565 |     |     |     |     | 570 |     |     |     |     | 575 |     |
| Pro | Lys | Tyr | Thr | Lys | Leu | Ile | Thr | Phe | Asn | Val | His | Asn | Arg | Tyr | Ala |
|     |     |     | 580 |     |     |     |     | 585 |     |     |     |     | 590 |     |     |
| Ser | Asn | Ile | Val | Glu | Ser | Ala | Tyr | Leu | Ile | Leu | Asn | Glu | Trp | Lys | Asn |
|     |     | 595 |     |     |     |     | 600 |     |     |     |     | 605 |     |     |     |
| Asn | Ile | Gln | Ser | Asp | Leu | Ile | Lys | Lys | Val | Thr | Asn | Tyr | Leu | Val | Asp |
|     | 610 |     |     |     |     | 615 |     |     |     |     | 620 |     |     |     |     |
| Gly | Asn | Gly | Arg | Phe | Val | Phe | Thr | Asp | Ile | Thr | Leu | Pro | Asn | Ile | Ala |
| 625 |     |     |     |     | 630 |     |     |     |     | 635 |     |     |     |     | 640 |
| Glu | Gln | Tyr | Thr | His | Gln | Asp | Glu | Ile | Tyr | Glu | Gln | Val | His | Ser | Lys |
|     |     |     |     | 645 |     |     |     |     | 650 |     |     |     |     | 655 |     |
| Gly | Leu | Tyr | Val | Pro | Glu | Ser | Arg | Ser | Ile | Leu | Leu | His | Gly | Pro | Ser |
|     |     |     | 660 |     |     |     |     | 665 |     |     |     |     | 670 |     |     |
| Lys | Gly | Val | Glu | Leu | Arg | Asn | Asp | Ser | Glu | Gly | Phe | Ile | His | Glu | Phe |
|     |     | 675 |     |     |     |     | 680 |     |     |     |     | 685 |     |     |     |
| Gly | His | Ala | Val | Asp | Asp | Tyr | Ala | Gly | Tyr | Leu | Leu | Asp | Lys | Asn | Gln |
|     | 690 |     |     |     |     | 695 |     |     |     |     | 700 |     |     |     |     |
| Ser | Asp | Leu | Val | Thr | Asn | Ser | Lys | Lys | Phe | Ile | Asp | Ile | Phe | Lys | Glu |
| 705 |     |     |     |     | 710 |     |     |     |     | 715 |     |     |     |     | 720 |
| Glu | Gly | Ser | Asn | Leu | Thr | Ser | Tyr | Gly | Arg | Thr | Asn | Glu | Ala | Glu | Phe |
|     |     |     |     | 725 |     |     |     |     | 730 |     |     |     |     | 735 |     |
| Phe | Ala | Glu | Ala | Phe | Arg | Leu | Met | His | Ser | Thr | Asp | His | Ala | Glu | Arg |
|     |     |     | 740 |     |     |     |     | 745 |     |     |     |     | 750 |     |     |
| Leu | Lys | Val | Gln | Lys | Asn | Ala | Pro | Lys | Thr | Phe | Gln | Phe | Ile | Asn | Asp |
|     |     | 755 |     |     |     |     | 760 |     |     |     |     | 765 |     |     |     |
| Gln | Ile | Lys | Phe | Ile | Ile | Asn | Ser |     |     |     |     |     |     |     |     |
|     | 770 |     |     |     |     | 775 |     |     |     |     |     |     |     |     |     |

( 2 ) INFORMATION FOR SEQ ID NO:3:

( i ) SEQUENCE CHARACTERISTICS:
  ( A ) LENGTH: 4235 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Bacillus anthracis ( i x ) FEATURE:
  ( A ) NAME/KEY: CDS
  ( B ) LOCATION: 1891..4095
  ( D ) OTHER INFORMATION: /product="Protective Antigen"

( x i ) SEQUENCE DESCRIPTION: SEQ ID NO:3:

| | | | | | |
|---|---|---|---|---|---|
| AAGCTTCTGT | CATTCGTAAA | TTTCAAATAG | AACGTAAATT | TAGACTTCTC | ATCATTAAAA | 60 |
| ATGAAAAATC | TTATCTTTTT | GATTCTATTG | TATATTTTA | TTAAGGTGTT | TAATAGTTAG | 120 |
| AAAAGACAGT | TGATGCTATT | ACTCCAGATA | AAATATAGCT | AACCATAAAT | TTATTAAAGA | 180 |
| AACCTTGTTG | TTCTAAATAA | TGATTTTGTG | GATTCCGGAA | TAGATACTGG | TGAGTTAGCT | 240 |
| CTAATTTTAT | AGTGATTTAA | CTAACAATTT | ATAAAGCAGC | ATAATTCAAA | TTTTTTAATT | 300 |
| GATTTTTCCT | GAAGCATAGT | ATAAAAGAGT | CAAGGTCTTC | TAGACTTGAC | TCTTGGAATC | 360 |
| ATTAGGAATT | AACAATATAT | ATAATGCGCT | AGACAGAATC | AAATTAAATG | CAAAAATGAA | 420 |
| TATTTAGTA | AGAGATCCAT | ATCATTATGA | TAATAACGGT | AATATTGTAG | GGGTTGATGA | 480 |
| TTCATATTTA | AAAAACGCAT | ATAAGCAAAT | ACTTAATTGG | TCAAGCGATG | GAGTTTCTTT | 540 |
| AAATCTAGAT | GAAGATGTAA | ATCAAGCACT | ATCTGGATAT | ATGCTTCAAA | TAAAAAAACC | 600 |
| TTCAAACCAC | CTAACAAACA | GCCCAGTTAC | AATTACATTA | GCAGGCAAGG | ACAGTGGTGT | 660 |
| TGGAGAATTG | TATAGAGTAT | TATCAGATGG | AGCAGGATTC | CTGGATTTCA | ATAAGTTTGA | 720 |
| TGAAAATTGG | CGATCATTAG | TAGATCCTGG | TGATGATGTT | TATGTGTATG | CTGTTACTAA | 780 |
| AGAAGATTTT | AATGCAGTTA | CTCGAGATGA | AAATGGTAAT | ATAGCGAATA | AATTAAAAAA | 840 |
| CACCTTAGTT | TTATCGGGTA | AAATAAAAGA | AATAAACATA | AAAACTACAA | ATATTAATAT | 900 |
| ATTTGTAGTT | TTTATGTTTA | TTATATACCT | CCTATTTTAT | ATTATTAGTA | GCACAGTTTT | 960 |
| TGCAAATCAT | GTAATTGTAT | ACTTATCTAT | GTAGAGGTAT | CACAACTTAT | GAATAGTGTA | 1020 |
| TTTTATTGAA | CGTTGGTTAG | CTTGGACAGT | TGTATGGATA | TGCATACTTT | ATAACGTATA | 1080 |
| AAATTTCACG | CACCACAATA | AAACTAATTT | AACAAAAACA | AAACACACC | TAAGATCATT | 1140 |
| CAGTTCTTTT | AATAAGGAGC | TGCCCACCAA | GCTAAACCTA | ATAATCTTT | GTTCACATA | 1200 |
| AGGTTTTTTT | CTAAATATAC | AGTGTAAGTT | ATTGTGAATT | TAACCAGTAT | ATATTAAAAA | 1260 |
| TGTTTATGT | TAACAAATTA | AATTGTAAAA | CCCCTCTTAA | GCATAGTTAA | GAGGGGTAGG | 1320 |
| TTTTAAATTT | TTTGTTGAAA | TTAGAAAAAA | TAATAAAAAA | ACAAACCTAT | TTCTTTCAG | 1380 |
| GTTGTTTTTG | GGTTACAAAA | CAAAAGAAA | ACATGTTTCA | AGGTACAATA | ATTATGGTTC | 1440 |
| TTTAGCTTTC | TGTAAAACAG | CCTTAATAGT | TGGATTTATG | ACTATTAAAG | TTAGTATACA | 1500 |
| GCATACACAA | TCTATTGAAG | GATATTTATA | ATGCAATTCC | CTAAAAATAG | TTTTGTATAA | 1560 |
| CCAGTTCTTT | TATCCGAACT | GATACACGTA | TTTTAGCATA | ATTTTTAATG | TATCTTCAAA | 1620 |
| AACAGCTTCT | GTGTCCTTTT | CTATTAAACA | TATAAATTCT | TTTTTATGTT | ATATATTTAT | 1680 |
| AAAAGTTCTG | TTTAAAAAGC | CAAAAATAAA | TAATTATCTC | TTTTTATTTA | TATTATATTG | 1740 |

```
AAACTAAAGT TTATTAATTT CAATATAATA TAAATTTAAT TTTATACAAA AAGGAGAACG     1800

TATATGAAAA AACGAAAAGT GTTAATACCA TTAATGGCAT TGTCTACGAT ATTAGTTTCA     1860

AGCACAGGTA ATTTAGAGGT GATTCAGGCA GAA GTT AAA CAG GAG AAC CGG TTA     1914
                                 Glu Val Lys Gln Glu Asn Arg Leu
                                  1               5

TTA AAT GAA TCA GAA TCA AGT TCC CAG GGG TTA CTA GGA TAC TAT TTT      1962
Leu Asn Glu Ser Glu Ser Ser Ser Gln Gly Leu Leu Gly Tyr Tyr Phe
     10              15                  20

AGT GAT TTG AAT TTT CAA GCA CCC ATG GTG GTT ACC TCT TCT ACT ACA      2010
Ser Asp Leu Asn Phe Gln Ala Pro Met Val Val Thr Ser Ser Thr Thr
 25              30                  35                      40

GGG GAT TTA TCT ATT CCT AGT TCT GAG TTA GAA AAT ATT CCA TCG GAA      2058
Gly Asp Leu Ser Ile Pro Ser Ser Glu Leu Glu Asn Ile Pro Ser Glu
             45                  50                  55

AAC CAA TAT TTT CAA TCT GCT ATT TGG TCA GGA TTT ATC AAA GTT AAG      2106
Asn Gln Tyr Phe Gln Ser Ala Ile Trp Ser Gly Phe Ile Lys Val Lys
             60                  65                  70

AAG AGT GAT GAA TAT ACA TTT GCT ACT TCC GCT GAT AAT CAT GTA ACA      2154
Lys Ser Asp Glu Tyr Thr Phe Ala Thr Ser Ala Asp Asn His Val Thr
         75                  80                  85

ATG TGG GTA GAT GAC CAA GAA GTG ATT AAT AAA GCT TCT AAT TCT AAC      2202
Met Trp Val Asp Asp Gln Glu Val Ile Asn Lys Ala Ser Asn Ser Asn
         90                  95                 100

AAA ATC AGA TTA GAA AAA GGA AGA TTA TAT CAA ATA AAA ATT CAA TAT      2250
Lys Ile Arg Leu Glu Lys Gly Arg Leu Tyr Gln Ile Lys Ile Gln Tyr
105             110                 115                     120

CAA CGA GAA AAT CCT ACT GAA AAA GGA TTG GAT TTC AAG TTG TAC TGG      2298
Gln Arg Glu Asn Pro Thr Glu Lys Gly Leu Asp Phe Lys Leu Tyr Trp
                125                 130                 135

ACC GAT TCT CAA AAT AAA AAA GAA GTG ATT TCT AGT GAT AAC TTA CAA      2346
Thr Asp Ser Gln Asn Lys Lys Glu Val Ile Ser Ser Asp Asn Leu Gln
            140                 145                 150

TTG CCA GAA TTA AAA CAA AAA TCT TCG AAC TCA AGA AAA AAG CGA AGT      2394
Leu Pro Glu Leu Lys Gln Lys Ser Ser Asn Ser Arg Lys Lys Arg Ser
        155                 160                 165

ACA AGT GCT GGA CCT ACG GTT CCA GAC CGT GAC AAT GAT GGA ATC CCT      2442
Thr Ser Ala Gly Pro Thr Val Pro Asp Arg Asp Asn Asp Gly Ile Pro
    170                 175                 180

GAT TCA TTA GAG GTA GAA GGA TAT ACG GTT GAT GTC AAA AAT AAA AGA      2490
Asp Ser Leu Glu Val Glu Gly Tyr Thr Val Asp Val Lys Asn Lys Arg
185             190                 195                     200

ACT TTT CTT TCA CCA TGG ATT TCT AAT ATT CAT GAA AAG AAA GGA TTA      2538
Thr Phe Leu Ser Pro Trp Ile Ser Asn Ile His Glu Lys Lys Gly Leu
                205                 210                 215

ACC AAA TAT AAA TCA TCT CCT GAA AAA TGG AGC ACG GCT TCT GAT CCG      2586
Thr Lys Tyr Lys Ser Ser Pro Glu Lys Trp Ser Thr Ala Ser Asp Pro
            220                 225                 230

TAC AGT GAT TTC GAA AAG GTT ACA GGA CGG ATT GAT AAG AAT GTA TCA      2634
Tyr Ser Asp Phe Glu Lys Val Thr Gly Arg Ile Asp Lys Asn Val Ser
        235                 240                 245

CCA GAG GCA AGA CAC CCC CTT GTG GCA GCT TAT CCG ATT GTA CAT GTA      2682
Pro Glu Ala Arg His Pro Leu Val Ala Ala Tyr Pro Ile Val His Val
    250                 255                 260

GAT ATG GAG AAT ATT ATT CTC TCA AAA AAT GAG GAT CAA TCC ACA CAG      2730
Asp Met Glu Asn Ile Ile Leu Ser Lys Asn Glu Asp Gln Ser Thr Gln
265             270                 275                 280

AAT ACT GAT AGT GAA ACG AGA ACA ATA AGT AAA AAT ACT TCT ACA AGT      2778
Asn Thr Asp Ser Glu Thr Arg Thr Ile Ser Lys Asn Thr Ser Thr Ser
                285                 290                 295
```

-continued

| | | | | | | | | | | | | | | | | |
|---|---|---|---|---|---|---|---|---|---|---|---|---|---|---|---|---|
| AGG | ACA | CAT | ACT | AGT | GAA | GTA | CAT | GGA | AAT | GCA | GAA | GTG | CAT | GCG | TCG | 2826 |
| Arg | Thr | His | Thr | Ser | Glu | Val | His | Gly | Asn | Ala | Glu | Val | His | Ala | Ser | |
| | | | 300 | | | | 305 | | | | | 310 | | | | |
| TTC | TTT | GAT | ATT | GGT | GGG | AGT | GTA | TCT | GCA | GGA | TTT | AGT | AAT | TCG | AAT | 2874 |
| Phe | Phe | Asp | Ile | Gly | Gly | Ser | Val | Ser | Ala | Gly | Phe | Ser | Asn | Ser | Asn | |
| | | | 315 | | | | 320 | | | | | 325 | | | | |
| TCA | AGT | ACG | GTC | GCA | ATT | GAT | CAT | TCA | CTA | TCT | CTA | GCA | GGG | GAA | AGA | 2922 |
| Ser | Ser | Thr | Val | Ala | Ile | Asp | His | Ser | Leu | Ser | Leu | Ala | Gly | Glu | Arg | |
| | | 330 | | | | | 335 | | | | 340 | | | | | |
| ACT | TGG | GCT | GAA | ACA | ATG | GGT | TTA | AAT | ACC | GCT | GAT | ACA | GCA | AGA | TTA | 2970 |
| Thr | Trp | Ala | Glu | Thr | Met | Gly | Leu | Asn | Thr | Ala | Asp | Thr | Ala | Arg | Leu | |
| 345 | | | | | 350 | | | | | 355 | | | | | 360 | |
| AAT | GCC | AAT | ATT | AGA | TAT | GTA | AAT | ACT | GGG | ACG | GCT | CCA | ATC | TAC | AAC | 3018 |
| Asn | Ala | Asn | Ile | Arg | Tyr | Val | Asn | Thr | Gly | Thr | Ala | Pro | Ile | Tyr | Asn | |
| | | | | 365 | | | | | 370 | | | | | 375 | | |
| GTG | TTA | CCA | ACG | ACT | TCG | TTA | GTG | TTA | GGA | AAA | AAT | CAA | ACA | CTC | GCG | 3066 |
| Val | Leu | Pro | Thr | Thr | Ser | Leu | Val | Leu | Gly | Lys | Asn | Gln | Thr | Leu | Ala | |
| | | | 380 | | | | 385 | | | | | 390 | | | | |
| ACA | ATT | AAA | GCT | AAG | GAA | AAC | CAA | TTA | AGT | CAA | ATA | CTT | GCA | CCT | AAT | 3114 |
| Thr | Ile | Lys | Ala | Lys | Glu | Asn | Gln | Leu | Ser | Gln | Ile | Leu | Ala | Pro | Asn | |
| | | 395 | | | | | 400 | | | | | 405 | | | | |
| AAT | TAT | TAT | CCT | TCT | AAA | AAC | TTG | GCG | CCA | ATC | GCA | TTA | AAT | GCA | CAA | 3162 |
| Asn | Tyr | Tyr | Pro | Ser | Lys | Asn | Leu | Ala | Pro | Ile | Ala | Leu | Asn | Ala | Gln | |
| | 410 | | | | | 415 | | | | | 420 | | | | | |
| GAC | GAT | TTC | AGT | TCT | ACT | CCA | ATT | ACA | ATG | AAT | TAC | AAT | CAA | TTT | CTT | 3210 |
| Asp | Asp | Phe | Ser | Ser | Thr | Pro | Ile | Thr | Met | Asn | Tyr | Asn | Gln | Phe | Leu | |
| 425 | | | | | 430 | | | | | 435 | | | | | 440 | |
| GAG | TTA | GAA | AAA | ACG | AAA | CAA | TTA | AGA | TTA | GAT | ACG | GAT | CAA | GTA | TAT | 3258 |
| Glu | Leu | Glu | Lys | Thr | Lys | Gln | Leu | Arg | Leu | Asp | Thr | Asp | Gln | Val | Tyr | |
| | | | | 445 | | | | | 450 | | | | | 455 | | |
| GGG | AAT | ATA | GCA | ACA | TAC | AAT | TTT | GAA | AAT | GGA | AGA | GTG | AGG | GTG | GAT | 3306 |
| Gly | Asn | Ile | Ala | Thr | Tyr | Asn | Phe | Glu | Asn | Gly | Arg | Val | Arg | Val | Asp | |
| | | | 460 | | | | | 465 | | | | | 470 | | | |
| ACA | GGC | TCG | AAC | TGG | AGT | GAA | GTG | TTA | CCG | CAA | ATT | CAA | GAA | ACA | ACT | 3354 |
| Thr | Gly | Ser | Asn | Trp | Ser | Glu | Val | Leu | Pro | Gln | Ile | Gln | Glu | Thr | Thr | |
| | | 475 | | | | | 480 | | | | | 485 | | | | |
| GCA | CGT | ATC | ATT | TTT | AAT | GGA | AAA | GAT | TTA | AAT | CTG | GTA | GAA | AGG | CGG | 3402 |
| Ala | Arg | Ile | Ile | Phe | Asn | Gly | Lys | Asp | Leu | Asn | Leu | Val | Glu | Arg | Arg | |
| | 490 | | | | | 495 | | | | | 500 | | | | | |
| ATA | GCG | GCG | GTT | AAT | CCT | AGT | GAT | CCA | TTA | GAA | ACG | ACT | AAA | CCG | GAT | 3450 |
| Ile | Ala | Ala | Val | Asn | Pro | Ser | Asp | Pro | Leu | Glu | Thr | Thr | Lys | Pro | Asp | |
| 505 | | | | | 510 | | | | | 515 | | | | | 520 | |
| ATG | ACA | TTA | AAA | GAA | GCC | CTT | AAA | ATA | GCA | TTT | GGA | TTT | AAC | GAA | CCG | 3498 |
| Met | Thr | Leu | Lys | Glu | Ala | Leu | Lys | Ile | Ala | Phe | Gly | Phe | Asn | Glu | Pro | |
| | | | | 525 | | | | | 530 | | | | | 535 | | |
| AAT | GGA | AAC | TTA | CAA | TAT | CAA | GGG | AAA | GAC | ATA | ACC | GAA | TTT | GAT | TTT | 3546 |
| Asn | Gly | Asn | Leu | Gln | Tyr | Gln | Gly | Lys | Asp | Ile | Thr | Glu | Phe | Asp | Phe | |
| | | | 540 | | | | | 545 | | | | | 550 | | | |
| AAT | TTC | GAT | CAA | CAA | ACA | TCT | CAA | AAT | ATC | AAG | AAT | CAG | TTA | GCG | GAA | 3594 |
| Asn | Phe | Asp | Gln | Gln | Thr | Ser | Gln | Asn | Ile | Lys | Asn | Gln | Leu | Ala | Glu | |
| | | 555 | | | | | 560 | | | | | 565 | | | | |
| TTA | AAC | GCA | ACT | AAC | ATA | TAT | ACT | GTA | TTA | GAT | AAA | ATC | AAA | TTA | AAT | 3642 |
| Leu | Asn | Ala | Thr | Asn | Ile | Tyr | Thr | Val | Leu | Asp | Lys | Ile | Lys | Leu | Asn | |
| | | 570 | | | | 575 | | | | | 580 | | | | | |
| GCA | AAA | ATG | AAT | ATT | TTA | ATA | AGA | GAT | AAA | CGT | TTT | CAT | TAT | GAT | AGA | 3690 |
| Ala | Lys | Met | Asn | Ile | Leu | Ile | Arg | Asp | Lys | Arg | Phe | His | Tyr | Asp | Arg | |
| 585 | | | | | 590 | | | | | 595 | | | | | 600 | |
| AAT | AAC | ATA | GCA | GTT | GGG | GCG | GAT | GAG | TCA | GTA | GTT | AAG | GAG | GCT | CAT | 3738 |
| Asn | Asn | Ile | Ala | Val | Gly | Ala | Asp | Glu | Ser | Val | Val | Lys | Glu | Ala | His | |
| | | | | 605 | | | | | 610 | | | | | 615 | | |

```
AGA  GAA  GTA  ATT  AAT  TCG  TCA  ACA  GAG  GGA  TTA  TTG  TTA  AAT  ATT  GAT         3786
Arg  Glu  Val  Ile  Asn  Ser  Ser  Thr  Glu  Gly  Leu  Leu  Leu  Asn  Ile  Asp
               620                      625                      630

AAG  GAT  ATA  AGA  AAA  ATA  TTA  TCA  GGT  TAT  ATT  GTA  GAA  ATT  GAA  GAT         3834
Lys  Asp  Ile  Arg  Lys  Ile  Leu  Ser  Gly  Tyr  Ile  Val  Glu  Ile  Glu  Asp
               635                      640                      645

ACT  GAA  GGG  CTT  AAA  GAA  GTT  ATA  AAT  GAC  AGA  TAT  GAT  ATG  TTG  AAT         3882
Thr  Glu  Gly  Leu  Lys  Glu  Val  Ile  Asn  Asp  Arg  Tyr  Asp  Met  Leu  Asn
     650                      655                      660

ATT  TCT  AGT  TTA  CGG  CAA  GAT  GGA  AAA  ACA  TTT  ATA  GAT  TTT  AAA  AAA         3930
Ile  Ser  Ser  Leu  Arg  Gln  Asp  Gly  Lys  Thr  Phe  Ile  Asp  Phe  Lys  Lys
665                      670                      675                      680

TAT  AAT  GAT  AAA  TTA  CCG  TTA  TAT  ATA  AGT  AAT  CCC  AAT  TAT  AAG  GTA         3978
Tyr  Asn  Asp  Lys  Leu  Pro  Leu  Tyr  Ile  Ser  Asn  Pro  Asn  Tyr  Lys  Val
               685                      690                      695

AAT  GTA  TAT  GCT  GTT  ACT  AAA  GAA  AAC  ACT  ATT  ATT  AAT  CCT  AGT  GAG         4026
Asn  Val  Tyr  Ala  Val  Thr  Lys  Glu  Asn  Thr  Ile  Ile  Asn  Pro  Ser  Glu
               700                      705                      710

AAT  GGG  GAT  ACT  AGT  ACC  AAC  GGG  ATC  AAG  AAA  ATT  TTA  ATC  TTT  TCT         4074
Asn  Gly  Asp  Thr  Ser  Thr  Asn  Gly  Ile  Lys  Lys  Ile  Leu  Ile  Phe  Ser
               715                      720                      725

AAA  AAA  GGC  TAT  GAG  ATA  GGA  TAAGGTAATT CTAGGTGATT TTTAAATTAT                     4125
Lys  Lys  Gly  Tyr  Glu  Ile  Gly
               730                      735

CTAAAAAACA  GTAAAATTAA  AACATACTCT  TTTTGTAAGA  AATACAAGGA  GAGTATGTTT                  4185

TAAACAGTAA  TCTAAATCAT  CATAATCCTT  TGAGATTGTT  TGTAGGATCC                              4235
```

( 2 ) INFORMATION FOR SEQ ID NO:4:

( i ) SEQUENCE CHARACTERISTICS:
        ( A ) LENGTH: 735 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu  Val  Lys  Gln  Glu  Asn  Arg  Leu  Leu  Asn  Glu  Ser  Glu  Ser  Ser
 1                 5                      10                      15

Gln  Gly  Leu  Leu  Gly  Tyr  Tyr  Phe  Ser  Asp  Leu  Asn  Phe  Gln  Ala  Pro
               20                      25                      30

Met  Val  Val  Thr  Ser  Ser  Thr  Gly  Asp  Leu  Ser  Ile  Pro  Ser  Ser
          35                      40                      45

Glu  Leu  Glu  Asn  Ile  Pro  Ser  Glu  Asn  Gln  Tyr  Phe  Gln  Ser  Ala  Ile
     50                      55                      60

Trp  Ser  Gly  Phe  Ile  Lys  Val  Lys  Lys  Ser  Asp  Glu  Tyr  Thr  Phe  Ala
65                       70                      75                      80

Thr  Ser  Ala  Asp  Asn  His  Val  Thr  Met  Trp  Val  Asp  Asp  Gln  Glu  Val
               85                      90                      95

Ile  Asn  Lys  Ala  Ser  Asn  Ser  Asn  Lys  Ile  Arg  Leu  Glu  Lys  Gly  Arg
               100                     105                     110

Leu  Tyr  Gln  Ile  Lys  Ile  Gln  Tyr  Gln  Arg  Glu  Asn  Pro  Thr  Glu  Lys
          115                     120                     125

Gly  Leu  Asp  Phe  Lys  Leu  Tyr  Trp  Thr  Asp  Ser  Gln  Asn  Lys  Lys  Glu
     130                     135                     140

Val  Ile  Ser  Ser  Asp  Asn  Leu  Gln  Leu  Pro  Glu  Leu  Lys  Gln  Lys  Ser
145                     150                     155                     160

Ser  Asn  Ser  Arg  Lys  Lys  Arg  Ser  Thr  Ser  Ala  Gly  Pro  Thr  Val  Pro
               165                     170                     175
```

```
Asp  Arg  Asp  Asn  Asp  Gly  Ile  Pro  Asp  Ser  Leu  Glu  Val  Glu  Gly  Tyr
               180                      185                     190

Thr  Val  Asp  Val  Lys  Asn  Lys  Arg  Thr  Phe  Leu  Ser  Pro  Trp  Ile  Ser
          195                     200                     205

Asn  Ile  His  Glu  Lys  Lys  Gly  Leu  Thr  Lys  Tyr  Lys  Ser  Ser  Pro  Glu
     210                     215                     220

Lys  Trp  Ser  Thr  Ala  Ser  Asp  Pro  Tyr  Ser  Asp  Phe  Glu  Lys  Val  Thr
225                      230                     235                          240

Gly  Arg  Ile  Asp  Lys  Asn  Val  Ser  Pro  Glu  Ala  Arg  His  Pro  Leu  Val
               245                     250                     255

Ala  Ala  Tyr  Pro  Ile  Val  His  Val  Asp  Met  Glu  Asn  Ile  Ile  Leu  Ser
               260                     265                     270

Lys  Asn  Glu  Asp  Gln  Ser  Thr  Gln  Asn  Thr  Asp  Ser  Glu  Thr  Arg  Thr
               275                     280                     285

Ile  Ser  Lys  Asn  Thr  Ser  Thr  Ser  Arg  Thr  His  Thr  Ser  Glu  Val  His
          290                     295                     300

Gly  Asn  Ala  Glu  Val  His  Ala  Ser  Phe  Phe  Asp  Ile  Gly  Gly  Ser  Val
305                      310                     315                          320

Ser  Ala  Gly  Phe  Ser  Asn  Ser  Asn  Ser  Ser  Thr  Val  Ala  Ile  Asp  His
                    325                     330                     335

Ser  Leu  Ser  Leu  Ala  Gly  Glu  Arg  Thr  Trp  Ala  Glu  Thr  Met  Gly  Leu
                    340                     345                     350

Asn  Thr  Ala  Asp  Thr  Ala  Arg  Leu  Asn  Ala  Asn  Ile  Arg  Tyr  Val  Asn
               355                     360                     365

Thr  Gly  Thr  Ala  Pro  Ile  Tyr  Asn  Val  Leu  Pro  Thr  Thr  Ser  Leu  Val
     370                     375                     380

Leu  Gly  Lys  Asn  Gln  Thr  Leu  Ala  Thr  Ile  Lys  Ala  Lys  Glu  Asn  Gln
385                      390                     395                          400

Leu  Ser  Gln  Ile  Leu  Ala  Pro  Asn  Asn  Tyr  Tyr  Pro  Ser  Lys  Asn  Leu
               405                     410                     415

Ala  Pro  Ile  Ala  Leu  Asn  Ala  Gln  Asp  Asp  Phe  Ser  Ser  Thr  Pro  Ile
               420                     425                     430

Thr  Met  Asn  Tyr  Asn  Gln  Phe  Leu  Glu  Leu  Glu  Lys  Thr  Lys  Gln  Leu
          435                     440                     445

Arg  Leu  Asp  Thr  Asp  Gln  Val  Tyr  Gly  Asn  Ile  Ala  Thr  Tyr  Asn  Phe
450                      455                     460

Glu  Asn  Gly  Arg  Val  Arg  Val  Asp  Thr  Gly  Ser  Asn  Trp  Ser  Glu  Val
465                      470                     475                          480

Leu  Pro  Gln  Ile  Gln  Glu  Thr  Thr  Ala  Arg  Ile  Ile  Phe  Asn  Gly  Lys
               485                     490                     495

Asp  Leu  Asn  Leu  Val  Glu  Arg  Arg  Ile  Ala  Ala  Val  Asn  Pro  Ser  Asp
               500                     505                     510

Pro  Leu  Glu  Thr  Thr  Lys  Pro  Asp  Met  Thr  Leu  Lys  Glu  Ala  Leu  Lys
          515                     520                     525

Ile  Ala  Phe  Gly  Phe  Asn  Glu  Pro  Asn  Gly  Asn  Leu  Gln  Tyr  Gln  Gly
          530                     535                     540

Lys  Asp  Ile  Thr  Glu  Phe  Asp  Phe  Asn  Phe  Asp  Gln  Gln  Thr  Ser  Gln
545                      550                     555                          560

Asn  Ile  Lys  Asn  Gln  Leu  Ala  Glu  Leu  Asn  Ala  Thr  Asn  Ile  Tyr  Thr
                    565                     570                     575

Val  Leu  Asp  Lys  Ile  Lys  Leu  Asn  Ala  Lys  Met  Asn  Ile  Leu  Ile  Arg
               580                     585                     590

Asp  Lys  Arg  Phe  His  Tyr  Asp  Arg  Asn  Asn  Ile  Ala  Val  Gly  Ala  Asp
```

-continued

|   |   |   | 595 |   |   |   | 600 |   |   |   | 605 |   |   |
|---|---|---|---|---|---|---|---|---|---|---|---|---|---|
| Glu | Ser | Val | Val | Lys | Glu | Ala | His | Arg | Glu | Val | Ile | Asn | Ser | Ser | Thr |
|   | 610 |   |   |   |   | 615 |   |   |   |   | 620 |   |   |   |   |
| Glu | Gly | Leu | Leu | Leu | Asn | Ile | Asp | Lys | Asp | Ile | Arg | Lys | Ile | Leu | Ser |
| 625 |   |   |   |   | 630 |   |   |   | 635 |   |   |   |   |   | 640 |
| Gly | Tyr | Ile | Val | Glu | Ile | Glu | Asp | Thr | Glu | Gly | Leu | Lys | Glu | Val | Ile |
|   |   |   |   | 645 |   |   |   |   | 650 |   |   |   |   | 655 |   |
| Asn | Asp | Arg | Tyr | Asp | Met | Leu | Asn | Ile | Ser | Ser | Leu | Arg | Gln | Asp | Gly |
|   |   |   | 660 |   |   |   |   | 665 |   |   |   |   | 670 |   |   |
| Lys | Thr | Phe | Ile | Asp | Phe | Lys | Lys | Tyr | Asn | Asp | Lys | Leu | Pro | Leu | Tyr |
|   |   | 675 |   |   |   |   | 680 |   |   |   |   | 685 |   |   |   |
| Ile | Ser | Asn | Pro | Asn | Tyr | Lys | Val | Asn | Val | Tyr | Ala | Val | Thr | Lys | Glu |
|   |   | 690 |   |   |   |   | 695 |   |   |   |   | 700 |   |   |   |
| Asn | Thr | Ile | Ile | Asn | Pro | Ser | Glu | Asn | Gly | Asp | Thr | Ser | Thr | Asn | Gly |
| 705 |   |   |   |   | 710 |   |   |   |   | 715 |   |   |   |   | 720 |
| Ile | Lys | Lys | Ile | Leu | Ile | Phe | Ser | Lys | Lys | Gly | Tyr | Glu | Ile | Gly |   |
|   |   |   |   |   | 725 |   |   |   | 730 |   |   |   |   | 735 |   |

( 2 ) INFORMATION FOR SEQ ID NO:5:

( i ) SEQUENCE CHARACTERISTICS:
( A ) LENGTH: 1368 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus anthracis ( i x ) FEATURE:
( A ) NAME/KEY: CDS
( B ) LOCATION: 1..1368
( D ) OTHER INFORMATION: /product="LF(1-254)--TR--PE(401-602)"

( x i ) SEQUENCE DESCRIPTION: SEQ ID NO:5:

GCG GGC GGT CAT GGT GAT GTA GGT ATG CAC GTA AAA GAG AAA GAG AAA 48
Ala Gly Gly His Gly Asp Val Gly Met His Val Lys Glu Lys Glu Lys
1 5 10 15

AAT AAA GAT GAG AAT AAG AGA AAA GAT GAA GAA CGA AAT AAA ACA CAG 96
Asn Lys Asp Glu Asn Lys Arg Lys Asp Glu Glu Arg Asn Lys Thr Gln
20 25 30

GAA GAG CAT TTA AAG GAA ATC ATG AAA CAC ATT GTA AAA ATA GAA GTA 144
Glu Glu His Leu Lys Glu Ile Met Lys His Ile Val Lys Ile Glu Val
35 40 45

AAA GGG GAG GAA GCT GTT AAA AAA GAG GCA GCA GAA AAG CTA CTT GAG 192
Lys Gly Glu Glu Ala Val Lys Lys Glu Ala Ala Glu Lys Leu Leu Glu
50 55 60

AAA GTA CCA TCT GAT GTT TTA GAG ATG TAT AAA GCA ATT GGA GGA AAG 240
Lys Val Pro Ser Asp Val Leu Glu Met Tyr Lys Ala Ile Gly Gly Lys
65 70 75 80

ATA TAT ATT GTG GAT GGT GAT ATT ACA AAA CAT ATA TCT TTA GAA GCA 288
Ile Tyr Ile Val Asp Gly Asp Ile Thr Lys His Ile Ser Leu Glu Ala
85 90 95

TTA TCT GAA GAT AAG AAA AAA ATA AAA GAC ATT TAT GGG AAA GAT GCT 336
Leu Ser Glu Asp Lys Lys Lys Ile Lys Asp Ile Tyr Gly Lys Asp Ala
100 105 110

TTA TTA CAT GAA CAT TAT GTA TAT GCA AAA GAA GGA TAT GAA CCC GTA 384

| | | | | | | | | | | | | | | | | |
|---|---|---|---|---|---|---|---|---|---|---|---|---|---|---|---|---|
| Leu | Leu | His | Glu | His | Tyr | Val | Tyr | Ala | Lys | Glu | Gly | Tyr | Glu | Pro | Val | |
| | | 115 | | | | 120 | | | | | 125 | | | | | |
| CTT | GTA | ATC | CAA | TCT | TCG | GAA | GAT | TAT | GTA | GAA | AAT | ACT | GAA | AAG | GCA | 432 |
| Leu | Val | Ile | Gln | Ser | Ser | Glu | Asp | Tyr | Val | Glu | Asn | Thr | Glu | Lys | Ala | |
| | 130 | | | | 135 | | | | | 140 | | | | | | |
| CTG | AAC | GTT | TAT | TAT | GAA | ATA | GGT | AAG | ATA | TTA | TCA | AGG | GAT | ATT | TTA | 480 |
| Leu | Asn | Val | Tyr | Tyr | Glu | Ile | Gly | Lys | Ile | Leu | Ser | Arg | Asp | Ile | Leu | |
| 145 | | | | | 150 | | | | | 155 | | | | | 160 | |
| AGT | AAA | ATT | AAT | CAA | CCA | TAT | CAG | AAA | TTT | TTA | GAT | GTA | TTA | AAT | ACC | 528 |
| Ser | Lys | Ile | Asn | Gln | Pro | Tyr | Gln | Lys | Phe | Leu | Asp | Val | Leu | Asn | Thr | |
| | | | | 165 | | | | | 170 | | | | | 175 | | |
| ATT | AAA | AAT | GCA | TCT | GAT | TCA | GAT | GGA | CAA | GAT | CTT | TTA | TTT | ACT | AAT | 576 |
| Ile | Lys | Asn | Ala | Ser | Asp | Ser | Asp | Gly | Gln | Asp | Leu | Leu | Phe | Thr | Asn | |
| | | | 180 | | | | | 185 | | | | | 190 | | | |
| CAG | CTT | AAG | GAA | CAT | CCC | ACA | GAC | TTT | TCT | GTA | GAA | TTC | TTG | GAA | CAA | 624 |
| Gln | Leu | Lys | Glu | His | Pro | Thr | Asp | Phe | Ser | Val | Glu | Phe | Leu | Glu | Gln | |
| | | 195 | | | | | 200 | | | | | 205 | | | | |
| AAT | AGC | AAT | GAG | GTA | CAA | GAA | GTA | TTT | GCG | AAA | GCT | TTT | GCA | TAT | TAT | 672 |
| Asn | Ser | Asn | Glu | Val | Gln | Glu | Val | Phe | Ala | Lys | Ala | Phe | Ala | Tyr | Tyr | |
| | 210 | | | | | 215 | | | | | 220 | | | | | |
| ATC | GAG | CCA | CAG | CAT | CGT | GAT | GTT | TTA | CAG | CTT | TAT | GCA | CCG | GAA | GCT | 720 |
| Ile | Glu | Pro | Gln | His | Arg | Asp | Val | Leu | Gln | Leu | Tyr | Ala | Pro | Glu | Ala | |
| 225 | | | | | 230 | | | | | 235 | | | | | 240 | |
| TTT | AAT | TAC | ATG | GAT | AAA | TTT | AAC | GAA | CAA | GAA | ATA | AAT | CTA | CTC | GGC | 768 |
| Phe | Asn | Tyr | Met | Asp | Lys | Phe | Asn | Glu | Gln | Glu | Ile | Asn | Leu | Leu | Gly | |
| | | | | 245 | | | | | 250 | | | | | 255 | | |
| GAC | GGC | GGC | GAC | GTC | AGC | TTC | AGC | ACC | CGC | GGC | ACG | CAG | AAC | TGG | ACG | 816 |
| Asp | Gly | Gly | Asp | Val | Ser | Phe | Ser | Thr | Arg | Gly | Thr | Gln | Asn | Trp | Thr | |
| | | | 260 | | | | | 265 | | | | | 270 | | | |
| GTG | GAG | CGG | CTG | CTC | CAG | GCG | CAC | CGC | CAA | CTG | GAG | GAG | CGC | GGC | TAT | 864 |
| Val | Glu | Arg | Leu | Leu | Gln | Ala | His | Arg | Gln | Leu | Glu | Glu | Arg | Gly | Tyr | |
| | | 275 | | | | | 280 | | | | | 285 | | | | |
| GTG | TTC | GTC | GGC | TAC | CAC | GGC | ACC | TTC | CTC | GAA | GCG | GCG | CAA | AGC | ATC | 912 |
| Val | Phe | Val | Gly | Tyr | His | Gly | Thr | Phe | Leu | Glu | Ala | Ala | Gln | Ser | Ile | |
| | 290 | | | | | 295 | | | | | 300 | | | | | |
| GTC | TTC | GGC | GGG | GTG | CGC | GCG | CGC | AGC | CAG | GAC | CTC | GAC | GCG | ATC | TGG | 960 |
| Val | Phe | Gly | Gly | Val | Arg | Ala | Arg | Ser | Gln | Asp | Leu | Asp | Ala | Ile | Trp | |
| 305 | | | | | 310 | | | | | 315 | | | | | 320 | |
| CGC | GGT | TTC | TAT | ATC | GCC | GGC | GAT | CCG | GCG | CTG | GCC | TAC | GGC | TAC | GCC | 1008 |
| Arg | Gly | Phe | Tyr | Ile | Ala | Gly | Asp | Pro | Ala | Leu | Ala | Tyr | Gly | Tyr | Ala | |
| | | | | 325 | | | | | 330 | | | | | 335 | | |
| CAG | GAC | CAG | GAA | CCC | GAC | GCA | CGC | GGC | CGG | ATC | CGC | AAC | GGT | GCC | CTG | 1056 |
| Gln | Asp | Gln | Glu | Pro | Asp | Ala | Arg | Gly | Arg | Ile | Arg | Asn | Gly | Ala | Leu | |
| | | | 340 | | | | | 345 | | | | | 350 | | | |
| CTG | CGG | GTC | TAT | GTG | CCG | CGC | TCG | AGC | CTG | CCG | GGC | TTC | TAC | CGC | ACC | 1104 |
| Leu | Arg | Val | Tyr | Val | Pro | Arg | Ser | Ser | Leu | Pro | Gly | Phe | Tyr | Arg | Thr | |
| | | 355 | | | | | 360 | | | | | 365 | | | | |
| AGC | CTG | ACC | CTG | GCC | GCG | CCG | GAG | GCG | GCG | GGC | GAG | GTC | GAA | CGG | CTG | 1152 |
| Ser | Leu | Thr | Leu | Ala | Ala | Pro | Glu | Ala | Ala | Gly | Glu | Val | Glu | Arg | Leu | |
| | 370 | | | | | 375 | | | | | 380 | | | | | |
| ATC | GGC | CAT | CCG | CTG | CCG | CTG | CGC | CTG | GAC | GCC | ATC | ACC | GGC | CCC | GAG | 1200 |
| Ile | Gly | His | Pro | Leu | Pro | Leu | Arg | Leu | Asp | Ala | Ile | Thr | Gly | Pro | Glu | |
| 385 | | | | | 390 | | | | | 395 | | | | | 400 | |
| GAG | GAA | GGC | GGG | CGC | CTG | GAG | ACC | ATT | CTC | GGC | TGG | CCG | CTG | GCC | GAG | 1248 |
| Glu | Glu | Gly | Gly | Arg | Leu | Glu | Thr | Ile | Leu | Gly | Trp | Pro | Leu | Ala | Glu | |
| | | | | 405 | | | | | 410 | | | | | 415 | | |
| CGC | ACC | GTG | GTG | ATT | CCC | TCG | GCG | ATC | CCC | ACC | GAC | CCG | CGC | AAC | GTC | 1296 |
| Arg | Thr | Val | Val | Ile | Pro | Ser | Ala | Ile | Pro | Thr | Asp | Pro | Arg | Asn | Val | |
| | | | 420 | | | | | 425 | | | | | 430 | | | |
| GGC | GGC | GAC | CTC | GAC | CCG | TCC | AGC | ATC | CCC | GAC | AAG | GAA | CAG | GCG | ATC | 1344 |

|  |  |  |  |  |  |  |
|---|---|---|---|---|---|---|
| Gly | Gly | Asp | Leu | Asp | Pro | Ser | Ser | Ile | Pro | Asp | Lys | Glu | Gln | Ala | Ile |
|  |  |  | 435 |  |  |  | 440 |  |  |  | 445 |  |  |  |  |

```
AGC  GCC  CTG  CCG  GAC  TAC  GCC  AGC                                              1368
Ser  Ala  Leu  Pro  Asp  Tyr  Ala  Ser
     450                 455
```

( 2 ) INFORMATION FOR SEQ ID NO:6:

( i ) SEQUENCE CHARACTERISTICS:
        ( A ) LENGTH: 456 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Ala  Gly  Gly  His  Gly  Asp  Val  Gly  Met  His  Val  Lys  Glu  Lys  Glu  Lys
 1             5                      10                      15

Asn  Lys  Asp  Glu  Asn  Lys  Arg  Lys  Asp  Glu  Glu  Arg  Asn  Lys  Thr  Gln
               20                      25                      30

Glu  Glu  His  Leu  Lys  Glu  Ile  Met  Lys  His  Ile  Val  Lys  Ile  Glu  Val
          35                      40                      45

Lys  Gly  Glu  Glu  Ala  Val  Lys  Lys  Glu  Ala  Ala  Glu  Lys  Leu  Leu  Glu
     50                      55                      60

Lys  Val  Pro  Ser  Asp  Val  Leu  Glu  Met  Tyr  Lys  Ala  Ile  Gly  Gly  Lys
65                       70                      75                       80

Ile  Tyr  Ile  Val  Asp  Gly  Asp  Ile  Thr  Lys  His  Ile  Ser  Leu  Glu  Ala
                    85                      90                      95

Leu  Ser  Glu  Asp  Lys  Lys  Lys  Ile  Lys  Asp  Ile  Tyr  Gly  Lys  Asp  Ala
               100                     105                     110

Leu  Leu  His  Glu  His  Tyr  Val  Tyr  Ala  Lys  Glu  Gly  Tyr  Glu  Pro  Val
          115                     120                     125

Leu  Val  Ile  Gln  Ser  Ser  Glu  Asp  Tyr  Val  Glu  Asn  Thr  Glu  Lys  Ala
     130                     135                     140

Leu  Asn  Val  Tyr  Tyr  Glu  Ile  Gly  Lys  Ile  Leu  Ser  Arg  Asp  Ile  Leu
145                      150                     155                      160

Ser  Lys  Ile  Asn  Gln  Pro  Tyr  Gln  Lys  Phe  Leu  Asp  Val  Leu  Asn  Thr
                    165                     170                     175

Ile  Lys  Asn  Ala  Ser  Asp  Ser  Asp  Gly  Gln  Asp  Leu  Leu  Phe  Thr  Asn
               180                     185                     190

Gln  Leu  Lys  Glu  His  Pro  Thr  Asp  Phe  Ser  Val  Glu  Phe  Leu  Glu  Gln
          195                     200                     205

Asn  Ser  Asn  Glu  Val  Gln  Glu  Val  Phe  Ala  Lys  Ala  Phe  Ala  Tyr  Tyr
     210                     215                     220

Ile  Glu  Pro  Gln  His  Arg  Asp  Val  Leu  Gln  Leu  Tyr  Ala  Pro  Glu  Ala
225                      230                     235                      240

Phe  Asn  Tyr  Met  Asp  Lys  Phe  Asn  Glu  Gln  Glu  Ile  Asn  Leu  Leu  Gly
                    245                     250                     255

Asp  Gly  Gly  Asp  Val  Ser  Phe  Ser  Thr  Arg  Gly  Thr  Gln  Asn  Trp  Thr
               260                     265                     270

Val  Glu  Arg  Leu  Leu  Gln  Ala  His  Arg  Gln  Leu  Glu  Glu  Arg  Gly  Tyr
          275                     280                     285

Val  Phe  Val  Gly  Tyr  His  Gly  Thr  Phe  Leu  Glu  Ala  Ala  Gln  Ser  Ile
     290                     295                     300

Val  Phe  Gly  Gly  Val  Arg  Ala  Arg  Ser  Gln  Asp  Leu  Asp  Ala  Ile  Trp
305                      310                     315                      320

Arg  Gly  Phe  Tyr  Ile  Ala  Gly  Asp  Pro  Ala  Leu  Ala  Tyr  Gly  Tyr  Ala
```

|           |           |           |           |           | 325       |           |           |           | 330       |           |           |           |           | 335       |
|-----------|-----------|-----------|-----------|-----------|-----------|-----------|-----------|-----------|-----------|-----------|-----------|-----------|-----------|-----------|

```
Gln   Asp   Gln   Glu   Pro   Asp   Ala   Arg   Gly   Arg   Ile   Arg   Asn   Gly   Ala   Leu
                  340                             345                             350

Leu   Arg   Val   Tyr   Val   Pro   Arg   Ser   Ser   Leu   Pro   Gly   Phe   Tyr   Arg   Thr
                  355                             360                             365

Ser   Leu   Thr   Leu   Ala   Ala   Pro   Glu   Ala   Ala   Gly   Glu   Val   Glu   Arg   Leu
            370                       375                       380

Ile   Gly   His   Pro   Leu   Pro   Leu   Arg   Leu   Asp   Ala   Ile   Thr   Gly   Pro   Glu
385                           390                       395                             400

Glu   Glu   Gly   Gly   Arg   Leu   Glu   Thr   Ile   Leu   Gly   Trp   Pro   Leu   Ala   Glu
                        405                       410                             415

Arg   Thr   Val   Val   Ile   Pro   Ser   Ala   Ile   Pro   Thr   Asp   Pro   Arg   Asn   Val
                  420                       425                             430

Gly   Gly   Asp   Leu   Asp   Pro   Ser   Ser   Ile   Pro   Asp   Lys   Glu   Gln   Ala   Ile
                  435                       440                       445

Ser   Ala   Leu   Pro   Asp   Tyr   Ala   Ser
      450                       455
```

(2) INFORMATION FOR SEQ ID NO:7:

(i) SEQUENCE CHARACTERISTICS:
        (A) LENGTH: 1425 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Bacillus anthracis (ix) FEATURE:
        (A) NAME/KEY: CDS
        (B) LOCATION: 1..1416
        (D) OTHER INFORMATION: /product="LF(1-254)--TR--PE(398-613)"

(xi) SEQUENCE DESCRIPTION: SEQ ID NO:7:

```
ATG   GTA   CCA   GCG   GGC   GGT   CAT   GGT   GAT   GTA   GGT   ATG   CAC   GTA   AAA   GAG      48
Met   Val   Pro   Ala   Gly   Gly   His   Gly   Asp   Val   Gly   Met   His   Val   Lys   Glu
1                       5                             10                            15

AAA   GAG   AAA   AAT   AAA   GAT   GAG   AAT   AAG   AGA   AAA   GAT   GAA   GAA   CGA   AAT      96
Lys   Glu   Lys   Asn   Lys   Asp   Glu   Asn   Lys   Arg   Lys   Asp   Glu   Glu   Arg   Asn
            20                            25                            30

AAA   ACA   CAG   GAA   GAG   CAT   TTA   AAG   GAA   ATC   ATG   AAA   CAC   ATT   GTA   AAA     144
Lys   Thr   Gln   Glu   Glu   His   Leu   Lys   Glu   Ile   Met   Lys   His   Ile   Val   Lys
                  35                            40                      45

ATA   GAA   GTA   AAA   GGG   GAG   GAA   GCT   GTT   AAA   AAA   GAG   GCA   GCA   GAA   AAG     192
Ile   Glu   Val   Lys   Gly   Glu   Glu   Ala   Val   Lys   Lys   Glu   Ala   Ala   Glu   Lys
      50                            55                            60

CTA   CTT   GAG   AAA   GTA   CCA   TCT   GAT   GTT   TTA   GAG   ATG   TAT   AAA   GCA   ATT     240
Leu   Leu   Glu   Lys   Val   Pro   Ser   Asp   Val   Leu   Glu   Met   Tyr   Lys   Ala   Ile
65                      70                            75                            80

GGA   GGA   AAG   ATA   TAT   ATT   GTG   GAT   GGT   GAT   ATT   ACA   AAA   CAT   ATA   TCT     288
Gly   Gly   Lys   Ile   Tyr   Ile   Val   Asp   Gly   Asp   Ile   Thr   Lys   His   Ile   Ser
                        85                            90                            95

TTA   GAA   GCA   TTA   TCT   GAA   GAT   AAG   AAA   AAA   ATA   AAA   GAC   ATT   TAT   GGG     336
Leu   Glu   Ala   Leu   Ser   Glu   Asp   Lys   Lys   Lys   Ile   Lys   Asp   Ile   Tyr   Gly
                  100                           105                           110

AAA   GAT   GCT   TTA   TTA   CAT   GAA   CAT   TAT   GTA   TAT   GCA   AAA   GAA   GGA   TAT     384
Lys   Asp   Ala   Leu   Leu   His   Glu   His   Tyr   Val   Tyr   Ala   Lys   Glu   Gly   Tyr
            115                           120                           125
```

-continued

| | | | | | | | | | | | | | | | | |
|---|---|---|---|---|---|---|---|---|---|---|---|---|---|---|---|---|
| GAA | CCC | GTA | CTT | GTA | ATC | CAA | TCT | TCG | GAA | GAT | TAT | GTA | GAA | AAT | ACT | 432 |
| Glu | Pro | Val | Leu | Val | Ile | Gln | Ser | Ser | Glu | Asp | Tyr | Val | Glu | Asn | Thr | |
| | 130 | | | | 135 | | | | | 140 | | | | | | |
| GAA | AAG | GCA | CTG | AAC | GTT | TAT | TAT | GAA | ATA | GGT | AAG | ATA | TTA | TCA | AGG | 480 |
| Glu | Lys | Ala | Leu | Asn | Val | Tyr | Tyr | Glu | Ile | Gly | Lys | Ile | Leu | Ser | Arg | |
| 145 | | | | | 150 | | | | | 155 | | | | | 160 | |
| GAT | ATT | TTA | AGT | AAA | ATT | AAT | CAA | CCA | TAT | CAG | AAA | TTT | TTA | GAT | GTA | 528 |
| Asp | Ile | Leu | Ser | Lys | Ile | Asn | Gln | Pro | Tyr | Gln | Lys | Phe | Leu | Asp | Val | |
| | | | | 165 | | | | | 170 | | | | | 175 | | |
| TTA | AAT | ACC | ATT | AAA | AAT | GCA | TCT | GAT | TCA | GAT | GGA | CAA | GAT | CTT | TTA | 576 |
| Leu | Asn | Thr | Ile | Lys | Asn | Ala | Ser | Asp | Ser | Asp | Gly | Gln | Asp | Leu | Leu | |
| | | | 180 | | | | | 185 | | | | | 190 | | | |
| TTT | ACT | AAT | CAG | CTT | AAG | GAA | CAT | CCC | ACA | GAC | TTT | TCT | GTA | GAA | TTC | 624 |
| Phe | Thr | Asn | Gln | Leu | Lys | Glu | His | Pro | Thr | Asp | Phe | Ser | Val | Glu | Phe | |
| | | 195 | | | | | 200 | | | | | 205 | | | | |
| TTG | GAA | CAA | AAT | AGC | AAT | GAG | GTA | CAA | GAA | GTA | TTT | GCG | AAA | GCT | TTT | 672 |
| Leu | Glu | Gln | Asn | Ser | Asn | Glu | Val | Gln | Glu | Val | Phe | Ala | Lys | Ala | Phe | |
| | 210 | | | | | 215 | | | | | 220 | | | | | |
| GCA | TAT | TAT | ATC | GAG | CCA | CAG | CAT | CGT | GAT | GTT | TTA | CAG | CTT | TAT | GCA | 720 |
| Ala | Tyr | Tyr | Ile | Glu | Pro | Gln | His | Arg | Asp | Val | Leu | Gln | Leu | Tyr | Ala | |
| 225 | | | | | 230 | | | | | 235 | | | | | 240 | |
| CCG | GAA | GCT | TTT | AAT | TAC | ATG | GAT | AAA | TTT | AAC | GAA | CAA | GAA | ATA | AAT | 768 |
| Pro | Glu | Ala | Phe | Asn | Tyr | Met | Asp | Lys | Phe | Asn | Glu | Gln | Glu | Ile | Asn | |
| | | | | 245 | | | | | 250 | | | | | 255 | | |
| CTA | ACG | CGT | GCG | GAG | TTC | CTC | GGC | GAC | GGC | GGC | GAC | GTC | AGC | TTC | AGC | 816 |
| Leu | Thr | Arg | Ala | Glu | Phe | Leu | Gly | Asp | Gly | Gly | Asp | Val | Ser | Phe | Ser | |
| | | | 260 | | | | | 265 | | | | | 270 | | | |
| ACC | CGC | GGC | ACG | CAG | AAC | TGG | ACG | GTG | GAG | CGG | CTG | CTC | CAG | GCG | CAC | 864 |
| Thr | Arg | Gly | Thr | Gln | Asn | Trp | Thr | Val | Glu | Arg | Leu | Leu | Gln | Ala | His | |
| | | 275 | | | | | 280 | | | | | 285 | | | | |
| CGC | CAA | CTG | GAG | GAG | CGC | GGC | TAT | GTG | TTC | GTC | GGC | TAC | CAC | GGC | ACC | 912 |
| Arg | Gln | Leu | Glu | Glu | Arg | Gly | Tyr | Val | Phe | Val | Gly | Tyr | His | Gly | Thr | |
| | 290 | | | | | 295 | | | | | 300 | | | | | |
| TTC | CTC | GAA | GCG | GCG | CAA | AGC | ATC | GTC | TTC | GGC | GGG | GTG | CGC | GCG | CGC | 960 |
| Phe | Leu | Glu | Ala | Ala | Gln | Ser | Ile | Val | Phe | Gly | Gly | Val | Arg | Ala | Arg | |
| 305 | | | | | 310 | | | | | 315 | | | | | 320 | |
| AGC | CAG | GAC | CTC | GAC | GCG | ATC | TGG | CGC | GGT | TTC | TAT | ATC | GCC | GGC | GAT | 1008 |
| Ser | Gln | Asp | Leu | Asp | Ala | Ile | Trp | Arg | Gly | Phe | Tyr | Ile | Ala | Gly | Asp | |
| | | | | 325 | | | | | 330 | | | | | 335 | | |
| CCG | GCG | CTG | GCC | TAC | GGC | TAC | GCC | CAG | GAC | CAG | GAA | CCC | GAC | GCA | CGC | 1056 |
| Pro | Ala | Leu | Ala | Tyr | Gly | Tyr | Ala | Gln | Asp | Gln | Glu | Pro | Asp | Ala | Arg | |
| | | | 340 | | | | | 345 | | | | | 350 | | | |
| GGC | CGG | ATC | CGC | AAC | GGT | GCC | CTG | CTG | CGG | GTC | TAT | GTG | CCG | CGC | TCG | 1104 |
| Gly | Arg | Ile | Arg | Asn | Gly | Ala | Leu | Leu | Arg | Val | Tyr | Val | Pro | Arg | Ser | |
| | | 355 | | | | | 360 | | | | | 365 | | | | |
| AGC | CTG | CCG | GGC | TTC | TAC | CGC | ACC | AGC | CTG | ACC | CTG | GCC | GCG | CCG | GAG | 1152 |
| Ser | Leu | Pro | Gly | Phe | Tyr | Arg | Thr | Ser | Leu | Thr | Leu | Ala | Ala | Pro | Glu | |
| | 370 | | | | | 375 | | | | | 380 | | | | | |
| GCG | GCG | GGC | GAG | GTC | GAA | CGG | CTG | ATC | GGC | CAT | CCG | CTG | CCG | CTG | CGC | 1200 |
| Ala | Ala | Gly | Glu | Val | Glu | Arg | Leu | Ile | Gly | His | Pro | Leu | Pro | Leu | Arg | |
| 385 | | | | | 390 | | | | | 395 | | | | | 400 | |
| CTG | GAC | GCC | ATC | ACC | GGC | CCC | GAG | GAG | GAA | GGC | GGG | CGC | CTG | GAG | ACC | 1248 |
| Leu | Asp | Ala | Ile | Thr | Gly | Pro | Glu | Glu | Glu | Gly | Gly | Arg | Leu | Glu | Thr | |
| | | | | 405 | | | | | 410 | | | | | 415 | | |
| ATT | CTC | GGC | TGG | CCG | CTG | GCC | GAG | CGC | ACC | GTG | GTG | ATT | CCC | TCG | GCG | 1296 |
| Ile | Leu | Gly | Trp | Pro | Leu | Ala | Glu | Arg | Thr | Val | Val | Ile | Pro | Ser | Ala | |
| | | | 420 | | | | | 425 | | | | | 430 | | | |
| ATC | CCC | ACC | GAC | CCG | CGC | AAC | GTC | GGC | GGC | GAC | CTC | GAC | CCG | TCC | AGC | 1344 |
| Ile | Pro | Thr | Asp | Pro | Arg | Asn | Val | Gly | Gly | Asp | Leu | Asp | Pro | Ser | Ser | |
| | | 435 | | | | | 440 | | | | | 445 | | | | |

| | | | | | | | | | | | | | | | | |
|---|---|---|---|---|---|---|---|---|---|---|---|---|---|---|---|---|
| ATC | CCC | GAC | AAG | GAA | CAG | GCG | ATC | AGC | GCC | CTG | CCG | GAC | TAC | GCC | AGC | 1392 |
| Ile | Pro | Asp | Lys | Glu | Gln | Ala | Ile | Ser | Ala | Leu | Pro | Asp | Tyr | Ala | Ser | |
| | 450 | | | | 455 | | | | | 460 | | | | | | |
| CAG | CCC | GGC | AAA | CCG | CCG | CGC | GAG | GACCTGAAG | | | | | | | | 1425 |
| Gln | Pro | Gly | Lys | Pro | Pro | Arg | Glu | | | | | | | | | |
| 465 | | | | | 470 | | | | | | | | | | | |

( 2 ) INFORMATION FOR SEQ ID NO:8:

( i ) SEQUENCE CHARACTERISTICS:
        ( A ) LENGTH: 472 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Val | Pro | Ala | Gly | Gly | His | Gly | Asp | Val | Gly | Met | His | Val | Lys | Glu |
| 1 | | | | 5 | | | | | 10 | | | | | 15 | |
| Lys | Glu | Lys | Asn | Lys | Asp | Glu | Asn | Lys | Arg | Lys | Asp | Glu | Glu | Arg | Asn |
| | | | 20 | | | | | 25 | | | | | 30 | | |
| Lys | Thr | Gln | Glu | Glu | His | Leu | Lys | Glu | Ile | Met | Lys | His | Ile | Val | Lys |
| | | 35 | | | | | 40 | | | | | 45 | | | |
| Ile | Glu | Val | Lys | Gly | Glu | Glu | Ala | Val | Lys | Lys | Glu | Ala | Ala | Glu | Lys |
| | 50 | | | | | 55 | | | | | 60 | | | | |
| Leu | Leu | Glu | Lys | Val | Pro | Ser | Asp | Val | Leu | Glu | Met | Tyr | Lys | Ala | Ile |
| 65 | | | | | 70 | | | | 75 | | | | | | 80 |
| Gly | Gly | Lys | Ile | Tyr | Ile | Val | Asp | Gly | Asp | Ile | Thr | Lys | His | Ile | Ser |
| | | | | 85 | | | | | 90 | | | | | 95 | |
| Leu | Glu | Ala | Leu | Ser | Glu | Asp | Lys | Lys | Lys | Ile | Lys | Asp | Ile | Tyr | Gly |
| | | | | 100 | | | | 105 | | | | | 110 | | |
| Lys | Asp | Ala | Leu | Leu | His | Glu | His | Tyr | Val | Tyr | Ala | Lys | Glu | Gly | Tyr |
| | | | 115 | | | | 120 | | | | | 125 | | | |
| Glu | Pro | Val | Leu | Val | Ile | Gln | Ser | Ser | Glu | Asp | Tyr | Val | Glu | Asn | Thr |
| | | 130 | | | | | 135 | | | | 140 | | | | |
| Glu | Lys | Ala | Leu | Asn | Val | Tyr | Tyr | Glu | Ile | Gly | Lys | Ile | Leu | Ser | Arg |
| 145 | | | | | 150 | | | | | 155 | | | | | 160 |
| Asp | Ile | Leu | Ser | Lys | Ile | Asn | Gln | Pro | Tyr | Gln | Lys | Phe | Leu | Asp | Val |
| | | | | 165 | | | | | 170 | | | | | 175 | |
| Leu | Asn | Thr | Ile | Lys | Asn | Ala | Ser | Asp | Ser | Asp | Gly | Gln | Asp | Leu | Leu |
| | | | 180 | | | | | 185 | | | | | 190 | | |
| Phe | Thr | Asn | Gln | Leu | Lys | Glu | His | Pro | Thr | Asp | Phe | Ser | Val | Glu | Phe |
| | | 195 | | | | | 200 | | | | | 205 | | | |
| Leu | Glu | Gln | Asn | Ser | Asn | Glu | Val | Gln | Glu | Val | Phe | Ala | Lys | Ala | Phe |
| | 210 | | | | | 215 | | | | | 220 | | | | |
| Ala | Tyr | Tyr | Ile | Glu | Pro | Gln | His | Arg | Asp | Val | Leu | Gln | Leu | Tyr | Ala |
| 225 | | | | | 230 | | | | | 235 | | | | | 240 |
| Pro | Glu | Ala | Phe | Asn | Tyr | Met | Asp | Lys | Phe | Asn | Glu | Gln | Glu | Ile | Asn |
| | | | | 245 | | | | | 250 | | | | | 255 | |
| Leu | Thr | Arg | Ala | Glu | Phe | Leu | Gly | Asp | Gly | Gly | Asp | Val | Ser | Phe | Ser |
| | | | 260 | | | | | 265 | | | | | 270 | | |
| Thr | Arg | Gly | Thr | Gln | Asn | Trp | Thr | Val | Glu | Arg | Leu | Leu | Gln | Ala | His |
| | | 275 | | | | | 280 | | | | | 285 | | | |
| Arg | Gln | Leu | Glu | Glu | Arg | Gly | Tyr | Val | Phe | Val | Gly | Tyr | His | Gly | Thr |
| | 290 | | | | | 295 | | | | | 300 | | | | |
| Phe | Leu | Glu | Ala | Ala | Gln | Ser | Ile | Val | Phe | Gly | Gly | Val | Arg | Ala | Arg |
| 305 | | | | | 310 | | | | | 315 | | | | | 320 |

| | | | | | | | | | | | | | | | |
|---|---|---|---|---|---|---|---|---|---|---|---|---|---|---|---|
| Ser | Gln | Asp | Leu | Asp | Ala | Ile | Trp | Arg | Gly | Phe | Tyr | Ile | Ala | Gly | Asp |
| | | | | 325 | | | | 330 | | | | | | 335 | |
| Pro | Ala | Leu | Ala | Tyr | Gly | Tyr | Ala | Gln | Asp | Gln | Glu | Pro | Asp | Ala | Arg |
| | | | 340 | | | | 345 | | | | | 350 | | | |
| Gly | Arg | Ile | Arg | Asn | Gly | Ala | Leu | Leu | Arg | Val | Tyr | Val | Pro | Arg | Ser |
| | | 355 | | | | | 360 | | | | | 365 | | | |
| Ser | Leu | Pro | Gly | Phe | Tyr | Arg | Thr | Ser | Leu | Thr | Leu | Ala | Ala | Pro | Glu |
| | | 370 | | | | 375 | | | | | 380 | | | | |
| Ala | Ala | Gly | Glu | Val | Glu | Arg | Leu | Ile | Gly | His | Pro | Leu | Pro | Leu | Arg |
| 385 | | | | | 390 | | | | | 395 | | | | | 400 |
| Leu | Asp | Ala | Ile | Thr | Gly | Pro | Glu | Glu | Glu | Gly | Gly | Arg | Leu | Glu | Thr |
| | | | | 405 | | | | | 410 | | | | | 415 | |
| Ile | Leu | Gly | Trp | Pro | Leu | Ala | Glu | Arg | Thr | Val | Val | Ile | Pro | Ser | Ala |
| | | | 420 | | | | | 425 | | | | | 430 | | |
| Ile | Pro | Thr | Asp | Pro | Arg | Asn | Val | Gly | Gly | Asp | Leu | Asp | Pro | Ser | Ser |
| | | 435 | | | | | 440 | | | | | 445 | | | |
| Ile | Pro | Asp | Lys | Glu | Gln | Ala | Ile | Ser | Ala | Leu | Pro | Asp | Tyr | Ala | Ser |
| | | 450 | | | | 455 | | | | | 460 | | | | |
| Gln | Pro | Gly | Lys | Pro | Pro | Arg | Glu | | | | | | | | |
| 465 | | | | | 470 | | | | | | | | | | |

(2) INFORMATION FOR SEQ ID NO:9:

(i) SEQUENCE CHARACTERISTICS:
        (A) LENGTH: 1524 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Bacillus anthracis (ix) FEATURE:
        (A) NAME/KEY: CDS
        (B) LOCATION: 1..1524
        (D) OTHER INFORMATION: /product="LF(1-254)--TR--PE(362-613)"

(xi) SEQUENCE DESCRIPTION: SEQ ID NO:9:

| | | | | | | | | | | | | | | | | |
|---|---|---|---|---|---|---|---|---|---|---|---|---|---|---|---|---|
| GCG | GGC | GGT | CAT | GGT | GAT | GTA | GGT | ATG | CAC | GTA | AAA | GAG | AAA | GAG | AAA | 48 |
| Ala | Gly | Gly | His | Gly | Asp | Val | Gly | Met | His | Val | Lys | Glu | Lys | Glu | Lys | |
| 1 | | | | 5 | | | | | 10 | | | | | 15 | | |
| AAT | AAA | GAT | GAG | AAT | AAG | AGA | AAA | GAT | GAA | GAA | CGA | AAT | AAA | ACA | CAG | 96 |
| Asn | Lys | Asp | Glu | Asn | Lys | Arg | Lys | Asp | Glu | Glu | Arg | Asn | Lys | Thr | Gln | |
| | | | 20 | | | | | 25 | | | | | 30 | | | |
| GAA | GAG | CAT | TTA | AAG | GAA | ATC | ATG | AAA | CAC | ATT | GTA | AAA | ATA | GAA | GTA | 144 |
| Glu | Glu | His | Leu | Lys | Glu | Ile | Met | Lys | His | Ile | Val | Lys | Ile | Glu | Val | |
| | | 35 | | | | | 40 | | | | | 45 | | | | |
| AAA | GGG | GAG | GAA | GCT | GTT | AAA | AAA | GAG | GCA | GCA | GAA | AAG | CTA | CTT | GAG | 192 |
| Lys | Gly | Glu | Glu | Ala | Val | Lys | Lys | Glu | Ala | Ala | Glu | Lys | Leu | Leu | Glu | |
| | 50 | | | | | 55 | | | | | 60 | | | | | |
| AAA | GTA | CCA | TCT | GAT | GTT | TTA | GAG | ATG | TAT | AAA | GCA | ATT | GGA | GGA | AAG | 240 |
| Lys | Val | Pro | Ser | Asp | Val | Leu | Glu | Met | Tyr | Lys | Ala | Ile | Gly | Gly | Lys | |
| 65 | | | | | 70 | | | | | 75 | | | | | 80 | |
| ATA | TAT | ATT | GTG | GAT | GGT | GAT | ATT | ACA | AAA | CAT | ATA | TCT | TTA | GAA | GCA | 288 |
| Ile | Tyr | Ile | Val | Asp | Gly | Asp | Ile | Thr | Lys | His | Ile | Ser | Leu | Glu | Ala | |
| | | | | 85 | | | | | 90 | | | | | 95 | | |
| TTA | TCT | GAA | GAT | AAG | AAA | AAA | ATA | AAA | GAC | ATT | TAT | GGG | AAA | GAT | GCT | 336 |
| Leu | Ser | Glu | Asp | Lys | Lys | Lys | Ile | Lys | Asp | Ile | Tyr | Gly | Lys | Asp | Ala | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 100 |     |     |     |     | 105 |     |     |     |     | 110 |     |      |
| TTA | TTA | CAT | GAA | CAT | TAT | GTA | TAT | GCA | AAA | GAA | GGA | TAT | GAA | CCC | GTA | 384  |
| Leu | Leu | His | Glu | His | Tyr | Val | Tyr | Ala | Lys | Glu | Gly | Tyr | Glu | Pro | Val |      |
|     |     | 115 |     |     |     |     | 120 |     |     |     |     | 125 |     |     |     |      |
| CTT | GTA | ATC | CAA | TCT | TCG | GAA | GAT | TAT | GTA | GAA | AAT | ACT | GAA | AAG | GCA | 432  |
| Leu | Val | Ile | Gln | Ser | Ser | Glu | Asp | Tyr | Val | Glu | Asn | Thr | Glu | Lys | Ala |      |
|     | 130 |     |     |     |     | 135 |     |     |     |     | 140 |     |     |     |     |      |
| CTG | AAC | GTT | TAT | TAT | GAA | ATA | GGT | AAG | ATA | TTA | TCA | AGG | GAT | ATT | TTA | 480  |
| Leu | Asn | Val | Tyr | Tyr | Glu | Ile | Gly | Lys | Ile | Leu | Ser | Arg | Asp | Ile | Leu |      |
| 145 |     |     |     |     | 150 |     |     |     |     | 155 |     |     |     |     | 160 |      |
| AGT | AAA | ATT | AAT | CAA | CCA | TAT | CAG | AAA | TTT | TTA | GAT | GTA | TTA | AAT | ACC | 528  |
| Ser | Lys | Ile | Asn | Gln | Pro | Tyr | Gln | Lys | Phe | Leu | Asp | Val | Leu | Asn | Thr |      |
|     |     |     |     | 165 |     |     |     |     | 170 |     |     |     |     | 175 |     |      |
| ATT | AAA | AAT | GCA | TCT | GAT | TCA | GAT | GGA | CAA | GAT | CTT | TTA | TTT | ACT | AAT | 576  |
| Ile | Lys | Asn | Ala | Ser | Asp | Ser | Asp | Gly | Gln | Asp | Leu | Leu | Phe | Thr | Asn |      |
|     │     |     | 180 |     |     |     |     | 185 |     |     |     |     | 190 |     |     |     |      |
| CAG | CTT | AAG | GAA | CAT | CCC | ACA | GAC | TTT | TCT | GTA | GAA | TTC | TTG | GAA | CAA | 624  |
| Gln | Leu | Lys | Glu | His | Pro | Thr | Asp | Phe | Ser | Val | Glu | Phe | Leu | Glu | Gln |      |
|     |     | 195 |     |     |     |     | 200 |     |     |     |     | 205 |     |     |     |      |
| AAT | AGC | AAT | GAG | GTA | CAA | GAA | GTA | TTT | GCG | AAA | GCT | TTT | GCA | TAT | TAT | 672  |
| Asn | Ser | Asn | Glu | Val | Gln | Glu | Val | Phe | Ala | Lys | Ala | Phe | Ala | Tyr | Tyr |      |
|     | 210 |     |     |     |     | 215 |     |     |     |     | 220 |     |     |     |     |      |
| ATC | GAG | CCA | CAG | CAT | CGT | GAT | GTT | TTA | CAG | CTT | TAT | GCA | CCG | GAA | GCT | 720  |
| Ile | Glu | Pro | Gln | His | Arg | Asp | Val | Leu | Gln | Leu | Tyr | Ala | Pro | Glu | Ala |      |
| 225 |     |     |     |     | 230 |     |     |     |     | 235 |     |     |     |     | 240 |      |
| TTT | AAT | TAC | ATG | GAT | AAA | TTT | AAC | GAA | CAA | GAA | ATA | AAT | CTA | ACG | CGT | 768  |
| Phe | Asn | Tyr | Met | Asp | Lys | Phe | Asn | Glu | Gln | Glu | Ile | Asn | Leu | Thr | Arg |      |
|     |     |     |     | 245 |     |     |     |     | 250 |     |     |     |     | 255 |     |      |
| GCG | GCC | AAC | GCC | GAC | GTG | GTG | AGC | CTG | ACC | TGC | CCG | GTC | GCC | GCC | GGT | 816  |
| Ala | Ala | Asn | Ala | Asp | Val | Val | Ser | Leu | Thr | Cys | Pro | Val | Ala | Ala | Gly |      |
|     |     |     | 260 |     |     |     |     | 265 |     |     |     |     | 270 |     |     |      |
| GAA | TGC | GCG | GGC | CCG | GCG | GAC | AGC | GGC | GAC | GCC | CTG | CTG | GAG | CGC | AAC | 864  |
| Glu | Cys | Ala | Gly | Pro | Ala | Asp | Ser | Gly | Asp | Ala | Leu | Leu | Glu | Arg | Asn |      |
|     | 275 |     |     |     |     | 280 |     |     |     |     | 285 |     |     |     |     |      |
| TAT | CCC | ACT | GGC | GCG | GAG | TTC | CTC | GGC | GAC | GGC | GGC | GAC | GTC | AGC | TTC | 912  |
| Tyr | Pro | Thr | Gly | Ala | Glu | Phe | Leu | Gly | Asp | Gly | Gly | Asp | Val | Ser | Phe |      |
| 290 |     |     |     |     | 295 |     |     |     |     | 300 |     |     |     |     |     |      |
| AGC | ACC | CGC | GGC | ACG | CAG | AAC | TGG | ACG | GTG | GAG | CGG | CTG | CTC | CAG | GCG | 960  |
| Ser | Thr | Arg | Gly | Thr | Gln | Asn | Trp | Thr | Val | Glu | Arg | Leu | Leu | Gln | Ala |      |
| 305 |     |     |     |     | 310 |     |     |     |     | 315 |     |     |     |     | 320 |      |
| CAC | CGC | CAA | CTG | GAG | GAG | CGC | GGC | TAT | GTG | TTC | GTC | GGC | TAC | CAC | GGC | 1008 |
| His | Arg | Gln | Leu | Glu | Glu | Arg | Gly | Tyr | Val | Phe | Val | Gly | Tyr | His | Gly |      |
|     |     |     |     | 325 |     |     |     |     | 330 |     |     |     |     | 335 |     |      |
| ACC | TTC | CTC | GAA | GCG | GCG | CAA | AGC | ATC | GTC | TTC | GGG | GTG | CGC | GCG | | 1056 |
| Thr | Phe | Leu | Glu | Ala | Ala | Gln | Ser | Ile | Val | Phe | Gly | Gly | Val | Arg | Ala |      |
|     |     |     | 340 |     |     |     |     | 345 |     |     |     |     | 350 |     |     |      |
| CGC | AGC | CAG | GAC | CTC | GAC | GCG | ATC | TGG | CGC | GGT | TTC | TAT | ATC | GCC | GGC | 1104 |
| Arg | Ser | Gln | Asp | Leu | Asp | Ala | Ile | Trp | Arg | Gly | Phe | Tyr | Ile | Ala | Gly |      |
|     |     | 355 |     |     |     |     | 360 |     |     |     |     | 365 |     |     |     |      |
| GAT | CCG | GCG | CTG | GCC | TAC | GGC | TAC | GCC | CAG | GAC | CAG | GAA | CCC | GAC | GCA | 1152 |
| Asp | Pro | Ala | Leu | Ala | Tyr | Gly | Tyr | Ala | Gln | Asp | Gln | Glu | Pro | Asp | Ala |      |
|     | 370 |     |     |     |     | 375 |     |     |     |     | 380 |     |     |     |     |      |
| CGC | GGC | CGG | ATC | CGC | AAC | GGT | GCC | CTG | CTG | CGG | GTC | TAT | GTG | CCG | CGC | 1200 |
| Arg | Gly | Arg | Ile | Arg | Asn | Gly | Ala | Leu | Leu | Arg | Val | Tyr | Val | Pro | Arg |      |
| 385 |     |     |     |     | 390 |     |     |     |     | 395 |     |     |     |     | 400 |      |
| TCG | AGC | CTG | CCG | GGC | TTC | TAC | CGC | ACC | AGC | CTG | ACC | CTG | GCC | GCG | CCG | 1248 |
| Ser | Ser | Leu | Pro | Gly | Phe | Tyr | Arg | Thr | Ser | Leu | Thr | Leu | Ala | Ala | Pro |      |
|     |     |     |     | 405 |     |     |     |     | 410 |     |     |     |     | 415 |     |      |
| GAG | GCG | GCG | GGC | GAG | GTC | GAA | CGG | CTG | ATC | GGC | CAT | CCG | CTG | CCG | CTG | 1296 |
| Glu | Ala | Ala | Gly | Glu | Val | Glu | Arg | Leu | Ile | Gly | His | Pro | Leu | Pro | Leu |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 420 |     |     |     |     | 425 |     |     |     |     | 430 |     |     |      |
| CGC | CTG | GAC | GCC | ATC | ACC | GGC | CCC | GAG | GAG | GAA | GGC | GGG | CGC | CTG | GAG | 1344 |
| Arg | Leu | Asp | Ala | Ile | Thr | Gly | Pro | Glu | Glu | Glu | Gly | Gly | Arg | Leu | Glu |      |
|     |     | 435 |     |     |     |     | 440 |     |     |     |     | 445 |     |     |     |      |
| ACC | ATT | CTC | GGC | TGG | CCG | CTG | GCC | GAG | CGC | ACC | GTG | GTG | ATT | CCC | TCG | 1392 |
| Thr | Ile | Leu | Gly | Trp | Pro | Leu | Ala | Glu | Arg | Thr | Val | Val | Ile | Pro | Ser |      |
|     | 450 |     |     |     |     | 455 |     |     |     |     | 460 |     |     |     |     |      |
| GCG | ATC | CCC | ACC | GAC | CCG | CGC | AAC | GTC | GGC | GGC | GAC | CTC | GAC | CCG | TCC | 1440 |
| Ala | Ile | Pro | Thr | Asp | Pro | Arg | Asn | Val | Gly | Gly | Asp | Leu | Asp | Pro | Ser |      |
| 465 |     |     |     |     | 470 |     |     |     |     | 475 |     |     |     |     | 480 |      |
| AGC | ATC | CCC | GAC | AAG | GAA | CAG | GCG | ATC | AGC | GCC | CTG | CCG | GAC | TAC | GCC | 1488 |
| Ser | Ile | Pro | Asp | Lys | Glu | Gln | Ala | Ile | Ser | Ala | Leu | Pro | Asp | Tyr | Ala |      |
|     |     |     |     | 485 |     |     |     |     | 490 |     |     |     |     | 495 |     |      |
| AGC | CAG | CCC | GGC | AAA | CCG | CCG | CGC | GAG | GAC | CTG | AAG |     |     |     |     | 1524 |
| Ser | Gln | Pro | Gly | Lys | Pro | Pro | Arg | Glu | Asp | Leu | Lys |     |     |     |     |      |
|     |     |     | 500 |     |     |     |     | 505 |     |     |     |     |     |     |     |      |

( 2 ) INFORMATION FOR SEQ ID NO:10:

( i ) SEQUENCE CHARACTERISTICS:
        ( A ) LENGTH: 508 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Ala | Gly | Gly | His | Gly | Asp | Val | Gly | Met | His | Val | Lys | Glu | Lys | Glu | Lys |
| 1 | | | | 5 | | | | | 10 | | | | | 15 | |
| Asn | Lys | Asp | Glu | Asn | Lys | Arg | Lys | Asp | Glu | Glu | Arg | Asn | Lys | Thr | Gln |
| | | | 20 | | | | | 25 | | | | | 30 | | |
| Glu | Glu | His | Leu | Lys | Glu | Ile | Met | Lys | His | Ile | Val | Lys | Ile | Glu | Val |
| | | | 35 | | | | | 40 | | | | | 45 | | |
| Lys | Gly | Glu | Glu | Ala | Val | Lys | Lys | Glu | Ala | Ala | Glu | Lys | Leu | Leu | Glu |
| | | 50 | | | | | 55 | | | | | 60 | | | |
| Lys | Val | Pro | Ser | Asp | Val | Leu | Glu | Met | Tyr | Lys | Ala | Ile | Gly | Gly | Lys |
| 65 | | | | | 70 | | | | | 75 | | | | | 80 |
| Ile | Tyr | Ile | Val | Asp | Gly | Asp | Ile | Thr | Lys | His | Ile | Ser | Leu | Glu | Ala |
| | | | | 85 | | | | | 90 | | | | | 95 | |
| Leu | Ser | Glu | Asp | Lys | Lys | Lys | Ile | Lys | Asp | Ile | Tyr | Gly | Lys | Asp | Ala |
| | | | 100 | | | | | 105 | | | | | 110 | | |
| Leu | Leu | His | Glu | His | Tyr | Val | Tyr | Ala | Lys | Glu | Gly | Tyr | Glu | Pro | Val |
| | | 115 | | | | | 120 | | | | | 125 | | | |
| Leu | Val | Ile | Gln | Ser | Ser | Glu | Asp | Tyr | Val | Glu | Asn | Thr | Glu | Lys | Ala |
| | 130 | | | | | 135 | | | | | 140 | | | | |
| Leu | Asn | Val | Tyr | Tyr | Glu | Ile | Gly | Lys | Ile | Leu | Ser | Arg | Asp | Ile | Leu |
| 145 | | | | | 150 | | | | | 155 | | | | | 160 |
| Ser | Lys | Ile | Asn | Gln | Pro | Tyr | Gln | Lys | Phe | Leu | Asp | Val | Leu | Asn | Thr |
| | | | | 165 | | | | | 170 | | | | | 175 | |
| Ile | Lys | Asn | Ala | Ser | Asp | Ser | Asp | Gly | Gln | Asp | Leu | Leu | Phe | Thr | Asn |
| | | | 180 | | | | | 185 | | | | | 190 | | |
| Gln | Leu | Lys | Glu | His | Pro | Thr | Asp | Phe | Ser | Val | Glu | Phe | Leu | Glu | Gln |
| | | 195 | | | | | 200 | | | | | 205 | | | |
| Asn | Ser | Asn | Glu | Val | Gln | Glu | Val | Phe | Ala | Lys | Ala | Phe | Ala | Tyr | Tyr |
| | 210 | | | | | 215 | | | | | 220 | | | | |
| Ile | Glu | Pro | Gln | His | Arg | Asp | Val | Leu | Gln | Leu | Tyr | Ala | Pro | Glu | Ala |
| 225 | | | | | 230 | | | | | 235 | | | | | 240 |
| Phe | Asn | Tyr | Met | Asp | Lys | Phe | Asn | Glu | Gln | Glu | Ile | Asn | Leu | Thr | Arg |

|  |  |  |  |  |  |  | 245 |  |  |  |  | 250 |  |  |  |  | 255 |  |  |
|---|---|---|---|---|---|---|---|---|---|---|---|---|---|---|---|---|---|---|---|
| Ala | Ala | Asn | Ala<br>260 | Asp | Val | Val | Ser | Leu<br>265 | Thr | Cys | Pro | Val | Ala<br>270 | Ala | Gly |
| Glu | Cys | Ala<br>275 | Gly | Pro | Ala | Asp | Ser<br>280 | Gly | Asp | Ala | Leu | Leu<br>285 | Glu | Arg | Asn |
| Tyr | Pro<br>290 | Thr | Gly | Ala | Glu | Phe<br>295 | Leu | Gly | Asp | Gly | Gly<br>300 | Asp | Val | Ser | Phe |
| Ser<br>305 | Thr | Arg | Gly | Thr | Gln<br>310 | Asn | Trp | Thr | Val | Glu<br>315 | Arg | Leu | Leu | Gln | Ala<br>320 |
| His | Arg | Gln | Leu | Glu<br>325 | Glu | Arg | Gly | Tyr | Val<br>330 | Phe | Val | Gly | Tyr | His<br>335 | Gly |
| Thr | Phe | Leu | Glu<br>340 | Ala | Ala | Gln | Ser | Ile<br>345 | Val | Phe | Gly | Gly | Val<br>350 | Arg | Ala |
| Arg | Ser | Gln<br>355 | Asp | Leu | Asp | Ala | Ile<br>360 | Trp | Arg | Gly | Phe | Tyr<br>365 | Ile | Ala | Gly |
| Asp | Pro<br>370 | Ala | Leu | Ala | Tyr | Gly<br>375 | Tyr | Ala | Gln | Asp | Gln<br>380 | Glu | Pro | Asp | Ala |
| Arg<br>385 | Gly | Arg | Ile | Arg | Asn<br>390 | Gly | Ala | Leu | Leu | Arg<br>395 | Val | Tyr | Val | Pro | Arg<br>400 |
| Ser | Ser | Leu | Pro | Gly<br>405 | Phe | Tyr | Arg | Thr | Ser<br>410 | Leu | Thr | Leu | Ala | Ala<br>415 | Pro |
| Glu | Ala | Ala | Gly<br>420 | Glu | Val | Glu | Arg | Leu<br>425 | Ile | Gly | His | Pro | Leu<br>430 | Pro | Leu |
| Arg | Leu | Asp<br>435 | Ala | Ile | Thr | Gly | Pro<br>440 | Glu | Glu | Glu | Gly | Gly<br>445 | Arg | Leu | Glu |
| Thr | Ile<br>450 | Leu | Gly | Trp | Pro | Leu<br>455 | Ala | Glu | Arg | Thr | Val<br>460 | Val | Ile | Pro | Ser |
| Ala<br>465 | Ile | Pro | Thr | Asp | Pro<br>470 | Arg | Asn | Val | Gly | Gly<br>475 | Asp | Leu | Asp | Pro | Ser<br>480 |
| Ser | Ile | Pro | Asp | Lys<br>485 | Glu | Gln | Ala | Ile | Ser<br>490 | Ala | Leu | Pro | Asp | Tyr<br>495 | Ala |
| Ser | Gln | Pro | Gly<br>500 | Lys | Pro | Pro | Arg | Glu<br>505 | Asp | Leu | Lys |  |  |  |  |

( 2 ) INFORMATION FOR SEQ ID NO:11:

( i ) SEQUENCE CHARACTERISTICS:
        ( A ) LENGTH: 2709 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Bacillus anthracis ( i x ) FEATURE:
        ( A ) NAME/KEY: C

|    |    |    |    |    |    |    |    |    |    |    |    |    |    |    |    |      |
|----|----|----|----|----|----|----|----|----|----|----|----|----|----|----|----|------|
| ATG | GTG | GTT | ACC | TCT | TCT | ACT | ACA | GGG | GAT | TTA | TCT | ATT | CCT | AGT | TCT | 144  |
| Met | Val | Val | Thr | Ser | Ser | Thr | Thr | Gly | Asp | Leu | Ser | Ile | Pro | Ser | Ser |      |
|     |     | 35  |     |     |     |     | 40  |     |     |     |     | 45  |     |     |     |      |
| GAG | TTA | GAA | AAT | ATT | CCA | TCG | GAA | AAC | CAA | TAT | TTT | CAA | TCT | GCT | ATT | 192  |
| Glu | Leu | Glu | Asn | Ile | Pro | Ser | Glu | Asn | Gln | Tyr | Phe | Gln | Ser | Ala | Ile |      |
|     |     | 50  |     |     |     |     | 55  |     |     |     |     | 60  |     |     |     |      |
| TGG | TCA | GGA | TTT | ATC | AAA | GTT | AAG | AAG | AGT | GAT | GAA | TAT | ACA | TTT | GCT | 240  |
| Trp | Ser | Gly | Phe | Ile | Lys | Val | Lys | Lys | Ser | Asp | Glu | Tyr | Thr | Phe | Ala |      |
| 65  |     |     |     |     | 70  |     |     |     |     | 75  |     |     |     |     | 80  |      |
| ACT | TCC | GCT | GAT | AAT | CAT | GTA | ACA | ATG | TGG | GTA | GAT | GAC | CAA | GAA | GTG | 288  |
| Thr | Ser | Ala | Asp | Asn | His | Val | Thr | Met | Trp | Val | Asp | Asp | Gln | Glu | Val |      |
|     |     |     |     |     | 85  |     |     |     | 90  |     |     |     |     | 95  |     |      |
| ATT | AAT | AAA | GCT | TCT | AAT | TCT | AAC | AAA | ATC | AGA | TTA | GAA | AAA | GGA | AGA | 336  |
| Ile | Asn | Lys | Ala | Ser | Asn | Ser | Asn | Lys | Ile | Arg | Leu | Glu | Lys | Gly | Arg |      |
|     |     |     |     | 100 |     |     |     |     | 105 |     |     |     |     | 110 |     |      |
| TTA | TAT | CAA | ATA | AAA | ATT | CAA | TAT | CAA | CGA | GAA | AAT | CCT | ACT | GAA | AAA | 384  |
| Leu | Tyr | Gln | Ile | Lys | Ile | Gln | Tyr | Gln | Arg | Glu | Asn | Pro | Thr | Glu | Lys |      |
|     |     |     | 115 |     |     |     |     | 120 |     |     |     |     | 125 |     |     |      |
| GGA | TTG | GAT | TTC | AAG | TTG | TAC | TGG | ACC | GAT | TCT | CAA | AAT | AAA | AAA | GAA | 432  |
| Gly | Leu | Asp | Phe | Lys | Leu | Tyr | Trp | Thr | Asp | Ser | Gln | Asn | Lys | Lys | Glu |      |
|     | 130 |     |     |     |     | 135 |     |     |     |     | 140 |     |     |     |     |      |
| GTG | ATT | TCT | AGT | GAT | AAC | TTA | CAA | TTG | CCA | GAA | TTA | AAA | CAA | AAA | TCT | 480  |
| Val | Ile | Ser | Ser | Asp | Asn | Leu | Gln | Leu | Pro | Glu | Leu | Lys | Gln | Lys | Ser |      |
| 145 |     |     |     |     | 150 |     |     |     |     | 155 |     |     |     |     | 160 |      |
| TCG | AAC | TCA | AGA | AAA | AAG | CGA | AGT | ACA | AGT | GCT | GGA | CCT | ACG | GTT | CCA | 528  |
| Ser | Asn | Ser | Arg | Lys | Lys | Arg | Ser | Thr | Ser | Ala | Gly | Pro | Thr | Val | Pro |      |
|     |     |     |     | 165 |     |     |     |     | 170 |     |     |     |     | 175 |     |      |
| GAC | CGT | GAC | AAT | GAT | GGA | ATC | CCT | GAT | TCA | TTA | GAG | GTA | GAA | GGA | TAT | 576  |
| Asp | Arg | Asp | Asn | Asp | Gly | Ile | Pro | Asp | Ser | Leu | Glu | Val | Glu | Gly | Tyr |      |
|     |     |     |     | 180 |     |     |     |     | 185 |     |     |     |     | 190 |     |      |
| ACG | GTT | GAT | GTC | AAA | AAT | AAA | AGA | ACT | TTT | CTT | TCA | CCA | TGG | ATT | TCT | 624  |
| Thr | Val | Asp | Val | Lys | Asn | Lys | Arg | Thr | Phe | Leu | Ser | Pro | Trp | Ile | Ser |      |
|     |     |     | 195 |     |     |     |     | 200 |     |     |     |     | 205 |     |     |      |
| AAT | ATT | CAT | GAA | AAG | AAA | GGA | TTA | ACC | AAA | TAT | AAA | TCA | TCT | CCT | GAA | 672  |
| Asn | Ile | His | Glu | Lys | Lys | Gly | Leu | Thr | Lys | Tyr | Lys | Ser | Ser | Pro | Glu |      |
|     |     | 210 |     |     |     |     | 215 |     |     |     |     | 220 |     |     |     |      |
| AAA | TGG | AGC | ACG | GCT | TCT | GAT | CCG | TAC | AGT | GAT | TTC | GAA | AAG | GTT | ACA | 720  |
| Lys | Trp | Ser | Thr | Ala | Ser | Asp | Pro | Tyr | Ser | Asp | Phe | Glu | Lys | Val | Thr |      |
| 225 |     |     |     |     | 230 |     |     |     |     | 235 |     |     |     |     | 240 |      |
| GGA | CGG | ATT | GAT | AAG | AAT | GTA | TCA | CCA | GAG | GCA | AGA | CAC | CCC | CTT | GTG | 768  |
| Gly | Arg | Ile | Asp | Lys | Asn | Val | Ser | Pro | Glu | Ala | Arg | His | Pro | Leu | Val |      |
|     |     |     |     | 245 |     |     |     |     | 250 |     |     |     |     | 255 |     |      |
| GCA | GCT | TAT | CCG | ATT | GTA | CAT | GTA | GAT | ATG | GAG | AAT | ATT | ATT | CTC | TCA | 816  |
| Ala | Ala | Tyr | Pro | Ile | Val | His | Val | Asp | Met | Glu | Asn | Ile | Ile | Leu | Ser |      |
|     |     |     | 260 |     |     |     |     | 265 |     |     |     |     | 270 |     |     |      |
| AAA | AAT | GAG | GAT | CAA | TCC | ACA | CAG | AAT | ACT | GAT | AGT | GAA | ACG | AGA | ACA | 864  |
| Lys | Asn | Glu | Asp | Gln | Ser | Thr | Gln | Asn | Thr | Asp | Ser | Glu | Thr | Arg | Thr |      |
|     |     | 275 |     |     |     |     | 280 |     |     |     |     | 285 |     |     |     |      |
| ATA | AGT | AAA | AAT | ACT | TCT | ACA | AGT | AGG | ACA | CAT | ACT | AGT | GAA | GTA | CAT | 912  |
| Ile | Ser | Lys | Asn | Thr | Ser | Thr | Ser | Arg | Thr | His | Thr | Ser | Glu | Val | His |      |
|     |     | 290 |     |     |     |     | 295 |     |     |     |     | 300 |     |     |     |      |
| GGA | AAT | GCA | GAA | GTG | CAT | GCG | TCG | TTC | TTT | GAT | ATT | GGT | GGG | AGT | GTA | 960  |
| Gly | Asn | Ala | Glu | Val | His | Ala | Ser | Phe | Phe | Asp | Ile | Gly | Gly | Ser | Val |      |
| 305 |     |     |     |     | 310 |     |     |     |     | 315 |     |     |     |     | 320 |      |
| TCT | GCA | GGA | TTT | AGT | AAT | TCG | AAT | TCA | AGT | ACG | GTC | GCA | ATT | GAT | CAT | 1008 |
| Ser | Ala | Gly | Phe | Ser | Asn | Ser | Asn | Ser | Ser | Thr | Val | Ala | Ile | Asp | His |      |
|     |     |     |     | 325 |     |     |     |     | 330 |     |     |     |     | 335 |     |      |
| TCA | CTA | TCT | CTA | GCA | GGG | GAA | AGA | ACT | TGG | GCT | GAA | ACA | ATG | GGT | TTA | 1056 |
| Ser | Leu | Ser | Leu | Ala | Gly | Glu | Arg | Thr | Trp | Ala | Glu | Thr | Met | Gly | Leu |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 340 |     |     |     |     | 345 |     |     |     |     | 350 |     |      |
| AAT | ACC | GCT | GAT | ACA | GCA | AGA | TTA | AAT | GCC | AAT | ATT | AGA | TAT | GTA | AAT | 1104 |
| Asn | Thr | Ala | Asp | Thr | Ala | Arg | Leu | Asn | Ala | Asn | Ile | Arg | Tyr | Val | Asn |      |
|     |     |     | 355 |     |     |     |     | 360 |     |     |     |     | 365 |     |     |      |
| ACT | GGG | ACG | GCT | CCA | ATC | TAC | AAC | GTG | TTA | CCA | ACG | ACT | TCG | TTA | GTG | 1152 |
| Thr | Gly | Thr | Ala | Pro | Ile | Tyr | Asn | Val | Leu | Pro | Thr | Thr | Ser | Leu | Val |      |
|     | 370 |     |     |     |     | 375 |     |     |     |     | 380 |     |     |     |     |      |
| TTA | GGA | AAA | AAT | CAA | ACA | CTC | GCG | ACA | ATT | AAA | GCT | AAG | GAA | AAC | CAA | 1200 |
| Leu | Gly | Lys | Asn | Gln | Thr | Leu | Ala | Thr | Ile | Lys | Ala | Lys | Glu | Asn | Gln |      |
| 385 |     |     |     |     | 390 |     |     |     |     | 395 |     |     |     |     | 400 |      |
| TTA | AGT | CAA | ATA | CTT | GCA | CCT | AAT | AAT | TAT | TAT | CCT | TCT | AAA | AAC | TTG | 1248 |
| Leu | Ser | Gln | Ile | Leu | Ala | Pro | Asn | Asn | Tyr | Tyr | Pro | Ser | Lys | Asn | Leu |      |
|     |     |     |     | 405 |     |     |     |     | 410 |     |     |     |     | 415 |     |      |
| GCG | CCA | ATC | GCA | TTA | AAT | GCA | CAA | GAC | GAT | TTC | AGT | TCT | ACT | CCA | ATT | 1296 |
| Ala | Pro | Ile | Ala | Leu | Asn | Ala | Gln | Asp | Asp | Phe | Ser | Ser | Thr | Pro | Ile |      |
|     |     |     | 420 |     |     |     |     | 425 |     |     |     |     | 430 |     |     |      |
| ACA | ATG | AAT | TAC | AAT | CAA | TTT | CTT | GAG | TTA | GAA | AAA | ACG | AAA | CAA | TTA | 1344 |
| Thr | Met | Asn | Tyr | Asn | Gln | Phe | Leu | Glu | Leu | Glu | Lys | Thr | Lys | Gln | Leu |      |
|     |     | 435 |     |     |     |     | 440 |     |     |     |     | 445 |     |     |     |      |
| AGA | TTA | GAT | ACG | GAT | CAA | GTA | TAT | GGG | AAT | ATA | GCA | ACA | TAC | AAT | TTT | 1392 |
| Arg | Leu | Asp | Thr | Asp | Gln | Val | Tyr | Gly | Asn | Ile | Ala | Thr | Tyr | Asn | Phe |      |
|     | 450 |     |     |     |     | 455 |     |     |     |     | 460 |     |     |     |     |      |
| GAA | AAT | GGA | AGA | GTG | AGG | GTG | GAT | ACA | GGC | TCG | AAC | TGG | AGT | GAA | GTG | 1440 |
| Glu | Asn | Gly | Arg | Val | Arg | Val | Asp | Thr | Gly | Ser | Asn | Trp | Ser | Glu | Val |      |
| 465 |     |     |     |     | 470 |     |     |     |     | 475 |     |     |     |     | 480 |      |
| TTA | CCG | CAA | ATT | CAA | GAA | ACA | ACT | GCA | CGT | ATC | ATT | TTT | AAT | GGA | AAA | 1488 |
| Leu | Pro | Gln | Ile | Gln | Glu | Thr | Thr | Ala | Arg | Ile | Ile | Phe | Asn | Gly | Lys |      |
|     |     |     |     | 485 |     |     |     |     | 490 |     |     |     |     | 495 |     |      |
| GAT | TTA | AAT | CTG | GTA | GAA | AGG | CGG | ATA | GCG | GCG | GTT | AAT | CCT | AGT | GAT | 1536 |
| Asp | Leu | Asn | Leu | Val | Glu | Arg | Arg | Ile | Ala | Ala | Val | Asn | Pro | Ser | Asp |      |
|     |     |     | 500 |     |     |     |     | 505 |     |     |     |     | 510 |     |     |      |
| CCA | TTA | GAA | ACG | ACT | AAA | CCG | GAT | ATG | ACA | TTA | AAA | GAA | GCC | CTT | AAA | 1584 |
| Pro | Leu | Glu | Thr | Thr | Lys | Pro | Asp | Met | Thr | Leu | Lys | Glu | Ala | Leu | Lys |      |
|     |     | 515 |     |     |     |     | 520 |     |     |     |     | 525 |     |     |     |      |
| ATA | GCA | TTT | GGA | TTT | AAC | GAA | CCG | AAT | GGA | AAC | TTA | CAA | TAT | CAA | GGG | 1632 |
| Ile | Ala | Phe | Gly | Phe | Asn | Glu | Pro | Asn | Gly | Asn | Leu | Gln | Tyr | Gln | Gly |      |
|     | 530 |     |     |     |     | 535 |     |     |     |     | 540 |     |     |     |     |      |
| AAA | GAC | ATA | ACC | GAA | TTT | GAT | TTT | AAT | TTC | GAT | CAA | CAA | ACA | TCT | CAA | 1680 |
| Lys | Asp | Ile | Thr | Glu | Phe | Asp | Phe | Asn | Phe | Asp | Gln | Gln | Thr | Ser | Gln |      |
| 545 |     |     |     |     | 550 |     |     |     |     | 555 |     |     |     |     | 560 |      |
| AAT | ATC | AAG | AAT | CAG | TTA | GCG | GAA | TTA | AAC | GCA | ACT | AAC | ATA | TAT | ACT | 1728 |
| Asn | Ile | Lys | Asn | Gln | Leu | Ala | Glu | Leu | Asn | Ala | Thr | Asn | Ile | Tyr | Thr |      |
|     |     |     |     | 565 |     |     |     |     | 570 |     |     |     |     | 575 |     |      |
| GTA | TTA | GAT | AAA | ATC | AAA | TTA | AAT | GCA | AAA | ATG | AAT | ATT | TTA | ATA | AGA | 1776 |
| Val | Leu | Asp | Lys | Ile | Lys | Leu | Asn | Ala | Lys | Met | Asn | Ile | Leu | Ile | Arg |      |
|     |     |     | 580 |     |     |     |     | 585 |     |     |     |     | 590 |     |     |      |
| GAT | AAA | CGT | TTT | CAT | TAT | GAT | AGA | AAT | AAC | ATA | GCA | GTT | GGG | GCG | GAT | 1824 |
| Asp | Lys | Arg | Phe | His | Tyr | Asp | Arg | Asn | Asn | Ile | Ala | Val | Gly | Ala | Asp |      |
|     |     | 595 |     |     |     |     | 600 |     |     |     |     | 605 |     |     |     |      |
| GAG | TCA | GTA | GTT | AAG | GAG | GCT | CAT | AGA | GAA | GTA | ATT | AAT | TCG | TCA | ACA | 1872 |
| Glu | Ser | Val | Val | Lys | Glu | Ala | His | Arg | Glu | Val | Ile | Asn | Ser | Ser | Thr |      |
|     | 610 |     |     |     |     | 615 |     |     |     |     | 620 |     |     |     |     |      |
| GAG | GGA | TTA | TTG | TTA | AAT | ATT | GAT | AAG | GAT | ATA | AGA | AAA | ATA | TTA | TCA | 1920 |
| Glu | Gly | Leu | Leu | Leu | Asn | Ile | Asp | Lys | Asp | Ile | Arg | Lys | Ile | Leu | Ser |      |
| 625 |     |     |     |     | 630 |     |     |     |     | 635 |     |     |     |     | 640 |      |
| GGT | TAT | ATT | GTA | GAA | ATT | GAA | GAT | ACT | GAA | GGG | CTT | AAA | GAA | GTT | ATA | 1968 |
| Gly | Tyr | Ile | Val | Glu | Ile | Glu | Asp | Thr | Glu | Gly | Leu | Lys | Glu | Val | Ile |      |
|     |     |     |     | 645 |     |     |     |     | 650 |     |     |     |     | 655 |     |      |
| AAT | GAC | AGA | TAT | GAT | ATG | TTG | AAT | ATT | TCT | AGT | TTA | CGG | CAA | GAT | GGA | 2016 |
| Asn | Asp | Arg | Tyr | Asp | Met | Leu | Asn | Ile | Ser | Ser | Leu | Arg | Gln | Asp | Gly |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     | 660 |     |     |     |     | 665 |     |     |     |     | 670 |      |
| AAA | ACA | TTT | ATA | GAT | TTT | AAA | AAA | TAT | AAT | GAT | AAA | TTA | CCG | TTA | TAT | 2064 |
| Lys | Thr | Phe<br>675 | Ile | Asp | Phe | Lys | Lys | Tyr<br>680 | Asn | Asp | Lys | Leu | Pro<br>685 | Leu | Tyr |      |
| ATA | AGT | AAT | CCC | AAT | TAT | AAG | GTA | AAT | GTA | TAT | GCT | GTT | ACT | AAA | GAA | 2112 |
| Ile | Ser<br>690 | Asn | Pro | Asn | Tyr | Lys<br>695 | Val | Asn | Val | Tyr | Ala | Val<br>700 | Thr | Lys | Glu |      |
| AAC | ACT | ATT | ATT | AAT | CCT | AGT | GAG | AAT | GGG | GAT | ACT | AGT | ACC | AAC | GGG | 2160 |
| Asn<br>705 | Thr | Ile | Ile | Asn | Pro<br>710 | Ser | Glu | Asn | Gly | Asp<br>715 | Thr | Ser | Thr | Asn | Gly<br>720 |      |
| ATC | AAG | AAA | ATT | TTA | AAG | AAA | GTG | GTG | CTG | GGC | AAA | AAA | GGG | GAT | ACA | 2208 |
| Ile | Lys | Lys | Ile | Leu<br>725 | Lys | Lys | Val | Val | Leu<br>730 | Gly | Lys | Lys | Gly | Asp<br>735 | Thr |      |
| GTG | GAA | CTG | ACC | TGT | ACA | GCT | TCC | CAG | AAG | AAG | AGC | ATA | CAA | TTC | CAC | 2256 |
| Val | Glu | Leu | Thr<br>740 | Cys | Thr | Ala | Ser | Gln<br>745 | Lys | Lys | Ser | Ile | Gln<br>750 | Phe | His |      |
| TGG | AAA | AAC | TCC | AAC | CAG | ATA | AAG | ATT | CTG | GGA | AAT | CAG | GGC | TCC | TTC | 2304 |
| Trp | Lys | Asn<br>755 | Ser | Asn | Gln | Ile | Lys<br>760 | Ile | Leu | Gly | Asn | Gln<br>765 | Gly | Ser | Phe |      |
| TTA | ACT | AAA | GGT | CCA | TCC | AAG | CTG | AAT | GAT | CGC | GCT | GAC | TCA | AGA | AGA | 2352 |
| Leu | Thr | Lys<br>770 | Gly | Pro | Ser | Lys<br>775 | Leu | Asn | Asp | Arg | Ala<br>780 | Asp | Ser | Arg | Arg |      |
| AGC | CTT | TGG | GAC | CAA | GGA | AAC | TTC | CCC | CTG | ATC | ATC | AAG | AAT | CTT | AAG | 2400 |
| Ser<br>785 | Leu | Trp | Asp | Gln | Gly<br>790 | Asn | Phe | Pro | Leu | Ile<br>795 | Ile | Lys | Asn | Leu | Lys<br>800 |      |
| ATA | GAA | GAC | TCA | GAT | ACT | TAC | ATC | TGT | GAA | GTG | GAG | GAC | CAG | AAG | GAG | 2448 |
| Ile | Glu | Asp | Ser | Asp<br>805 | Thr | Tyr | Ile | Cys | Glu<br>810 | Val | Glu | Asp | Gln | Lys<br>815 | Glu |      |
| GAG | GTG | CAA | TTG | CTA | GTG | TTC | GGA | TTG | ACT | GCC | AAC | TCT | GAC | ACC | CAC | 2496 |
| Glu | Val | Gln | Leu<br>820 | Leu | Val | Phe | Gly | Leu<br>825 | Thr | Ala | Asn | Ser | Asp<br>830 | Thr | His |      |
| CTG | CTT | CAG | GGG | CAG | AGC | CTG | ACC | CTG | ACC | TTG | GAG | AGC | CCC | CCT | GGT | 2544 |
| Leu | Leu | Gln<br>835 | Gly | Gln | Ser | Leu | Thr<br>840 | Leu | Thr | Leu | Glu | Ser<br>845 | Pro | Pro | Gly |      |
| AGT | AGC | CCC | TCA | GTG | CAA | TGT | AGG | AGT | CCA | AGG | GGT | AAA | AAC | ATA | CAG | 2592 |
| Ser | Ser<br>850 | Pro | Ser | Val | Gln | Cys<br>855 | Arg | Ser | Pro | Arg | Gly<br>860 | Lys | Asn | Ile | Gln |      |
| GGG | GGG | AAG | ACC | CTC | TCC | GTG | TCT | CAG | CTG | GAG | CTC | CAG | GAT | AGT | GGC | 2640 |
| Gly<br>865 | Gly | Lys | Thr | Leu | Ser<br>870 | Val | Ser | Gln | Leu | Glu<br>875 | Leu | Gln | Asp | Ser | Gly<br>880 |      |
| ACC | TGG | ACA | TGC | ACT | GTC | TTG | CAG | AAC | CAG | AAG | AAG | GTG | GAG | TTC | AAA | 2688 |
| Thr | Trp | Thr | Cys | Thr<br>885 | Val | Leu | Gln | Asn | Gln<br>890 | Lys | Lys | Val | Glu | Phe<br>895 | Lys |      |
| ATA | GAC | ATC | GTG | GTG | CTA | GCT |     |     |     |     |     |     |     |     |     | 2709 |
| Ile | Asp | Ile | Val<br>900 | Val | Leu | Ala |     |     |     |     |     |     |     |     |     |      |

( 2 ) INFORMATION FOR SEQ ID NO:12:

( i ) SEQUENCE CHARACTERISTICS:
        ( A ) LENGTH: 903 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Glu | Val | Lys | Gln | Glu | Asn | Arg | Leu | Leu | Asn | Glu | Ser | Glu | Ser | Ser | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gln | Gly | Leu | Leu | Gly | Tyr | Tyr | Phe | Ser | Asp | Leu | Asn | Phe | Gln | Ala | Pro |
|     |     |     | 20  |     |     |     |     | 25  |     |     |     |     | 30  |     |     |

-continued

| | | | | | | | | | | | | | | | |
|---|---|---|---|---|---|---|---|---|---|---|---|---|---|---|---|
| Met | Val | Val 35 | Thr | Ser | Ser | Thr | Thr 40 | Gly | Asp | Leu | Ser | Ile 45 | Pro | Ser | Ser |
| Glu | Leu 50 | Glu | Asn | Ile | Pro | Ser 55 | Glu | Asn | Gln | Tyr | Phe 60 | Gln | Ser | Ala | Ile |
| Trp 65 | Ser | Gly | Phe | Ile | Lys 70 | Val | Lys | Lys | Ser | Asp 75 | Glu | Tyr | Thr | Phe | Ala 80 |
| Thr | Ser | Ala | Asp | Asn 85 | His | Val | Thr | Met | Trp 90 | Val | Asp | Asp | Gln | Glu 95 | Val |
| Ile | Asn | Lys | Ala 100 | Ser | Asn | Ser | Asn | Lys 105 | Ile | Arg | Leu | Glu | Lys 110 | Gly | Arg |
| Leu | Tyr | Gln 115 | Ile | Lys | Ile | Gln | Tyr 120 | Gln | Arg | Glu | Asn | Pro 125 | Thr | Glu | Lys |
| Gly 130 | Leu | Asp | Phe | Lys | Leu | Tyr 135 | Trp | Thr | Asp | Ser | Gln 140 | Asn | Lys | Lys | Glu |
| Val 145 | Ile | Ser | Ser | Asp | Asn 150 | Leu | Gln | Leu | Pro | Glu 155 | Leu | Lys | Gln | Lys | Ser 160 |
| Ser | Asn | Ser | Arg | Lys 165 | Lys | Arg | Ser | Thr | Ser 170 | Ala | Gly | Pro | Thr | Val 175 | Pro |
| Asp | Arg | Asp | Asn 180 | Asp | Gly | Ile | Pro | Asp 185 | Ser | Leu | Glu | Val | Glu 190 | Gly | Tyr |
| Thr | Val | Asp 195 | Val | Lys | Asn | Lys | Arg 200 | Thr | Phe | Leu | Ser | Pro 205 | Trp | Ile | Ser |
| Asn | Ile 210 | His | Glu | Lys | Lys | Gly 215 | Leu | Thr | Lys | Tyr | Lys 220 | Ser | Ser | Pro | Glu |
| Lys 225 | Trp | Ser | Thr | Ala | Ser 230 | Asp | Pro | Tyr | Ser | Asp 235 | Phe | Glu | Lys | Val | Thr 240 |
| Gly | Arg | Ile | Asp | Lys 245 | Asn | Val | Ser | Pro | Glu 250 | Ala | Arg | His | Pro | Leu 255 | Val |
| Ala | Ala | Tyr | Pro 260 | Ile | Val | His | Val | Asp 265 | Met | Glu | Asn | Ile | Ile 270 | Leu | Ser |
| Lys | Asn | Glu 275 | Asp | Gln | Ser | Thr | Gln 280 | Asn | Thr | Asp | Ser | Glu 285 | Thr | Arg | Thr |
| Ile | Ser 290 | Lys | Asn | Thr | Ser | Thr 295 | Ser | Arg | Thr | His | Thr 300 | Ser | Glu | Val | His |
| Gly 305 | Asn | Ala | Glu | Val | His 310 | Ala | Ser | Phe | Phe | Asp 315 | Ile | Gly | Gly | Ser | Val 320 |
| Ser | Ala | Gly | Phe | Ser 325 | Asn | Ser | Asn | Ser | Ser 330 | Thr | Val | Ala | Ile | Asp 335 | His |
| Ser | Leu | Ser | Leu 340 | Ala | Gly | Glu | Arg | Thr 345 | Trp | Ala | Glu | Thr | Met 350 | Gly | Leu |
| Asn | Thr | Ala 355 | Asp | Thr | Ala | Arg | Leu 360 | Asn | Ala | Asn | Ile | Arg 365 | Tyr | Val | Asn |
| Thr | Gly 370 | Thr | Ala | Pro | Ile | Tyr 375 | Asn | Val | Leu | Pro | Thr 380 | Thr | Ser | Leu | Val |
| Leu 385 | Gly | Lys | Asn | Gln | Thr 390 | Leu | Ala | Thr | Ile | Lys 395 | Ala | Lys | Glu | Asn | Gln 400 |
| Leu | Ser | Gln | Ile | Leu 405 | Ala | Pro | Asn | Asn | Tyr 410 | Tyr | Pro | Ser | Lys | Asn 415 | Leu |
| Ala | Pro | Ile | Ala 420 | Leu | Asn | Ala | Gln | Asp 425 | Asp | Phe | Ser | Ser | Thr 430 | Pro | Ile |
| Thr | Met | Asn 435 | Tyr | Asn | Gln | Phe | Leu 440 | Glu | Leu | Glu | Lys | Thr 445 | Lys | Gln | Leu |
| Arg | Leu 450 | Asp | Thr | Asp | Gln | Val 455 | Tyr | Gly | Asn | Ile | Ala 460 | Thr | Tyr | Asn | Phe |

```
Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Lys Lys Val Val Leu Gly Lys Lys Gly Asp Thr
                725                 730                 735

Val Glu Leu Thr Cys Thr Ala Ser Gln Lys Lys Ser Ile Gln Phe His
            740                 745                 750

Trp Lys Asn Ser Asn Gln Ile Lys Ile Leu Gly Asn Gln Gly Ser Phe
        755                 760                 765

Leu Thr Lys Gly Pro Ser Lys Leu Asn Asp Arg Ala Asp Ser Arg Arg
    770                 775                 780

Ser Leu Trp Asp Gln Gly Asn Phe Pro Leu Ile Ile Lys Asn Leu Lys
785                 790                 795                 800

Ile Glu Asp Ser Asp Thr Tyr Ile Cys Glu Val Glu Asp Gln Lys Glu
                805                 810                 815

Glu Val Gln Leu Leu Val Phe Gly Leu Thr Ala Asn Ser Asp Thr His
            820                 825                 830

Leu Leu Gln Gly Gln Ser Leu Thr Leu Thr Leu Glu Ser Pro Pro Gly
        835                 840                 845

Ser Ser Pro Ser Val Gln Cys Arg Ser Pro Arg Gly Lys Asn Ile Gln
    850                 855                 860

Gly Gly Lys Thr Leu Ser Val Ser Gln Leu Glu Leu Gln Asp Ser Gly
865                 870                 875                 880

Thr Trp Thr Cys Thr Val Leu Gln Asn Gln Lys Lys Val Glu Phe Lys
```

885                         890                          895

Ile Asp Ile Val Val Leu Ala
              900

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Bacillus anthracis ( i x ) FEATURE:
        ( A ) NAME/KEY: Peptide
        ( B ) LOCATION: 1..8
        ( D ) OTHER INFORMATION: /label=PAHIV ( x i ) SEQUENCE DESCRIPTION: SEQ ID NO:13:

Ser Gln Asn Tyr Pro Val Val Gln
 1               5

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Bacillus anthracis ( i x ) FEATURE:
        ( A ) NAME/KEY: Peptide
        ( B ) LOCATION: 1..12
        ( D ) OTHER INFORMATION: /label=PAHIV-1

( x i ) SEQUENCE DESCRIPTION: SEQ ID NO:14:

Gln Val Ser Gln Asn Tyr Pro Ile Val Gln Asn Ile
 1               5                   10

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Bacillus anthracis ( i x ) FEATURE:

(A) NAME/KEY: Peptide
(B) LOCATION: 1..12
(D) OTHER INFORMATION: /label=PAHIV-2

(xi) SEQUENCE DESC ( i x ) FEATURE:
  ( A ) NAME/KEY: CDS
  ( B ) LOCATION: 3..44
  ( D ) OTHER INFORMATION: /product="Primer 1A"

( x i ) SEQUENCE DESCRIPTION: SEQ ID NO:18:

```
CG CAA GTA TCA CAA AAT TAT CCG ATC GTG CAA AAC ATA CTG CAG     44
   Gln Val Ser Gln Asn Tyr Pro Ile Val Gln Asn Ile Leu Gln
    1           5                  10

G                                                              45
```

( 2 ) INFORMATION FOR SEQ ID NO:19:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: protein ( x i ) SEQUENCE DESCRIPTION: SEQ ID NO:19:

```
Gln Val Ser Gln Asn Tyr Pro Ile Val Gln Asn Ile Leu Gln
 1           5                  10
```

( 2 ) INFORMATION FOR SEQ ID NO:20:

( i ) SEQUENCE CHARACTERISTICS:
  ( A ) LENGTH: 46 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
  ( A ) ORGANISM: Bacillus anthracis ( i x ) FEATURE:
  ( A ) NAME/KEY: misc_feature
  ( B ) LOCATION: 1..46
  ( D ) OTHER INFORMATION: /product="Primer 1B"

( x i ) SEQUENCE DESCRIPTION: SEQ ID NO:20:

```
GTTCCTGCAG TATGTTTTGC ACGATCGGAT AATTTGTGA TACTTG              46
```

( 2 ) INFORMATION FOR SEQ ID NO:21:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( v i ) ORIGINAL SOURCE:
  ( A ) ORGANISM: Bacillus anthracis ( i x ) FEATURE:
  ( A ) NAME/KEY: CDS
  ( B ) LOCATION: 3..44
  ( D ) OTHER INFORMATION: /product="Primer 2A"

( x i ) SEQUENCE DESCRIPTION: SEQ ID NO:21:

```
CG AAC ACT GCC ACT ATC ATG ATG CAA CGT GGT AAT TTT CTG CAG     44
```

```
Asn  Thr  Ala  Thr  Ile  Met  Met  Gln  Arg  Gly  Asn  Phe  Leu  Gln
 1              5                        10
```

G                                                                                                45

( 2 ) INFORMATION FOR SEQ ID NO:22:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Asn  Thr  Ala  Thr  Ile  Met  Met  Gln  Arg  Gly  Asn  Phe  Leu  Gln
 1              5                        10
```

( 2 ) INFORMATION FOR SEQ ID NO:23:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: Bacillus anthracis &n (A) LENGTH: 14 amino acids
(B) TYPE: amino acid
(D) TOPOLOGY: linear (ii) MOLECULE TYPE: protein (xi) SEQUENCE DESCRIPTION: SEQ ID NO:25:

Thr Val Ser Phe Asn Phe Pro Gln Ile Thr Leu Trp Leu Gln
 1               5                  10

(2) INFORMATION FOR SEQ ID NO:26:

(i) SEQUENCE CHARACTERISTICS:
      (A) LENGTH: 46 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (vi) ORIGINAL SOURCE:
      (A) ORGANISM: Bacillus anthracis (ix) FEATURE:
      (A) NAME/KEY: misc_feature
      (B) LOCATION: 1..46
      (D) OTHER INFORMATION: /product="Primer 3B"

(xi) SEQUENCE DESCRIPTION: SEQ ID NO:26:

GTCCCTGCAG CCAAAGCGTG ATTTGCGGGA AGTTAAAAGA GACAGT      46

(2) INFORMATION FOR SEQ ID NO:27:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Bacillus anthracis -continued 1 5 10 15

( 2 ) INFORMATION FOR SEQ ID NO:29:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
( A ) ORGANISM: Bacillus anthracis ( i x ) FEATURE:
( A ) NAME/KEY: misc_feature
( B ) LOCATION: 1..49
( D ) OTHER INFORMATION: /product="Primer 4B"

( x i ) SEQUENCE DESCRIPTION: SEQ ID NO:29:

GTCCCTGCAG ACCTCCCATG ACGATCGGGA AGTTAAAGGC AGAACCGCC 49

( 2 ) INFORMATION FOR SEQ ID NO:30:

( i ) SEQUENCE CHARACTERISTICS:
( A ) LENGTH: 2160 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Bacillus anthracis ( i x ) FEATURE:
( A ) NAME/KEY: CDS
( B ) LOCATION: 1..2157
( D ) OTHER INFORMATION: /product="PAHIV#2"

( x i ) SEQUENCE DESCRIPTION: SEQ ID NO:30:

GAA GTT AAA CAG GAG AAC CGG TTA TTA AAT GAA TCA GAA TCA AGT TCC 48
Glu Val Lys Gln Glu Asn Arg Leu Leu Asn Glu Ser Glu Ser Ser Ser
1 5 10 15

CAG GGG TTA CTA GGA TAC TAT TTT AGT GAT TTG AAT TTT CAA GCA CCC 96
Gln Gly Leu Leu Gly Tyr Tyr Phe Ser Asp Leu Asn Phe Gln Ala Pro
20 25 30

ATG GTG GTT ACC TCT TCT ACT ACA GGG GAT TTA TCT ATT CCT AGT TCT 144
Met Val Val Thr Ser Ser Thr Thr Gly Asp Leu Ser Ile Pro Ser Ser
35 40 45

GAG TTA GAA AAT ATT CCA TCG GAA AAC CAA TAT TTT CAA TCT GCT ATT 192
Glu Leu Glu Asn Ile Pro Ser Glu Asn Gln Tyr Phe Gln Ser Ala Ile
50 55 60

TGG TCA GGA TTT ATC AAA GTT AAG AAG AGT GAT GAA TAT ACA TTT GCT 240
Trp Ser Gly Phe Ile Lys Val Lys Lys Ser Asp Glu Tyr Thr Phe Ala
65 70 75 80

ACT TCC GCT GAT AAT CAT GTA ACA ATG TGG GTA GAT GAC CAA GAA GTG 288
Thr Ser Ala Asp Asn His Val Thr Met Trp Val Asp Asp Gln Glu Val
85 90 95

ATT AAT AAA GCT TCT AAT TCT AAC AAA ATC AGA TTA GAA AAA GGA AGA 336
Ile Asn Lys Ala Ser Asn Ser Asn Lys Ile Arg Leu Glu Lys Gly Arg
100 105 110

| | | | | | | | | | | | | | | | | |
|---|---|---|---|---|---|---|---|---|---|---|---|---|---|---|---|---|
| TTA | TAT | CAA | ATA | AAA | ATT | CAA | TAT | CAA | CGA | GAA | AAT | CCT | ACT | GAA | AAA | 384 |
| Leu | Tyr | Gln | Ile | Lys | Ile | Gln | Tyr | Gln | Arg | Glu | Asn | Pro | Thr | Glu | Lys | |
| | | 115 | | | | 120 | | | | | 125 | | | | | |
| GGA | TTG | GAT | TTC | AAG | TTG | TAC | TGG | ACC | GAT | TCT | CAA | AAT | AAA | AAA | GAA | 432 |
| Gly | Leu | Asp | Phe | Lys | Leu | Tyr | Trp | Thr | Asp | Ser | Gln | Asn | Lys | Lys | Glu | |
| | 130 | | | | 135 | | | | | 140 | | | | | | |
| GTG | ATT | TCT | AGT | GAT | AAC | TTA | CAA | TTG | CCA | GAA | TTA | AAA | CAA | AAA | TCT | 480 |
| Val | Ile | Ser | Ser | Asp | Asn | Leu | Gln | Leu | Pro | Glu | Leu | Lys | Gln | Lys | Ser | |
| 145 | | | | | 150 | | | | | 155 | | | | | 160 | |
| TCG | AAC | ACT | GCC | ACT | ATC | ATG | ATG | CAA | CGT | GGT | AAT | TTT | CTG | CAG | GGA | 528 |
| Ser | Asn | Thr | Ala | Thr | Ile | Met | Met | Gln | Arg | Gly | Asn | Phe | Leu | Gln | Gly | |
| | | | | 165 | | | | | 170 | | | | | 175 | | |
| CCT | ACG | GTT | CCA | GAC | CGT | GAC | AAT | GAT | GGA | ATC | CCT | GAT | TCA | TTA | GAG | 576 |
| Pro | Thr | Val | Pro | Asp | Arg | Asp | Asn | Asp | Gly | Ile | Pro | Asp | Ser | Leu | Glu | |
| | | | 180 | | | | | 185 | | | | | 190 | | | |
| GTA | GAA | GGA | TAT | ACG | GTT | GAT | GTC | AAA | AAT | AAA | AGA | ACT | TTT | CTT | TCA | 624 |
| Val | Glu | Gly | Tyr | Thr | Val | Asp | Val | Lys | Asn | Lys | Arg | Thr | Phe | Leu | Ser | |
| | | 195 | | | | | 200 | | | | | 205 | | | | |
| CCA | TGG | ATT | TCT | AAT | ATT | CAT | GAA | AAG | AAA | GGA | TTA | ACC | AAA | TAT | AAA | 672 |
| Pro | Trp | Ile | Ser | Asn | Ile | His | Glu | Lys | Lys | Gly | Leu | Thr | Lys | Tyr | Lys | |
| | 210 | | | | | 215 | | | | | 220 | | | | | |
| TCA | TCT | CCT | GAA | AAA | TGG | AGC | ACG | GCT | TCT | GAT | CCG | TAC | AGT | GAT | TTC | 720 |
| Ser | Ser | Pro | Glu | Lys | Trp | Ser | Thr | Ala | Ser | Asp | Pro | Tyr | Ser | Asp | Phe | |
| 225 | | | | | 230 | | | | | 235 | | | | | 240 | |
| GAA | AAG | GTT | ACA | GGA | CGG | ATT | GAT | AAG | AAT | GTA | TCA | CCA | GAG | GCA | AGA | 768 |
| Glu | Lys | Val | Thr | Gly | Arg | Ile | Asp | Lys | Asn | Val | Ser | Pro | Glu | Ala | Arg | |
| | | | | 245 | | | | | 250 | | | | | 255 | | |
| CAC | CCC | CTT | GTG | GCA | GCT | TAT | CCG | ATT | GTA | CAT | GTA | GAT | ATG | GAG | AAT | 816 |
| His | Pro | Leu | Val | Ala | Ala | Tyr | Pro | Ile | Val | His | Val | Asp | Met | Glu | Asn | |
| | | | 260 | | | | | 265 | | | | | 270 | | | |
| ATT | ATT | CTC | TCA | AAA | AAT | GAG | GAT | CAA | TCC | ACA | CAG | AAT | ACT | GAT | AGT | 864 |
| Ile | Ile | Leu | Ser | Lys | Asn | Glu | Asp | Gln | Ser | Thr | Gln | Asn | Thr | Asp | Ser | |
| | | 275 | | | | | 280 | | | | | 285 | | | | |
| GAA | ACG | AGA | ACA | ATA | AGT | AAA | AAT | ACT | TCT | ACA | AGT | AGG | ACA | CAT | ACT | 912 |
| Glu | Thr | Arg | Thr | Ile | Ser | Lys | Asn | Thr | Ser | Thr | Ser | Arg | Thr | His | Thr | |
| 290 | | | | | 295 | | | | | 300 | | | | | | |
| AGT | GAA | GTA | CAT | GGA | AAT | GCA | GAA | GTG | CAT | GCG | TCG | TTC | TTT | GAT | ATT | 960 |
| Ser | Glu | Val | His | Gly | Asn | Ala | Glu | Val | His | Ala | Ser | Phe | Phe | Asp | Ile | |
| 305 | | | | | 310 | | | | | 315 | | | | | 320 | |
| GGT | GGG | AGT | GTA | TCT | GCA | GGA | TTT | AGT | AAT | TCG | AAT | TCA | AGT | ACG | GTC | 1008 |
| Gly | Gly | Ser | Val | Ser | Ala | Gly | Phe | Ser | Asn | Ser | Asn | Ser | Ser | Thr | Val | |
| | | | | 325 | | | | | 330 | | | | | 335 | | |
| GCA | ATT | GAT | CAT | TCA | CTA | TCT | CTA | GCA | GGG | GAA | AGA | ACT | TGG | GCT | GAA | 1056 |
| Ala | Ile | Asp | His | Ser | Leu | Ser | Leu | Ala | Gly | Glu | Arg | Thr | Trp | Ala | Glu | |
| | | | 340 | | | | | 345 | | | | | 350 | | | |
| ACA | ATG | GGT | TTA | AAT | ACC | GCT | GAT | ACA | GCA | AGA | TTA | AAT | GCC | AAT | ATT | 1104 |
| Thr | Met | Gly | Leu | Asn | Thr | Ala | Asp | Thr | Ala | Arg | Leu | Asn | Ala | Asn | Ile | |
| | | 355 | | | | | 360 | | | | | 365 | | | | |
| AGA | TAT | GTA | AAT | ACT | GGG | ACG | GCT | CCA | ATC | TAC | AAC | GTG | TTA | CCA | ACG | 1152 |
| Arg | Tyr | Val | Asn | Thr | Gly | Thr | Ala | Pro | Ile | Tyr | Asn | Val | Leu | Pro | Thr | |
| | 370 | | | | | 375 | | | | | 380 | | | | | |
| ACT | TCG | TTA | GTG | TTA | GGA | AAA | AAT | CAA | ACA | CTC | GCG | ACA | ATT | AAA | GCT | 1200 |
| Thr | Ser | Leu | Val | Leu | Gly | Lys | Asn | Gln | Thr | Leu | Ala | Thr | Ile | Lys | Ala | |
| 385 | | | | | 390 | | | | | 395 | | | | | 400 | |
| AAG | GAA | AAC | CAA | TTA | AGT | CAA | ATA | CTT | GCA | CCT | AAT | AAT | TAT | TAT | CCT | 1248 |
| Lys | Glu | Asn | Gln | Leu | Ser | Gln | Ile | Leu | Ala | Pro | Asn | Asn | Tyr | Tyr | Pro | |
| | | | | 405 | | | | | 410 | | | | | 415 | | |
| TCT | AAA | AAC | TTG | GCG | CCA | ATC | GCA | TTA | AAT | GCA | CAA | GAC | GAT | TTC | AGT | 1296 |
| Ser | Lys | Asn | Leu | Ala | Pro | Ile | Ala | Leu | Asn | Ala | Gln | Asp | Asp | Phe | Ser | |
| | | | 420 | | | | | 425 | | | | | 430 | | | |

| | | | | | | | | | | | | | | | | |
|---|---|---|---|---|---|---|---|---|---|---|---|---|---|---|---|---|
| TCT | ACT | CCA | ATT | ACA | ATG | AAT | TAC | GGG | AAT | ATA | GCA | ACA | TAC | AAT | TTT | 1344 |
| Ser | Thr | Pro 435 | Ile | Thr | Met | Asn | Tyr 440 | Gly | Asn | Ile | Ala | Thr 445 | Tyr | Asn | Phe | |
| GAA | AAT | GGA | AGA | GTG | AGG | GTG | GAT | ACA | GGC | TCG | AAC | TGG | AGT | GAA | GTG | 1392 |
| Glu | Asn 450 | Gly | Arg | Val | Arg | Val 455 | Asp | Thr | Gly | Ser | Asn 460 | Trp | Ser | Glu | Val | |
| TTA | CCG | CAA | ATT | CAA | GAA | ACA | ACT | GCA | CGT | ATC | ATT | TTT | AAT | GGA | AAA | 1440 |
| Leu 465 | Pro | Gln | Ile | Gln | Glu 470 | Thr | Thr | Ala | Arg | Ile 475 | Ile | Phe | Asn | Gly | Lys 480 | |
| GAT | TTA | AAT | CTG | GTA | GAA | AGG | CGG | ATA | GCG | GCG | GTT | AAT | CCT | AGT | GAT | 1488 |
| Asp | Leu | Asn | Leu | Val 485 | Glu | Arg | Arg | Ile | Ala 490 | Ala | Val | Asn | Pro | Ser 495 | Asp | |
| CCA | TTA | GAA | ACG | ACT | AAA | CCG | GAT | ATG | ACA | TTA | AAA | GAA | GCC | CTT | AAA | 1536 |
| Pro | Leu | Glu | Thr 500 | Thr | Lys | Pro | Asp | Met 505 | Thr | Leu | Lys | Glu | Ala 510 | Leu | Lys | |
| ATA | GCA | TTT | GGA | TTT | AAC | GAA | CCG | AAT | GGA | AAC | TTA | CAA | TAT | CAA | GGG | 1584 |
| Ile | Ala | Phe 515 | Gly | Phe | Asn | Glu | Pro 520 | Asn | Gly | Asn | Leu | Gln 525 | Tyr | Gln | Gly | |
| AAA | GAC | ATA | ACC | GAA | TTT | GAT | TTT | AAT | TTC | GAT | CAA | CAA | ACA | TCT | CAA | 1632 |
| Lys | Asp 530 | Ile | Thr | Glu | Phe | Asp 535 | Phe | Asn | Phe | Asp | Gln 540 | Gln | Thr | Ser | Gln | |
| AAT | ATC | AAG | AAT | CAG | TTA | GCG | GAA | TTA | AAC | GCA | ACT | AAC | ATA | TAT | ACT | 1680 |
| Asn 545 | Ile | Lys | Asn | Gln | Leu 550 | Ala | Glu | Leu | Asn | Ala 555 | Thr | Asn | Ile | Tyr | Thr 560 | |
| GTA | TTA | GAT | AAA | ATC | AAA | TTA | AAT | GCA | AAA | ATG | AAT | ATT | TTA | ATA | AGA | 1728 |
| Val | Leu | Asp | Lys | Ile 565 | Lys | Leu | Asn | Ala | Lys 570 | Met | Asn | Ile | Leu | Ile 575 | Arg | |
| GAT | AAA | CGT | TTT | CAT | TAT | GAT | AGA | AAT | AAC | ATA | GCA | GTT | GGG | GCG | GAT | 1776 |
| Asp | Lys | Arg | Phe 580 | His | Tyr | Asp | Arg | Asn 585 | Asn | Ile | Ala | Val | Gly 590 | Ala | Asp | |
| GAG | TCA | GTA | GTT | AAG | GAG | GCT | CAT | AGA | GAA | GTA | ATT | AAT | TCG | TCA | ACA | 1824 |
| Glu | Ser | Val 595 | Val | Lys | Glu | Ala | His 600 | Arg | Glu | Val | Ile | Asn 605 | Ser | Ser | Thr | |
| GAG | GGA | TTA | TTG | TTA | AAT | ATT | GAT | AAG | GAT | ATA | AGA | AAA | ATA | TTA | TCA | 1872 |
| Glu | Gly | Leu 610 | Leu | Leu | Asn | Ile | Asp 615 | Lys | Asp | Ile | Arg | Lys 620 | Ile | Leu | Ser | |
| GGT | TAT | ATT | GTA | GAA | ATT | GAA | GAT | ACT | GAA | GGG | CTT | AAA | GAA | GTT | ATA | 1920 |
| Gly 625 | Tyr | Ile | Val | Glu | Ile 630 | Glu | Asp | Thr | Glu | Gly 635 | Leu | Lys | Glu | Val | Ile 640 | |
| AAT | GAC | AGA | TAT | GAT | ATG | TTG | AAT | ATT | TCT | AGT | TTA | CGG | CAA | GAT | GGA | 1968 |
| Asn | Asp | Arg | Tyr | Asp 645 | Met | Leu | Asn | Ile | Ser 650 | Ser | Leu | Arg | Gln | Asp 655 | Gly | |
| AAA | ACA | TTT | ATA | GAT | TTT | AAA | AAA | TAT | AAT | GAT | AAA | TTA | CCG | TTA | TAT | 2016 |
| Lys | Thr | Phe | Ile 660 | Asp | Phe | Lys | Lys | Tyr 665 | Asn | Asp | Lys | Leu | Pro 670 | Leu | Tyr | |
| ATA | AGT | AAT | CCC | AAT | TAT | AAG | GTA | AAT | GTA | TAT | GCT | GTT | ACT | AAA | GAA | 2064 |
| Ile | Ser | Asn 675 | Pro | Asn | Tyr | Lys | Val 680 | Asn | Val | Tyr | Ala | Val 685 | Thr | Lys | Glu | |
| AAC | ACT | ATT | ATT | AAT | CCT | AGT | GAG | AAT | GGG | GAT | ACT | AGT | ACC | AAC | GGG | 2112 |
| Asn | Thr | Ile 690 | Ile | Asn | Pro | Ser 695 | Glu | Asn | Gly | Asp | Thr 700 | Ser | Thr | Asn | Gly | |
| ATC | AAG | AAA | ATT | TTA | ATC | TTT | TCT | AAA | AAA | GGC | TAT | GAG | ATA | GGA | | 2157 |
| Ile 705 | Lys | Lys | Ile | Leu | Ile 710 | Phe | Ser | Lys | Lys | Gly 715 | Tyr | Glu | Ile | Gly | | |
| TAA | | | | | | | | | | | | | | | | 2160 |

( 2 ) INFORMATION FOR SEQ ID NO:31:

( i ) SEQUENCE CHARACTERISTICS:

( A ) LENGTH: 719 amino acids ( B ) TYPE: amino acid (D) TOPOLOGY: linear (ii) MOLECULE TYPE: protein (xi) SEQUENCE DESCRIPTION: SEQ ID NO:31:

| Glu | Val | Lys | Gln | Glu | Asn | Arg | Leu | Leu | Asn | Glu | Ser | Glu | Ser | Ser | Ser |
|---|---|---|---|---|---|---|---|---|---|---|---|---|---|---|---|
| 1 | | | | 5 | | | | | 10 | | | | | 15 | |

| Gln | Gly | Leu | Leu | Gly | Tyr | Tyr | Phe | Ser | Asp | Leu | Asn | Phe | Gln | Ala | Pro |
|---|---|---|---|---|---|---|---|---|---|---|---|---|---|---|---|
| | | | 20 | | | | | 25 | | | | | 30 | | |

| Met | Val | Val | Thr | Ser | Ser | Thr | Thr | Gly | Asp | Leu | Ser | Ile | Pro | Ser | Ser |
|---|---|---|---|---|---|---|---|---|---|---|---|---|---|---|---|
| | | | 35 | | | | 40 | | | | | 45 | | | |

| Glu | Leu | Glu | Asn | Ile | Pro | Ser | Glu | Asn | Gln | Tyr | Phe | Gln | Ser | Ala | Ile |
|---|---|---|---|---|---|---|---|---|---|---|---|---|---|---|---|
| | 50 | | | | | 55 | | | | | 60 | | | | |

| Trp | Ser | Gly | Phe | Ile | Lys | Val | Lys | Lys | Ser | Asp | Glu | Tyr | Thr | Phe | Ala |
|---|---|---|---|---|---|---|---|---|---|---|---|---|---|---|---|
| 65 | | | | | 70 | | | | | 75 | | | | | 80 |

| Thr | Ser | Ala | Asp | Asn | His | Val | Thr | Met | Trp | Val | Asp | Asp | Gln | Glu | Val |
|---|---|---|---|---|---|---|---|---|---|---|---|---|---|---|---|
| | | | | 85 | | | | | 90 | | | | | 95 | |

| Ile | Asn | Lys | Ala | Ser | Asn | Ser | Asn | Lys | Ile | Arg | Leu | Glu | Lys | Gly | Arg |
|---|---|---|---|---|---|---|---|---|---|---|---|---|---|---|---|
| | | | 100 | | | | | 105 | | | | | 110 | | |

| Leu | Tyr | Gln | Ile | Lys | Ile | Gln | Tyr | Gln | Arg | Glu | Asn | Pro | Thr | Glu | Lys |
|---|---|---|---|---|---|---|---|---|---|---|---|---|---|---|---|
| | | 115 | | | | | 120 | | | | | 125 | | | |

| Gly | Leu | Asp | Phe | Lys | Leu | Tyr | Trp | Thr | Asp | Ser | Gln | Asn | Lys | Lys | Glu |
|---|---|---|---|---|---|---|---|---|---|---|---|---|---|---|---|
| | 130 | | | | | 135 | | | | | 140 | | | | |

| Val | Ile | Ser | Ser | Asp | Asn | Leu | Gln | Leu | Pro | Glu | Leu | Lys | Gln | Lys | Ser |
|---|---|---|---|---|---|---|---|---|---|---|---|---|---|---|---|
| 145 | | | | | 150 | | | | | 155 | | | | | 160 |

| Ser | Asn | Thr | Ala | Thr | Ile | Met | Met | Gln | Arg | Gly | Asn | Phe | Leu | Gln | Gly |
|---|---|---|---|---|---|---|---|---|---|---|---|---|---|---|---|
| | | | | 165 | | | | | 170 | | | | | 175 | |

| Pro | Thr | Val | Pro | Asp | Arg | Asp | Asn | Asp | Gly | Ile | Pro | Asp | Ser | Leu | Glu |
|---|---|---|---|---|---|---|---|---|---|---|---|---|---|---|---|
| | | | 180 | | | | | 185 | | | | | 190 | | |

| Val | Glu | Gly | Tyr | Thr | Val | Asp | Val | Lys | Asn | Lys | Arg | Thr | Phe | Leu | Ser |
|---|---|---|---|---|---|---|---|---|---|---|---|---|---|---|---|
| | | 195 | | | | | 200 | | | | | 205 | | | |

| Pro | Trp | Ile | Ser | Asn | Ile | His | Glu | Lys | Lys | Gly | Leu | Thr | Lys | Tyr | Lys |
|---|---|---|---|---|---|---|---|---|---|---|---|---|---|---|---|
| | 210 | | | | | 215 | | | | | 220 | | | | |

| Ser | Ser | Pro | Glu | Lys | Trp | Ser | Thr | Ala | Ser | Asp | Pro | Tyr | Ser | Asp | Phe |
|---|---|---|---|---|---|---|---|---|---|---|---|---|---|---|---|
| 225 | | | | | 230 | | | | | 235 | | | | | 240 |

| Glu | Lys | Val | Thr | Gly | Arg | Ile | Asp | Lys | Asn | Val | Ser | Pro | Glu | Ala | Arg |
|---|---|---|---|---|---|---|---|---|---|---|---|---|---|---|---|
| | | | | 245 | | | | | 250 | | | | | 255 | |

| His | Pro | Leu | Val | Ala | Ala | Tyr | Pro | Ile | Val | His | Val | Asp | Met | Glu | Asn |
|---|---|---|---|---|---|---|---|---|---|---|---|---|---|---|---|
| | | | 260 | | | | | 265 | | | | | 270 | | |

| Ile | Ile | Leu | Ser | Lys | Asn | Glu | Asp | Gln | Ser | Thr | Gln | Asn | Thr | Asp | Ser |
|---|---|---|---|---|---|---|---|---|---|---|---|---|---|---|---|
| | | 275 | | | | | 280 | | | | | 285 | | | |

| Glu | Thr | Arg | Thr | Ile | Ser | Lys | Asn | Thr | Ser | Thr | Ser | Arg | Thr | His | Thr |
|---|---|---|---|---|---|---|---|---|---|---|---|---|---|---|---|
| | 290 | | | | | 295 | | | | | 300 | | | | |

| Ser | Glu | Val | His | Gly | Asn | Ala | Glu | Val | His | Ala | Ser | Phe | Phe | Asp | Ile |
|---|---|---|---|---|---|---|---|---|---|---|---|---|---|---|---|
| 305 | | | | | 310 | | | | | 315 | | | | | 320 |

| Gly | Gly | Ser | Val | Ser | Ala | Gly | Phe | Ser | Asn | Ser | Asn | Ser | Ser | Thr | Val |
|---|---|---|---|---|---|---|---|---|---|---|---|---|---|---|---|
| | | | | 325 | | | | | 330 | | | | | 335 | |

| Ala | Ile | Asp | His | Ser | Leu | Ser | Leu | Ala | Gly | Glu | Arg | Thr | Trp | Ala | Glu |
|---|---|---|---|---|---|---|---|---|---|---|---|---|---|---|---|
| | | | 340 | | | | | 345 | | | | | 350 | | |

| Thr | Met | Gly | Leu | Asn | Thr | Ala | Asp | Thr | Ala | Arg | Leu | Asn | Ala | Asn | Ile |
|---|---|---|---|---|---|---|---|---|---|---|---|---|---|---|---|
| | | 355 | | | | | 360 | | | | | 365 | | | |

| Arg | Tyr | Val | Asn | Thr | Gly | Thr | Ala | Pro | Ile | Tyr | Asn | Val | Leu | Pro | Thr |
|---|---|---|---|---|---|---|---|---|---|---|---|---|---|---|---|
| | 370 | | | | | 375 | | | | | 380 | | | | |

| Thr | Ser | Leu | Val | Leu | Gly | Lys | Asn | Gln | Thr | Leu | Ala | Thr | Ile | Lys | Ala |
|---|---|---|---|---|---|---|---|---|---|---|---|---|---|---|---|
| 385 | | | | | 390 | | | | | 395 | | | | | 400 |

| | | | | | | | | | | | | | | |
|---|---|---|---|---|---|---|---|---|---|---|---|---|---|---|
| Lys | Glu | Asn | Gln | Leu 405 | Ser | Gln | Ile | Leu 410 | Ala | Pro | Asn | Asn | Tyr 415 | Tyr | Pro |
| Ser | Lys | Asn | Leu 420 | Ala | Pro | Ile | Ala | Leu 425 | Asn | Ala | Gln | Asp | Asp 430 | Phe | Ser |
| Ser | Thr | Pro 435 | Ile | Thr | Met | Asn | Tyr | Gly 440 | Asn | Ile | Ala | Thr | Tyr 445 | Asn | Phe |
| Glu | Asn 450 | Gly | Arg | Val | Arg | Val 455 | Asp | Thr | Gly | Ser | Asn 460 | Trp | Ser | Glu | Val |
| Leu 465 | Pro | Gln | Ile | Gln | Glu 470 | Thr | Thr | Ala | Arg | Ile 475 | Ile | Phe | Asn | Gly | Lys 480 |
| Asp | Leu | Asn | Leu | Val 485 | Glu | Arg | Arg | Ile | Ala 490 | Ala | Val | Asn | Pro | Ser 495 | Asp |
| Pro | Leu | Glu | Thr 500 | Thr | Lys | Pro | Asp | Met 505 | Thr | Leu | Lys | Glu | Ala 510 | Leu | Lys |
| Ile | Ala | Phe 515 | Gly | Phe | Asn | Glu | Pro 520 | Asn | Gly | Asn | Leu | Gln 525 | Tyr | Gln | Gly |
| Lys | Asp 530 | Ile | Thr | Glu | Phe | Asp 535 | Phe | Asn | Phe | Asp | Gln 540 | Gln | Thr | Ser | Gln |
| Asn 545 | Ile | Lys | Asn | Gln | Leu 550 | Ala | Glu | Leu | Asn | Ala 555 | Thr | Asn | Ile | Tyr | Thr 560 |
| Val | Leu | Asp | Lys | Ile 565 | Lys | Leu | Asn | Ala | Lys 570 | Met | Asn | Ile | Leu | Ile 575 | Arg |
| Asp | Lys | Arg | Phe 580 | His | Tyr | Asp | Arg | Asn 585 | Asn | Ile | Ala | Val | Gly 590 | Ala | Asp |
| Glu | Ser | Val 595 | Val | Lys | Glu | Ala | His 600 | Arg | Glu | Val | Ile | Asn 605 | Ser | Ser | Thr |
| Glu | Gly 610 | Leu | Leu | Leu | Asn | Ile 615 | Asp | Lys | Asp | Ile | Arg 620 | Lys | Ile | Leu | Ser |
| Gly 625 | Tyr | Ile | Val | Glu | Ile 630 | Glu | Asp | Thr | Glu | Gly 635 | Leu | Lys | Glu | Val | Ile 640 |
| Asn | Asp | Arg | Tyr | Asp 645 | Met | Leu | Asn | Ile | Ser 650 | Ser | Leu | Arg | Gln | Asp 655 | Gly |
| Lys | Thr | Phe | Ile 660 | Asp | Phe | Lys | Lys | Tyr 665 | Asn | Asp | Lys | Leu | Pro 670 | Leu | Tyr |
| Ile | Ser | Asn 675 | Pro | Asn | Tyr | Lys | Val 680 | Asn | Val | Tyr | Ala | Val 685 | Thr | Lys | Glu |
| Asn | Thr 690 | Ile | Ile | Asn | Pro | Ser 695 | Glu | Asn | Gly | Asp | Thr 700 | Ser | Thr | Asn | Gly |
| Ile 705 | Lys | Lys | Ile | Leu | Ile 710 | Phe | Ser | Lys | Lys | Gly 715 | Tyr | Glu | Ile | Gly | |

( 2 ) INFORMATION FOR SEQ ID NO:32:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:32:

Arg   Lys   Lys   Arg
    1

( 2 ) INFORMATION FOR SEQ ID NO:33:

(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:33:

Arg Glu Asp Leu Lys
1               5

(2) INFORMATION FOR SEQ ID NO:34:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:34:

Leu Asp Glu Arg
1

(2) INFORMATION FOR SEQ ID NO:35:

(i) SEQUENCE CHARACTERISTICS:
    (A) LENGTH: 9 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:35:

Val Ala Ala Tyr Pro Ile Val His Val
1               5

ANTHRAX TOXIN FUSION PROTEINS AND RELATED METHODS

This application is in a continuation in part application of Ser. No. 08/021,601 filed Feb. 12, 1993 now U.S. Pat. No. 5,591,631.

BACKGROUND OF THE INVENTION

The targeting of cytotoxic or other moieties to specific cell types has been proposed as a method of treating diseases such as cancer. Various toxins including Diphtheria toxin and Pseudomonas exotoxin A have been suggested as potential candidate toxins for this type of treatment. A difficulty of such methods has been the inability to selectively target specific cell types for the delivery of toxins or other active moieties.

One method of targeting specific cells has been to make fusion proteins of a toxin and a single chain antibody. A single-chain antibody (sFv) consists of an antibody light chain variable domain ($V_L$) and heavy chain variable domain ($V_H$), connected by a short peptide linker which allows the structure to assume a conformation capable of binding to antigen. In a diagnostic or therapeutic setting, the use of an sFv may offer attractive advantages over the use of a monoclonal antibody (MoAb). Such advantages include more rapid tumor penetration with concomitantly low retention in non-targeted organs (Yokota et al. *Cancer Res* 52:3402,1992), extremely rapid plasma and whole body clearance (resulting in high tumor to normal tissue partitioning) in the course of imaging studies (Colcher et al. *Natl. Cancer Inst.* 82:1191, 1990; Milenic et al. *Cancer Res.* 51:6363, 1991), and relatively low cost of production and ease of manipulation at the genetic level (Huston et al. *Methods Enzymol.* 203:46, 1991; Johnson, S. and Bird, R. E. *Methods Enzymol.* 203:88, 1991). In addition, sFv-toxin fusion proteins have been shown to exhibit enhanced anti-tumor activity in comparison with conventional chemically cross-linked conjugates (Chaudhary et al. *Nature* 339:394, 1989; Batra et al. *Cell. Biol.* 11:2200-2295, 1991). Among the first sFv to be generated were molecules capable of binding haptens (Bird et al. *Science* 242:423, 1988; Huston et al. *Proc. Natl. Acad. Sci. USA* 85:5879, 1988), cell-surface receptors (Chaudhary et al., 1989), and tumor antigens (Chaudhary et al. *Proc. Natl. Acad. Sci. USA* 87:1066, 1990; Colcher et al., 1990).

The gene encoding an sFv can be assembled in one of two ways: (i) by de novo construction from chemically synthesized overlapping oligonucleotides, or (ii) by polymerase chain reaction (PCR)-based cloning of $V_L$ and $V_H$ genes from hybridoma cDNA. The main disadvantages of the first approach are the considerable expense involved in oligonucleotide synthesis, and the fact that the sequence of $V_L$ and $V_H$ must be known before gene assembly is possible. Consequently, the majority of the sFv reported to date were generated by cloning from hybridoma cDNA; nevertheless, this approach also has inherent disadvantages, because it requires availability of the parent hybridoma or myeloma cell line, and problems are often encountered when attempting to retrieve the correct V region genes from heterologous cDNA. For example, hybridomas in which the immortalizing fusion partner is derived from MOPC-21 may express a $V_L$ kappa transcript which is aberrantly rearranged at the VJ recombination site, and which therefore encodes a non-functional light chain (Cabilly & Riggs, 1985; Carroll et al., 1988). Cellular levels of this transcript may exceed that generated from the productive $V_L$ gene, so that a large proportion of the product on PCR amplification of hybridoma cDNA will not encode a functional light chain. A second disadvantage of the PCR-based method, frequently encountered by the inventors, is the variable success of recovering $V_H$ genes using the conditions so far reported in the literature, presumably because the number of mismatches between primers and the target sequence destabilizes the hybrid to an extent which inhibits PCR amplification.

Thus, methods of targeting toxins to specific cells using single-chain antibodies methods have been difficult to practice because of the difficulties in obtaining single chain antibodies and other targeting moieties. Also, none of the proposed treatment methods has been fully successful, because of the need to fuse the toxin to the targeting moiety, thus disrupting either the toxin function or the targeting function. Thus, a need exists for a means to target molecules having a desired activity to a specific cell population.

Bacterial and plant protein toxins have evolved novel and efficient strategies for penetrating to the cytosol of mammalian cells, and this ability has been exploited to develop anti-tumor and anti-HIV cytotoxic agents. Examples include ricin and Pseudomonas exotoxin A (PE) chimeric toxins and immunotoxins.

Pseudomonas exotoxin A (PE) is a toxin for which a detailed analysis of functional domains exists. The sequence is deposited with GenBank. Structural determination by X-ray diffraction, expression of deleted proteins, and extensive mutagenesis studies have defined three functional domains in PE: a receptor-binding domain (residues 1-252 and 365-399) designated Ia and Ib, a central translocation domain (amino acids 253-364, domain II), and a carboxyl-terminal enzymatic domain (amino acids 400-613, domain III). Domain III catalyzes the ADP-ribosylation of elongation factor 2 (EF-2), which results in inhibition of protein synthesis and cell death. Recently it was also found that an extreme carboxyl terminal sequence is essential for toxicity (Chaudhary et al. *Proc. Natl. Acad. Sci. U.S.A.* 87:308-312, 1990; Seetharam et al. *J. Biol. Chem.* 266:17376-17381, 1991). Since this sequence is similar to the sequence that specifies retention of proteins in the endoplasmic reticulum (ER) (Munro, S. and Pelham, H. R. B. *Cell* 48:899-907, 1987), it was suggested that PE must pass through the ER to gain access to the cytosol. Detailed knowledge of the structure of PE has facilitated use of domains II, Ib, and III (together designated PE40) in hybrid toxins and immunotoxins.

*Bacillus anthracis* produces three proteins which when combined appropriately form two potent toxins, collectively designated anthrax toxin. Protective antigen (PA, 82,684 Da (Dalton) (SEQ ID NOS: 3 and 4)) and edema factor (EF, 89,840 Da) combine to form edema toxin (ET), while PA and lethal factor (LF, 90,237 Da (SEQ ID NOS: 1 and 2)) combine to form lethal toxin (LT) (Leppla, S. H. Alouf, J. E. and Freer, J. H., eds. *Academic Press, London* 277-302, 1991). ET and LT each conform to the AB toxin model, with PA providing the target cell binding (B) function and EF or LF acting as the effector or catalytic (A) moieties. A unique feature of these toxins is that LF and EF have no toxicity in the absence of PA, apparently because they cannot gain access to the cytosol of eukaryotic cells.

The genes for each of the three anthrax toxin components have been cloned and sequenced (Leppla, 1991). This showed that LF and EF have extensive homology in amino acid residues 1-300. Since LF and EF compete for binding to PA63, it is highly likely that these amino-terminal regions are responsible for binding to PA63. Direct evidence for this was provided in a recent mutagenesis study (Quinn et al. *J. Biol. Chem.* 266:20124–20130, 1991); all mutations made within amino acid residues 1–210 of LF led to decreased binding to PA63. The same study also suggested that the putative catalytic domain of LF included residues 491–776 (Quinn et al., 1991). In contrast, the location of functional domains within the PA63 polypeptide is not obvious from inspection of the deduced amino acid sequence. However, studies with monoclonal antibodies and protease fragments (Leppla, 1991) and subsequent mutagenesis studies (Singh et al. *J. Biol. Chem.* 266:15493–15497, 1991) showed that residues at and near the carboxyl terminus of PA are involved in binding to receptor.

PA is capable of binding to the surface of many types of cells. After PA binds to a specific receptor (Leppla, 1991) on the surface of susceptible cells, it is cleaved at a single site by a cell surface protease, probably furin, to produce an amino-terminal 19-kDa fragment that is released from the receptor/PA complex (Singh et al. *J. Biol. Chem.* 264:19103–19107, 1989). Removal of this fragment from PA exposes a high-affinity binding site for LF and EF on the receptor-bound 63-kDa carboxyl-terminal fragment (PA63). The complex of PA63 and LF or EF enters cells and probably passes through acidified endosomes to reach the cytosol.

Cleavage of PA occurs after residues 164–167, Arg-Lys-Lys-Arg(SEQ. ID NO: 32). This site is also susceptible to cleavage by trypsin and can be referred to as the trypsin cleavage site. Only after cleavage is PA able to bind either EF or LF to form either ET or LT.

Prior work had shown that the carboxyl terminal PA fragment (PA63) can form ion conductive channels in artificial lipid membranes (Blaustein et al. *Proc. Natl. Acad. Sci. U.S.A.* 86:2209–2213, 1989; Koehler, T. M. and Collier, R. J. *Mol. Microbiol.* 5:1501–1506, 1991), and that LF bound to PA63 on cell surface receptors can be artificially translocated across the plasma membrane to the cytosol by acidification of the culture medium (Friedlander, A. M. *J. Biol. Chem.* 261:7123–7126, 1986). Furthermore, drugs that block endosome acidification protect cells from LF (Gordon et al. *J. Biol. Chem.* 264:14792–14796, 1989; Friedlander, 1986; Gordon et al. Infect. Immun. 56:1066–1069, 1988). The mechanisms by which EF is internalized have been studied in cultured cells by measuring the increases in cAMP concentrations induced by PA and EF (Leppla, S. H. *Proc. Natl. Acad. Sci. U.S.A.* 79:3162–3166, 1982; Gordon et al., 1989). However, because assays of cAMP are relatively expensive and not highly precise, this is not a convenient method of analysis. Internalization of LF has been analyzed only in mouse and rat macrophages, because these are the only cell types lysed by the lethal toxin.

SUMMARY OF THE INVENTION

The present invention provides a nucleic acid encoding a fusion protein comprising a nucleotide sequence encoding the PA binding domain of the native LF protein and a nucleotide sequence encoding an activity inducing domain of a second protein. Also provided is a nucleic acid encoding a fusion protein comprising a nucleotide sequence encoding the translocation domain and LF binding domain of the native PA protein and a nucleotide sequence encoding a ligand domain which specifically binds a cellular target. Proteins encoded by the nucleic acid of the invention, vectors comprising the nucleic acids and hosts capable of expressing the protein encoded by the nucleic acids are also provided.

A composition comprising the PA binding domain of the native LF protein chemically attached to an activity inducing moiety is further provided.

A method for delivering an activity to a cell is provided. The steps of the method include administering to the cell (a) a protein comprising the translocation domain and the LF binding domain of the native PA protein and a ligand domain and (b) a product comprising the PA binding domain of the native LF protein and a non-LF activity inducing moiety, whereby the product administered in step (b) is internalized into the cell and performs the activity within the cell.

Characteristics unique to anthrax toxin are exploited to make novel cell-specific cytotoxins. A site in the PA protein of the toxin which must be proteolytically cleaved for the activity-inducing moiety of the toxin to enter the cell is replaced by the consensus sequence recognized by a specific protease. Thus, the toxin will only act on cells infected with intracellular pathogens which make that specific protease.

DESCRIPTION OF THE PREFERRED EMBODIMENT

Nucleic Acids

Lethal Factor (LF)

Figure 1:
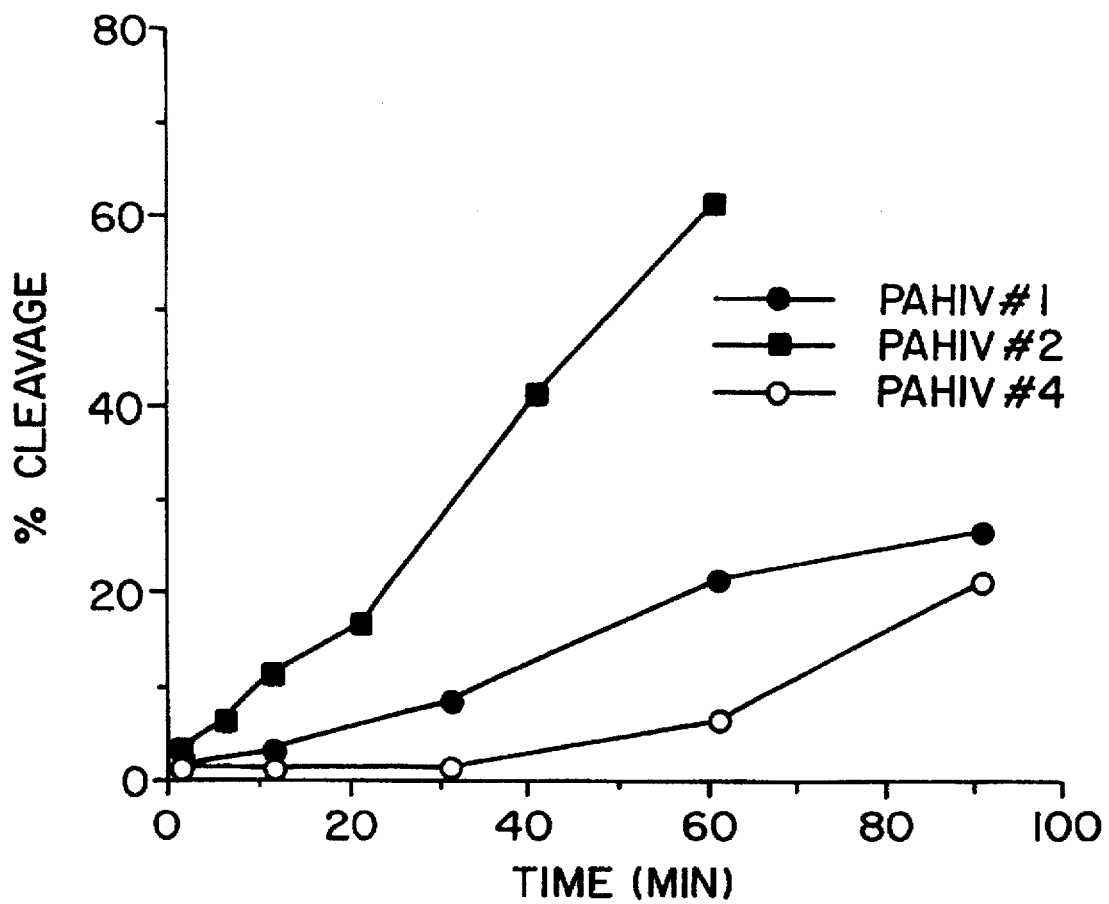
FIG. 1 is a graph of the percent to which mutant proteins are cleaved by purified HIV-1 protease. The mutant proteins include protective antigen (PA) mutated to include the HIV-1 protease cleavage site in place of the natural trypsin cleavage site.

The present invention provides an isolated nucleic acid encoding a fusion protein comprising a nucleotide sequence encoding the PA binding domain of the native LF protein and a nucleotide sequence encoding an activity inducing domain of a second protein. The LF gene and native LF protein are shown in SEQ. ID NO: 1 and 2, respectively. The PA gene and native PA protein are shown in SEQ. ID NO: 3 and 4, respectively.

The second protein can be a toxin, for example Pseudomonas exotoxin A (PE), the A chain of Diphtheria toxin or shiga toxin. The activity inducing domains of numerous other known toxins can be included in the fusion protein encoded by the presently claimed nucleic acid. The activity inducing domain need not be a toxin, but can have other activities, including but not limited to stimulating or reducing growth, selectively inhibiting DNA replication, providing enzymatic activity or providing a source of radiation. In any case, the fusion proteins encoded by the nucleic acids of the present invention must be capable of being internalized and capable of expressing the specified activity in a cell. A given LF fusion protein of the present invention can be tested for its ability to be internalized and to express the desired activity using methods as described herein, particularly in Examples 1 and 2.

An example of a nucleic acid of the invention comprises the nucleotide sequence defined in the Sequence Listing as SEQ. ID NO: 5. This nucleic acid encodes a fusion of LF residues 1–254 with the two-residue linker "TR" and PE residues 401–602 (SEQ. ID NO: 6). The protein includes a Met-Val-Pro- sequence at the beginning of the LF sequence. Means for obtaining this fusion protein are further described below and in Example 1.

A further example of a nucleic acid of this invention comprises the nucleotide sequence defined in the Sequence Listing as SEQ. ID NO: 7. This nucleic acid encodes a fusion of LF residues 1–254 with the two-residue linker "TR" and PE residues 398–613. (SEQ. ID NO: 8) The junction point containing the "TR" is the sequence LTRA and the Met-Val-Pro- is also present. This fusion protein and methods for obtaining it are further described below and in Example 2.

Another example of the nucleic acid of the present invention comprises the nucleotide sequence defined in the Sequence Listing as SEQ. ID NO: 9. This nucleic acid encodes a fusion of LF residues 1–254 with the two residue linker and PE residues 362–613. (SEQ. ID NO: 10) This fusion protein is further described in Example 1.

Alternatively, the nucleic acid can include the entire coding sequence for the LF protein fused to a non-LF activity inducing domain. Other LF fusion proteins of various sizes and methods of making and testing them for the desired activity are also provided herein, particularly in Examples 1 and 2.

Protective Antigen (PA)

Also provided is an isolated nucleic acid encoding a fusion protein comprising a nucleotide sequence encoding the translocation domain and LF binding domain of the native PA protein and a nucleotide sequence encoding a ligand domain which specifically binds a cellular target.

An example of a nucleic acid of this invention comprises the nucleotide sequence defined in the Sequence Listing as SEQ. ID NO: 11. This nucleic acid encodes a fusion of PA residues 1–725 and human CD4 residues 1–178, the portion which binds to gp120 exposed on HIV-1 infected cells (SEQ ID NO:12). This fusion protein and methods for obtaining and testing fusion proteins are further described below and in Examples 3, 4 and 5.

The PA fusion protein encoding nucleic acid provided can encode any ligand domain that specifically binds a cellular target, e.g. a cell surface receptor, an antigen expressed on the cell surface, etc. For example, the nucleic acid can encode a ligand domain that specifically binds to an HIV protein expressed on the surface of an HIV-infected cell. Such a ligand domain can be a single chain antibody which is expressed as a fusion protein as provided above and in Examples 3, 4 and 5. Alternatively, the nucleic acid can encode, for example, a ligand domain that is a growth factor, as provided in Example 3.

Although the PA encoding sequence of the nucleic acid encoding the PA fusion proteins of this invention need only include the nucleotide sequence encoding the translocation domain and LF binding domain of the native PA protein, the nucleic acid can further comprise the nucleotide sequence encoding the remainder of the native PA protein. Any sequences to be included beyond those required, can be determined based on routine considerations such as ease of manipulation of the nucleic acid, ease of expression of the product in the host, and any effect on translocation/internalization as taught in the examples.

Proteins

Proteins encoded by the nucleic acids of the present invention are also provided.

LF Fusion Proteins

The present invention provides LF fusion proteins encoded by the nucleic acids of the invention as described above and in the examples. Specifically, fusions of the LF gene with domains II, Ib, and III of PE can be made by recombinant methods to produce in-frame translational fusions. Recombinant genes (e.g., SEQ ID NOs: 5, 7 and 9) were expressed in *Escherichia coli* (E. coli), and the purified proteins were tested for activity on cultured cells as provided in Examples 1 and 2. Certain fusion proteins are efficiently internalized via the PA receptor to the cytosol. These examples demonstrate that this system can be used to deliver many different polypeptides into targeted cells.

Although specific examples of these proteins are provided, given the present teachings regarding the preparation of LF fusion proteins, other embodiments having other activity inducing domains can be practiced using routine skill.

Using current methods of genetic manipulation, a variety of other activity inducing moieties (e.g., polypeptides) can be translated as fusion proteins with LF which in turn can be internalized by cells when administered with PA or PA fusion proteins. Fusion proteins generated by this method can be screened for the desired activity using the methods set forth in the Examples and by various routine procedures. Based on the data presented here, the present invention provides a highly effective system for delivery of an activity inducing moiety into cells.

PA fusion proteins

The present invention provides PA fusion proteins encoded by the nucleic acids of the invention. Specifically, fusions of PA with single chain antibodies and CD4 are provided.

Using current methods of genetic manipulation, a variety of other ligand domains (e.g., polypeptides) can be translated as fusion proteins with PA which in turn can specifically target cells and facilitate internalization LF or LF fusion proteins. Based on the data presented here, the present invention provides a highly effective system for delivery of an activity inducing moiety into a particular type or class of cells.

Although specific examples of these proteins are provided, given the present teachings regarding the preparation of PA fusion proteins, other embodiments having other ligand domains can be practiced using routine skill. The fusion proteins generated can be screened for the desired specificity and activity utilizing the methods set forth in the example and by various routine procedures. In any case, the PA fusion proteins encoded by the nucleic acids of the present invention must be able to specifically bind the selected target cell, bind LF or LF fusions or conjugates and internalize the LF fusion/conjugate.

Conjugates

A composition comprising the PA binding domain of the native LF protein chemically attached to an activity inducing moiety is provided. Such an activity inducing moiety is an activity not present on native LF. The composition can comprise an activity inducing moiety that is, for example, a polypeptide, a radioisotope, an antisense nucleic acid or a nucleic acid encoding a desired gene product.

Using current methods of chemical manipulation, a variety of other moieties (e.g., polypeptides, nucleic acids, radioisotopes, etc.) can be chemically attached to LF and can be internalized into cells and can express their activity when administered with PA or PA fusion proteins. The compounds can be tested for the desired activity and internalization following the methods set forth in the Examples. For example, the present invention provides an LF protein fragment 1–254 (LF1–254) with a cysteine residue added at the end of LF1–254 (LF1–254Cys). Since there are no other cysteines in LF, this single cysteine provides a convenient attachment point through which to chemically conjugate other proteins or non-protein moieties.

Vectors and Hosts

A vector comprising the nucleic acids of the present invention is also provided. The vectors of the invention can be in a host capable of expressing the protein encoded by the nucleic acid.

To express the proteins and conjugates of the present invention, the nucleic acids can be operably linked to signals that direct gene expression. A nucleic acid is "operably linked" when it is placed into a functional relationship with another nucleic acid sequence. For instance, a promoter or enhancer is operably linked to a coding sequence if it affects the transcription of the sequence. Generally, operably linked means that the nucleic acid sequences being linked are contiguous and, where necessary to join two protein coding regions, contiguous and in reading frame.

The gene encoding a protein of the invention can be inserted into an "expression vector", "cloning vector", or "vector," terms which usually refer to plasmids or other nucleic acid molecules that are able to replicate in a chosen host cell. Expression vectors can replicate autonomously, or they can replicate by being inserted into the genome of the host cell. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

The particular vector used to transport the genetic information into the cell is also not particularly critical. Any of the conventional vectors used for expression of recombinant proteins in prokaryotic or eukaryotic cells can be used.

The expression vectors typically have a transcription unit or expression cassette that contains all the elements required for the expression of the DNA encoding a protein of the invention in the host cells. A typical expression cassette contains a promoter operably linked to the DNA sequence encoding the protein, and signals required for efficient polyadenylation of the transcript. The promoter is preferably positioned about the same distance from the heterologous transcription start site as it is from the transcription start site in its natural setting. As is known in the art, however, some variation in this distance can be accommodated without loss of promoter function.

The DNA sequence encoding the protein of the invention can be linked to a cleavable signal peptide sequence to promote secretion of the encoded protein by the transformed cell. Additional elements of the vector can include, for example, selectable markers and enhancers. Selectable markers, e.g., tetracycline resistance or hygromycin resistance, permit detection and/or selection of those cells transformed with the desired DNA sequences (see, e.g., U.S. Pat. No. 4,704,362).

Enhancer elements can stimulate transcription up to 1,000 fold from linked homologous or heterologous promoters. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long terminal repeat from various retroviruses such as murine leukemia virus, murine or Rous sarcoma virus, and HIV. See, *Enhancers and Eukaryotic Expression*, Cold Spring Harbor Pres, Cold Spring Harbor, N.Y. 1983, which is incorporated herein by reference.

In addition to a promoter sequence, the expression cassette should also contain a transcription termination region downstream of the structural gene to provide for efficient termination. The termination region can be obtained from the same gene as the promoter sequence or can be obtained from a different gene.

For more efficient translation in mammalian cells of the mRNA encoded by the structural gene, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

The vectors containing the gene encoding the protein of the invention are transformed into host cells for expression. "Transformation" refers to the introduction of vectors containing the nucleic acids of interest directly into host cells by well known methods. The particular procedure used to introduce the genetic material into the host cell for expression of the protein is not particularly critical. Any of the well known procedures for introducing foreign nucleotide sequences into host cells can be used. It is only necessary that the particular procedure utilized be capable of successfully introducing at least one gene into the host cell which is capable of expressing the gene.

Transformation methods, which vary depending on the type of host cell, include electroporation; transfection employing calcium chloride, rubidium chloride calcium phosphate, DEAE-dextran, or other substances; microprojectile bombardment; lipofection; infection (where the vector is an infectious agent); and other methods. See, generally, Sambrook et al., (1989) supra, and *Current Protocols in Molecular Biology*, supra. Reference to cells into which the nucleic acids described above have been introduced is meant to also include the progeny of such cells.

There are numerous prokaryotic expression systems known to one of ordinary skill in the art useful for the expression of the antigen. *E. coli* is commonly used, and other microbial hosts suitable for use include *bacilli*, such as *Bacillus subtilus*, and other enterobacteriaceae, such as *Salmonella*, *Serratia*, and various *Pseudomonas* species. One can make expression vectors for use in these prokaryotic hosts; the vectors will typically contain expression control sequences compatible with the host cell (e.g., an origin of replication, a promoter). Any number of a variety of well-known promoters can be used, such as the lactose promoter system, a tryptophan (Trp) promoter system, a beta-lactamase promoter system, or a promoter from phage lambda. The promoters will typically control expression, optionally with an operator sequence, and have ribosome binding site sequences, for example, for initiating and completing transcription and translation. If necessary, an amino terminal methionine can be provided by insertion of a Met codon 5' and in-frame with the codons for the protein. Also, the carboxy-terminal end of the protein can be removed using standard oligonucleotide mutagenesis procedures, if desired.

Host bacterial cells can be chosen that are mutated to be reduced in or free of proteases, so that the proteins produced are not degraded. For Bacillus expression systems in which the proteins are secreted into the culture medium, strains are available that are deficient in secreted proteases.

Mammalian cell lines can also be used as host cells for the expression of polypeptides of the invention. Propagation of mammalian cells in culture is per se well known. See, *Tissue Culture*, Academic Press, Kruse and Patterson, ed. (1973). Host cell lines may also include such organisms as bacteria (e.g., *E. coli* or *B. subtilis*), yeast, filamentous fungi, plant cells, or insect cells, among others.

Purification of Protein

After standard transfection or transformation methods are used to produce prokaryotic, mammalian, yeast, or insect cell lines that express large quantities of the protein of the invention, the protein is then purified using standard techniques which are known in the art. See, e.g., Colley et al. (1989) *J. Biol. Chem.* 64: 17619–17622; and *Methods in Enzymology*, "Guide to Protein Purification", M. Deutscher, ed. Vol. 182 (1990).

Standard procedures of the art that can be used to purify proteins of the invention include ammonium sulfate precipitation, affinity and fraction column chromatography, gel electrophoresis and the like. See, generally, Scopes, R., *Protein Purification*, Springer-Verlag, N.Y. (1982), and U.S. Pat. No. 4,512,922 disclosing general methods for purifying protein from recombinantly engineered bacteria.

If the expression system causes the protein of the invention to be secreted from the cells, the recombinant cells are grown and the protein is expressed, after which the culture medium is harvested for purification of the secreted protein. The medium is typically clarified by centrifugation or filtration to remove cells and cell debris and the proteins can be concentrated by adsorption to any suitable resin such as, for example, CDP-Sepharose, asialoprothrombin-Sepharose 4B, or Q Sepharose, or by use of ammonium sulfate fractionation, polyethylene glycol precipitation, or by ultrafiltration. Other means known in the art are equally suitable. Further purification of the protein can be accomplished by standard techniques, for example, affinity chromatography, ion exchange chromatography, sizing chromatography, or other protein purification techniques used to obtain homogeneity. The purified proteins are then used to produce pharmaceutical compositions, as described below.

Alternatively, vectors can be employed that express the protein intracellularly, rather than secreting the protein from the cells. In these cases, the cells are harvested, disrupted, and the protein is purified from the cellular extract, e.g., by standard methods. If the cell line has a cell wall, then initial extraction in a low salt buffer may allow the protein to pellet with the cell wall fraction. The protein can be eluted from the cell wall with high salt concentrations and dialyzed. If the cell line glycosolates the protein, then the purified glycoprotein may be enhanced by using a Con A column. Anion exchange columns Mono Q® Pharmacia) and gel filtration columns may be used to further purify the protein. A highly purified preparation can be achieved at the expense of activity by denaturing preparative polyacrylamide gel electrophoresis.

Protein analogs can be produced in multiple conformational forms which are detectable under nonreducing chromatographic conditions. Removal of those species having a low specific activity is desirable and is achieved by a variety of chromatographic techniques including anion exchange or size exclusion chromatography.

Recombinant analogs can be concentrated by pressure dialysis and buffer exchanged directly into volatile buffers (e.g., N-ethylmorpholine (NEM), ammonium bicarbonate, ammonium acetate, and pyridine acetate). In addition, samples can be directly freeze-dried from such volatile buffers resulting in a stable protein powder devoid of salt and detergents. In addition, freeze-dried samples of recombinant analogs can be efficiently resolubilized before use in buffers compatible with infusion (e.g., phosphate buffered saline). Other suitable buffers might include hydrochloride, hydrobromide, sulphate acetate, benzoate, malate, citrate, glycine, glutamate, and aspartate.

Specific Embodiments

Toxins Modified to Contain Intracellular Pathogen Protease Recognition Sites

One aspect of the invention exploits the fact that PA and other toxins must be proteolytically cleaved in order to acquire activity, in conjunction with the fact that some cells infected with an intracellular pathogen possess an active protease that has a relatively narrow substrate specificity (for example, HIV-infected cells). The protease site found in the native toxin is replaced with an intracellular pathogen specific protease site. Thus, the protease in cells that are infected by the intracellular pathogen cleaves the modified toxin, which then becomes active and kills the cell.

Intracellular pathogens that can be targeted by the products and methods of the present invention include any pathogen that produces a protease having a specific recognition site. Such pathogens can include prokaryotes (including rickettsia, *Mycobacterium tuberculosis*, etc.), mycoplasma, eukaryotic pathogens (e.g. pathogenic fungi, etc.), and viruses. One example of an intracellular pathogen that produces a specific protease is human immunodeficiency virus (HIV). The HIV-1 protease cleaves viral polyproteins to generate functional structural proteins as well as the reverse transcriptase and the protease itself. HIV-1 replication and viral infectivity are absolutely dependent on the action of the HIV-1 protease.

An intracellular pathogen specific protease site can be introduced into any natural or recombinant toxin for which proteolytic cleavage is required for toxicity. For example, one can replace the anthrax PA trypsin cleavage site (R164–167) of PA with the HIV-1 protease site. Alternatively, the diphtheria toxin disulfide loop sequence (see O'Hare, et al. FEBS 273 (1, 2): 200–204 (October 1990)) can be replaced with the HIV-1 protease cleavage site in order to obtain a toxin specific to HIV-1 infected cells. Similarly, the normally occurring diphtheria toxin sequence at residues 191–194 (Williams, et al. *J. Biol. Chem.* 265(33): 20673–20677 (1990)) can be replaced by an intracellular pathogen specific protease site such as the HIV-1 protease cleavage sequence. The DAB486-IL-2 fusion toxin of Williams and the improved DAB389-IL-2 toxin are effective on HIV-1 infected cells, which express high levels of the IL-2 receptor. Williams, *J. Biol. Chem.* 265:20673. Addition of the HIV-1 protease cleavage site would provide a further degree of specificity. Similarly, the botulinum toxin C2 toxin is like the anthrax toxin in requiring a cleavage within a native protein subunit (see Ohishi and Yanagimoto, *Infection and Immunity* 60(11): 4648–4655 (November 1992)), so it too can be made specific for cells infected by an intracellular pathogen such as HIV-1.

In one embodiment of the invention, the protease site of PA is replaced by the site recognized by the HIV-1 protease. The cellular protease that cleaves PA absolutely requires the presence of the Arg 164 and Arg 167 residues, because replacement of either residue yields a PA molecule which is not cleaved after binding to the cell surface. However, any PA substitution mutant which retains at least one Arg or Lys residue within residues 164–167 can be activated by treatment with trypsin. Because the PA63 fragments produced by trypsin digestion have a variety of different amino terminal residues, it is clear that there is not a strict constraint on the identity of the terminal residues. Klimpel, et al., *Proc. Natl. Acad. Sci.* 89:10277–10281 (1992).

Replacement of residues 164–167 of PA with residues that match the HIV-1 protease recognition site can render exogenously added PA inactive on cells which do not possess the HIV-1 protease. However, those cells that do express the HIV-1 protease (i.e., cells infected with HIV-1 or cells engineered to produce the protease) would cleave and thereby activate the mutant PA. The activated PA proteins can then bind and internalize cytotoxic fusion proteins, such as LF-PE, added exogenously.

Based on extensive studies of the substrate specificity of the protease, several PA variants were designed and produced which relate to the invention. These are shown below, with the residues underlined between which the cleavage occurred. PA proteins which have been mutated to replace R164–167 with an amino acid sequence recognized by the HIV-1 protease are referred to as "PAHIV. " (SEQ. ID NO: 13)

| PAHIV#1 | QVSQNYPIVQNI (SEQ ID NO: 14) |
| PAHIV#2 | NTATIMMQRGNF (SEQ IDNO: 15) |
| PAHIV#3 | TVSFNFPQITLW (SEQ ID NO: 16) |
| PAHIV#4 | GGSAFNFPIVMGG (SEQ ID NO: 17) |

The mutant proteins PAHIV#(1–4) were cleaved correctly by the HIV-1 protease.

Table 1 shows the amino acids and their corresponding abbreviations and symbols.

TABLE 1

| A | Ala | Alanine | M | Met | Methionine |
| C | Cys | Cysteine | N | Asn | Asparagine |
| D | Asp | Aspartic acid | P | Pro | Proline |
| E | Glu | Glutamic acid | Q | Gln | Glutamine |
| F | Phe | Phenylalanine | R | Arg | Arginine |
| G | Gly | Glycine | S | Ser | Serine |
| H | His | Histidine | T | Thr | Threonine |
| I | Ile | Isoleucine | V | Val | Valine |
| K | Lys | Lysine | W | Trp | Tryptophan |
| L | Leu | Leucine | Y | Tyr | Tyrosine |

Preferably, the mutations at R164–167 of PA are accomplished by cassette mutagenesis, although other methods are feasible as discussed below. In summary, three pieces of DNA are joined together. The first piece has vector sequences and encodes the "front half" (5' end of the gene) of PA protein, the second is a short piece of DNA (a cassette) and encodes a small middle piece of PA protein and the third encodes the "back half" (3' end of the gene) of PA. The cassette contains codons for the amino acids that are required to complete the cleavage site for the intracellular pathogen protease. This method was used to make mutants in the plasmid pYS5 although other plasmids could be employed.

Alternatively, the mutations can be accomplished by use of the polymerase chain reaction (PCR) and other methods as discussed below. PCR duplicates a segment of DNA many times, resulting in an amplification of that segment. The reaction produces enough of the segment of DNA so that it can be modified with restriction enzymes and cloned. During the reaction a synthetic oligonucleotide primer is used to start the duplication of the target DNA segment. Each synthetic primer can be designed to introduce novel DNA sequences into the DNA molecule, or to change existing DNA sequences.

Modification of Toxins to Broaden or Alter Target Cell Specificity

Another aspect of the invention involves compounds and methods for broadening or changing the range of cell types against which a toxin is effective. For example, the lethal anthrax toxin, PA+LF, is acutely toxic to mouse macrophage cells, apparently due to the specific expression in these cells of a target for the catalytic activity of LF. Other cell types are not affected by LF. However, in the present invention, LF is used to construct cytotoxins having broad cell specificity.

A detailed analysis of the domains of LF identified the amino-terminal 254 amino acids as the region that binds to PA63. Fusion proteins containing residues 1–254 of LF and the ADP-ribosylation domain of Pseudomonas exotoxin A (PE) were designed according to the invention. These fusion proteins are highly toxic to cultured cells, but only when PA is administered simultaneously.

Synthesis of Genes that Encode Proteins of the Invention

Genes that encode toxins having altered protease recognition sites or fusion proteins having a binding domain from one protein and an activity inducing domain of a second protein can be synthesized by methods known to those skilled in the art. As an example of techniques that can be utilized, the synthesis of genes encoding modified anthrax toxin subunits LF and PA are now described.

The DNA sequences for native PA and LF are known. Knowledge of these DNA sequences facilitates the preparation of genes and can be used as a starting point to construct DNA molecules that encode mutants of PA and/or LF. The protein mutants of the invention are soluble and include internal amino acid substitutions. Furthermore, these mutants are purified from, or secreted from, cells that have been transfected or transformed with plasmids containing genes which encode these proteins. Methods for making modifications, such as amino acid substitutions, deletions, or the addition of signal sequences to cloned genes are known. Specific methods used herein are described below.

The gene for PA or LF can be prepared by several methods. Genomic and cDNA libraries are commercially available. Oligonucleotide probes, specific to the desired gene, can be synthesized using the known gene sequence. Methods for screening genomic and cDNA libraries with oligonucleotide probes are known. A genomic or cDNA clone can provide the necessary starting material to construct an expression plasmid for the desired protein using known methods.

A protein encoding DNA fragment can be cloned by taking advantage of restriction endonuclease sites which have been identified in regions which flank or are internal to the gene. See Sambrook, et al., *Molecular Cloning: A Laboratory Manual* 2d.ed. Cold Spring Harbor Laboratory Press (1989), "Sambrook" hereinafter.

Genes encoding the desired protein can be made from wild-type genes constructed using the gene encoding the full length protein. One method for producing wild-type genes for subsequent mutation combines the use of synthetic oligonucleotide primers with polymerase extension on a mRNA or DNA template. This PCR method amplifies the desired nucleotide sequence. U.S. Pat. Nos. 4,683,195 and 4,683,202 describe this method. Restriction endonuclease sites can be incorporated into the primers. Genes amplified by PCR can be purified from agarose gels and cloned into an appropriate vector. Alterations in the natural gene sequence can be introduced by techniques such as in vitro mutagenesis and PCR using primers that have been designed to incorporate appropriate mutations.

The proteins described herein can be expressed intracellularly and purified, or can be secreted when expressed in cell culture. If desired, secretion can be obtained by the use of the native signal sequence of the gene. Alternatively, genes encoding the proteins of the invention can be ligated in proper reading frame to a signal sequence other than that corresponding to the native gene. Though the PA recombinant proteins of the invention are typically expressed in *B. anthracis*, they can be expressed in other hosts, such as *E. coli*.

The proteins of this invention are described by their amino acid sequences and by their nucleotide sequence, it being understood that the proteins include their biological equivalents such that this invention includes minor or inadvertent substitutions and deletions of amino acids that have substantially little impact on the biological properties of the analogs. In some circumstances it may be feasible to substitute rare or non-naturally occurring amino acids for one or more of the twenty common amino acids listed in Table 2. Examples include ornithine and acetylated or hydroxylated forms. See generally Stryer, L., *Biochemistry* 3d ed. (1988).

Alternative nucleotide sequences can be used to express analogs in various host cells. Furthermore, due to the degeneracy of the genetic code, equivalent codons can be substituted to encode the same polypeptide sequence. Additionally, sequences (nucleotide and amino acid) with substantial identity to those of the invention are also included. Identity in this sense means the same identity (of base pair or amino acid) and order (of base pairs or amino acids). Substantial identity includes entities that are greater than 80% identical. Preferably, substantial identity refers to greater than 90% identity. More preferably, it refers to greater than 95% identity.

Mutagenesis

Mutagenesis can be performed to yield point mutations, deletions, or insertions to alter the specific regions of the genes described above. Point mutations can be introduced by a variety of methods including chemical mutagenesis, mutagenic copying methods and site specific mutagenesis methods using synthetic oligonucleotides.

Cassette mutagenesis methods are conveniently used to introduce point mutations into the specified regions of the PA or LF genes. A double-stranded oligonucleotide region containing alterations in the specified sequences of the gene is prepared. This oligonucleotide cassette region can be prepared by synthesizing an oligonucleotide with the sequence alteration in residues of the PA or LF gene, annealing to a primer, elongating with the large fragment of DNA polymerase and trimming with BstBI. This double-stranded oligonucleotide is ligated into the Bamhi/BstBI fragment from pYS5 and the PpuMI-BamHI fragment from pYS6 to produce an intact recombinant DNA. Other methods of producing the double stranded oligonucleotides and other recombinant DNA vectors can be practiced.

Chemical mutagenesis can be performed using the M13 vector system. A single strand M13 recombinant DNA is prepared containing recombinant PA or LF DNA. Another M13 recombinant containing the same recombinant DNA but in double stranded form is used to prepare a deletion in the targeted region of the gene. This double stranded M13 recombinant is cleaved into a linear molecule with an endonuclease, denatured, and annealed with the single strand M13 recombinant, resulting in a single strand gap in the target region of the PA or LF DNA.

This gapped DNA M13 recombinant is then treated with a compound such as sodium bisulfite to deaminate the cytosine residues in the single strand DNA region to uracil. This results in limited and specific mutations in the single strand DNA region. Finally, the gap in the DNA is filled in by incubation with DNA polymerase, resulting in a U-A base pair to replace a G-C base pair in the in unmutated portion of the gene. Upon replication the new recombinant gene contains T-A base pairs, which are point mutations from the original sequence. Other forms of chemical mutagenesis are also available.

Mutagenic copying of the PA or LF recombinant DNA can be carried out using several methods. For example, a single-stranded gapped DNA region is created as described above. This region is incubated with DNA polymerase I and one or more mutagenic analogs of normal ribonucleoside triphosphates. Copying of the single stranded region with the DNA polymerase substitutes the mutagenic analogs as the single strand gap region is filled in. Transfection and replication of the resulting DNA results in production of some mutated recombinant DNAs for PA, LF, or EF which can then be selected by cloning. Other mutagenic copying methods can be used.

Point mutations can be introduced into the specified regions of the PA or LF genes by methods using synthetic oligonucleotides for site-specific mutagenesis. PCR copying of the PA or LF genes is performed using oligonucleotide primers covering the specified target regions, and which contain modifications from the wild type sequence in these regions. The PA gene in a pYS5 vector can be PCR amplified using this method to result in mutations in the 164–167 position. PCR amplification can also be used to introduce mutations in the target region of the LF gene.

Synthetic oligonucleotide methods of introducing point mutations can be performed using heteroduplex DNA. A M13 recombinant DNA vector containing the PA or LF gene is prepared and a single-stranded M13 recombinant is produced. A single strand oligonucleotide containing an alteration in the specified target sequence for the PA or LF gene is annealed to the single strand M13 recombinant to produce a mismatched sequence. Incubation with DNA polymerase I results in a double-stranded M13 recombinant containing base pair mismatches in the specified region of the gene. This M13 recombinant is replicated in a host such as *B. anthracis* or *E. coli* to produce both wild type and mutant M13 recombinants. The mutated M13 recombinants are cloned and isolated. Other vector systems for mutagenesis involving synthetic nucleotides and heteroduplex formation can be applicable.

Expression of Proteins in Prokaryotic Cells

In addition to the use of cloning methods in bacteria such as *Bacillus anthracis* for amplification of cloned sequences, it may be desirable to express the proteins in other prokaryotes. It is possible to recover a functional protein from *E. coli* transformed with an expression plasmid encoding a PA or LF protein. Conveniently, the mutated PA proteins of the invention were expressed in *B. anthracis* and the LF-fusion proteins were expressed in *E. coli*.

Methods for the expression of cloned genes in bacteria are well known. See Sambrook. To optimize expression of a cloned gene in a prokaryotic system, expression vectors can be constructed which include a promoter to direct mRNA transcription termination. The inclusion of selection markers in DNA vectors transformed in bacteria are useful. Examples of such markers include the genes specifying resistance to ampicillin, tetracycline, or chloramphenicol.

See Sambrook, previously cited, for details concerning selection markers and promoters for use in bacteria such as *E. coli*. In an embodiment of this invention, pYS5 is a vector for the subcloning and amplification of desired gene sequences although other vectors could be used.

Strains of Bacillus Anthracis Producing Mutated Protein(s)

For PA protein production, *B. anthracis* strains cured of both pX01 and pX02 are preferred because they are avirulent. Examples of such strains are UM23C1-1 and UM44-1C9, obtained from Curtis Thorne, University of Massachusetts. Similar strains can be made by curing of plasmids, as described by P. Mikesell, et al., "Evidence for plasmid-mediated toxin production in *Bacillus anthracis*," *Infect. Immun.* 39:371–376 (1983).

See generally commonly assigned U.S. patent application Ser. No. 08/042,745, filed Apr. 5, 1993, now abandoned incorporated by reference herein.

Treatment Methods

A method for delivering a desired activity to a cell is provided. The steps of the method include administering to the cell (a) a protein comprising the translocation domain and the LF binding domain of the native PA protein and a ligand domain, and (b) a product comprising the PA binding domain of the native LF protein and a non-LF activity inducing moiety, whereby the product administered in step (b) is internalized into the cell and performs the activity within the cell.

The method of delivering an activity to a cell can use a ligand domain that is the receptor binding domain of the native PA protein. Other ligand domains are selected for their specificity for a particular cell type or class of cells. The specificity of the PA fusion protein for the targeted cell can be determined using standard methods and as described in Examples 2 and 3.

The method of delivering an activity to a cell can use an activity inducing moiety that is a polypeptide, for example a growth factor, a toxin, an antisense nucleic acid, or a nucleic acid encoding a desired gene product. The actual activity inducing moiety used will be selected based on its functional characteristics, e.g. its activity.

A method of killing a tumor cell in a subject is also provided. The steps of the method can include administering to the subject a first fusion protein comprising the translocation domain and LF binding domain of the native PA protein and a tumor cell specific ligand domain in an amount sufficient to bind to a tumor cell. A second fusion protein is also administered wherein the protein comprises the PA binding domain of the native LF protein and a cytotoxic domain of a non-LF protein in an amount sufficient to bind to the first protein, whereby the second protein is internalized into the tumor cell and kills the tumor cell.

The cytotoxic domain can be a toxin or it can be another moiety not strictly defined as a toxin, but which has an activity that results in cell death. These cytotoxic moieties can be selected using standard tests of cytotoxicity, such as the cell lysis and protein synthesis inhibition assays described in the examples.

The invention further provides a method of killing HIV-infected cells in a subject. The method comprises the steps of administering to the subject a first fusion protein comprising the translocation domain and LF binding domain of the native PA protein and a ligand domain that specifically binds to an HIV protein expressed on the surface of an HIV-infected cell, in an amount sufficient to bind to an HIV-infected cell. The next step is administering to the subject a second fusion protein comprising the PA binding domain of the native LF protein and a cytotoxic domain of a non-LF protein, in an amount sufficient to bind to the first protein, whereby the second protein is internalized into the HIV-infected cell and kills the HIV-infected cell, thereby preventing propagation of HIV.

Although certain of the methods of the invention have been described as using LF fusion proteins, it will be understood that other LF compositions having chemically attached activity inducing moieties can be used in the methods.

The fusion proteins and other compositions of the inventions can be administered by various methods, e.g., parenterally, intramuscularly or intrapertioneally.

The amount necessary can be deduced from other receptor/ligand or antibody/antigen therapies. The amount can be optimized by routine procedures. The exact amount of such LF and PA compositions required will vary from subject to subject, depending on the species, age, weight and general condition of the subject, the severity of the disease that is being treated, the particular fusion protein of composition used, its mode of administration, and the like. Generally, dosage will approximate that which is typical for the administration of cell surface receptor ligands, and will preferably be in the range of about 2 μg/kg/day to 2 mg/kg/day.

Depending on the intended mode of administration, the compounds of the present invention can be in various pharmaceutical compositions. The compositions will include, as noted above, an effective amount of the selected protein in combination with a pharmaceutically acceptable carrier and, in addition, can include other medicinal agents, pharmaceutical agents, carriers, adjuvants, diluents, etc. By "pharmaceutically acceptable" is meant a material that is not biologically or otherwise undesirable, i.e., the material can be administered to an individual along with the fusion protein or other composition without causing any undesirable biological effects or interacting in a deleterious manner with any of the other components of the pharmaceutical composition in which it is contained.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Formulations and Administration

Proteins of the invention such as PAHIV are typically mixed with a physiologically acceptable fluid prior to administration to a mammal such as a human. Examples of physiologically acceptable fluids include saline solutions such as normal saline, Ringer's solution, and generally mixtures of various salts including potassium and phosphate salts with or without sugar additives such as glucose. The proteins are administered parenterally with intravenous administration being the most typical route. Either a bolus of the protein in solution or a slow infusion can be administered intravenously. The choice of a bolus or an infusion depends on the kinetics, including the half-life, of the protein in the patient. An appropriate evaluation of the time for delivery of the protein is well within the skill of the clinician.

Patients selected for treatment with PAHIV are infected with HIV-1 and they may or may not be symptomatic. Optimally, the protein would be administered to an HIV-1 infected person who is not yet symptomatic. The dosage range of a protein of the invention such as PAHIV is typically from about 5 to about 25 micrograms per kilogram of body weight of the patient. Usually, the dose is about 10 micrograms per kilogram of body weight of the patient. The dosage is repeated at regular intervals, such as weekly for about 4 to 6 weeks. At that time the clinician may opt to evaluate the patient's immune status, including immunotolerance to the PAHIV, to decide future treatment.

The foregoing description and the following examples are offered primarily for purposes of illustration. It will be readily apparent to those skilled in the art that the operating conditions, materials, procedural steps and other parameters of the system described herein can be further modified or substituted in various ways without departing from the spirit and scope of the invention. For example, although human use has been discussed, veterinary use of the invention is also feasible. For instance, cats suffer from a so-called feline AIDS or feline immunodeficiency virus (FIV). Protective antigen can be altered to include a protease cleavage site specific for FIV. Thus, the invention is not limited by the description and examples, but rather by the appended claims.

EXAMPLE 1

Fusions of Anthrax Toxin Lethal Factor to the ADP-Ribosylation Domain of Pseudomonas Exotoxin Reagents and General Procedures Restriction endonucleases and DNA modifying enzymes were purchased from GIBCO/BRL, Boehringer Mannheim, or New England Biolabs. Low melting point agarose (Sea Plaque) was obtained from FMC Corp. (Rockland, Me.). Oligonucleotides were synthesized on a PCR Mate (Applied Biosystems) and purified on oligonucleotide purification cartridges (Applied Biosystems). The PCR was performed with a DNA amplification reagent (GeneAmp) from Perkin-Elmer Cetus Instruments and a thermal cycler (Perkin-Elmer Cetus). The amplification involved denaturation at 94° C. for 1 min, annealing at 55° C. for 2.5 min and extension at 72° C. for 3 min, for 30 cycles. A final extension was run at 72° C. for 7 min. For amplification of PE fragments, 10% formamide was added in the reaction mixture to decrease the effect of high GC content. DNA sequencing reactions were done using the Sequenase version 1.0 from U.S. Biochemical Corp. and DNA sequencing gels were made from Gel Mix 6 from GIBCO/BRL. [$^{35}$S]deoxyadenosine 5'-[α-thio] triphosphate and L-[3,4,5-$^{3}$H]leucine were purchased from Dupont-New England Nuclear. J774A.1 cells were obtained from American Type Culture Collection. Chinese Hamster Ovary (CHO) cells were obtained from Michael Gottesman (National Cancer Institute, National Institutes of Health) (ATCC CCL 61).

Plasmid Construction

Construction of plasmids containing LF-PE fusions was performed as follows. Varying portions of the PE gene were amplified by PCR, ligated in frame to the 3' end of the LF gene, and inserted into the pVEX115 f+T expression vector (provided by V. K. Chaudhary, National Cancer Institute, National Institutes of Health). To construct fusion proteins, the 3'-end of the native LF gene (including codon 776 of the mature protein, specifying Ser) was ligated with the 5'-ends of sequences specifying varying portions of domains II, Ib, and III of PE. The LF gene was amplified from the plasmid pLF7 (Robertson, D. L. and Leppla, S. H. *Gene* 44:71–78, 1986) by PCR using PCR using oligonucleotide primers which added KpnI and MluI sites at the 5' and the 3' ends of the gene, respectively. Similarly, varying portions of the PE gene (provided by David FitzGerald, National Cancer Institute, National Institutes of Health) were amplified by PCR so as to add MluI and EcORI sites at the 5' and 3' ends. The PCR product of the LF gene was digested with KpnI and the DNA was precipitated. The LF gene was subsequently treated with MluI. Similarly, the PCR products of PE amplification were digested with MluI and EcoRI. The expression vector pVEX115 f+T was cleaved with KpnI and EcoRI separately and dephosphorylated. This vector has a T7 promoter, OmpA signal sequence, multiple cloning site, and T7 transcription terminator. All the above DNA fragments were purified from low-melting point agarose, a three-fragment ligation was carried out, and the product transformed into *E. coli* DH5α (ATCC 53868). The four constructs described in this report have the entire LF gene fused to varying portions of PE. The identity of each construct was confirmed by sequencing the junction point using a Sequenase kit (U.S. Biochemical Corp.). For expression, recombinant plasmids were transformed into *E. coli* strain SA2821 (provided by Sankar Adhya, National Cancer Institute, National Institutes of Health, which is a derivative of BL21(λDE3) (Studier, F. W. and Moffatt, B. A. *J. Mol. Biol.* 189:113–150, 1986). This strain has the T7 RNA polymerase gene under control of an inducible lac promotor and also contains the degP mutation, which eliminates a major periplasmic protease (Strauch et al. *J. Bacteriol.* 171:2689–2696, 1989).

In the resulting plasmids, the LF-PE fusion genes are under control of the T7 promoter and contain an OmpA signal peptide to obtain secretion of the products to the periplasm so as to facilitate purification. The design of the PCR linkers also led to insertion of two non-native amino acids, Thr-Arg, at the LF-PE junction. The four fusions analyzed in this report contain the entire 776 amino acids of mature LF, the two added residues TR (Thr-Arg), and varying portions of PE. In fusion FP33, the carboxyl-terminal end of PE was changed from the native REDLK (Arg-Glu-Asp-Leu-Lys) (SEQ. ID NO: 33) to LDER (SEQ. ID NO: 34), a sequence that fails to cause retention in the ER (endoplasmic reticulum).

Expression and Purification of Fusion Proteins

Fusion proteins produced from pNA2, pNA4, pNA23 and pNA33 were designated FP2, FP4, FP23 and FP33 respectively. *E. coli* strains carrying the recombinant plasmids were grown in super broth (32 g/L Tryptone, 20 g/L yeast extract, 5 g/L NaCl, pH 7.5) with 100 µg/ml of ampicillin with shaking at 225 rpm at 37° C. in 2-L cultures. When $A_{600}$ reached 0.8–1.0, isopropyl-1-thio-β-D-galactopyranoside was added to a final concentration of 1 mM, and cultures were incubated an additional 2 hr. EDTA and 1,10-o-phenanthroline were added to 5 mM and 0.1 mM respectively, and the bacteria were harvested by centrifugation at 4000×g for 15 min at 4° C. For extraction of the periplasmic contents, cells were suspended in 75 ml of 20% sucrose containing 30 mM Tris and 1 mM EDTA, incubated at 0° C. for 10 min, and centrifuged at 8000×g for 15 min at 4° C. Cells were resuspended gently in 50 ml of cold distilled water, kept on ice for 10 min, and the spheroplasts were pelleted. The supernatant was concentrated with CENTRI PREP®-100 units (Amicon) and loaded on a SEPHACRYL® S-200 (a cross-linked co-polymer of alkyl dextron and N,N'-methylenebisacrylanide column (40×2 cm) and 1 ml fractions were collected.

Fractions having full length fusion protein as determined by immunoblots were pooled and concentrated as above. Protein was then purified on an anion exchange column (Mono Q® HR5/5, Pharmacia-LKB) using a NaCl gradient. The fusion proteins eluted at 280–300 mM NaCl. The proteins were concentrated again on CENTRIPREP®-100 (Amicon Division) and the Mono Q® chromatography was repeated. Protein concentrations were determined by the bicinchoninic acid method (BCA Protein Assay Reagent, Pierce), using bovine serum albumin as the standard. Proteins were analyzed by polyacrylamide gel electrophoresis in the presence of sodium dodecyl sulfate (SDS). Gels were either stained with Coomassie Brilliant Blue or the proteins were electroblotted to nitrocellulose paper which was probed with polyclonal rabbit antisera to LF or PE (List Biological Laboratories, Campbell, Calif). To determine the percent of full length protein, SDS gels stained with Coomassie Brilliant Blue were scanned with a laser densitometer (Pharmacia-LKB Ultrascan XL).

The proteins migrated during gel electrophoresis with molecular masses of more than 106 kDa, consistent with the expected sizes, and immunoblots confirmed that the products had reactivity with antisera to both LF and PE. The fusion proteins differed in their susceptibility to proteolysis as judged by the appearance of smaller fragments on immunoblots, and this led to varying yields of final product. Thus, from 2-L cultures the yields were FP2, 27 µg; FP4, 87 µg; FP23, 18 µg; and FP33, 143 µg.

Cell Culture Techniques and Protein Synthesis Inhibition Assay

CHO cells were maintained as monolayers in Eagle's minimum essential medium (EMEM) supplemented with 10% fetal bovine serum, 10 mM 4-2(2-hydroxyethyl)-1-piperazineethanesulfonic acid (HEPES) (pH 7.3), 2 mM glutamine, penicillin/streptomycin, and non-essential amino acids (GIBCO/BRL). Cells were plated in 24- or 48-well dishes one day before the experiment. After overnight incubation, the medium was replaced with fresh medium containing 1 µg/ml of PA unless otherwise indicated. Fusion proteins were added to 0.1–1000 ng/ml. All data points were done in duplicate. Cells were further incubated for 20 hr at 37° C. in 5% $CO_2$ atmosphere. The medium was then aspirated and cells were incubated for 2 hr at 37° C. with leucine-free medium containing 1 µCi/ml [$^3$H]leucine. Cells were washed twice with medium, cold 10% trichloroacetic acid was added for 30 min, the cells were washed twice with 5% trichloroacetic acid and dissolved in 0.150 ml 0.1M NaOH. Samples were counted in Pharmacia-LKB 1410 liquid scintillation counter. In experiments to determine if the toxin is internalized through acidified endosomes, 1 µM monensin (Sigma) was added 90 min prior to toxin and was present during all subsequent steps. To verify that the fusion proteins were internalized through the PA receptor, competition with native LF was carried out. PA (0.1 µg/ml) and LF (0.1–10,000 ng/ml) were added to the CHO cells to block the PA receptor and the fusion proteins were added thereafter at concentrations of 100 ng/ml for FP4 and FP23 and 5 ng/ml for FP 33. Protein synthesis inhibition was measured after 20 hr as described above.

Cytotoxic Activity of the Fusion Proteins

All four fusion proteins made and purified were toxic to CHO cells. The concentration causing 50% lysis of cultured cells ($EC_{50}$) values of the proteins were 350, 8, 10, and 0.2 ng/ml for FP2, FP4, FP23 and FP33 respectively (Table 1). These assays were done with PA present at 1 ug/ml, exceeding the $K_m$ of 0.1 ug/ml (100 pM). The fusion proteins had no toxicity even at 1 µg/ml when PA was omitted, proving that internalization of the fusion proteins was occurring through the action of PA and the PA receptor. Native LF has previously been shown to have no short-term toxic effects on CHO cells when added with PA, and therefore was not included in these assays. The fusion protein having only domain III and an altered carboxyl-terminus (FP33) was most active, whereas the one having the intact domains II and III and the native REDLK (SEQ. ID NO: 33) terminus (FP2) was least active. The other two fusion proteins (FP4 and FP23) had intermediate potencies.

Among proteins having ADP-ribosylation activity, potencies equalling or exceeding 1 pM have previously been found only for native diphtheria and Pseudomonas toxins acting on selected cells (Middlebrook, J. L. and Dorlan, R. B. *Can. J. Microbiol.* 23:183–189, 1977) and for fusion proteins of PE and diphtheria toxin when tested on cells containing>100,000 receptors for the ligand-recognition domain of the fusion (EGF, transferrin, etc.) (Pastan, I. and FitzGerald, D. *Science* 254:1173–1177, 1991; Middlebrook, et al. 1977). For CHO cells, the potency of FP33 ($EC_{50}$=2 pM) is higher than that of PE itself ($EC_{50}$=420 pM), even though CHO cells probably have similar numbers of receptors for both PA and PE (approx. 5,000–20,000). If the intracellular trafficking of native PE delivers less than 5% of the molecules to the cytosol, then the 200-fold greater potency of FP33 suggests that the PA/LF system has an inherently high efficiency of delivery to the cytosol.

A comparison of the potencies of the four fusion proteins shows that inclusion of domain II decreases potency. Thus, the fusion with the lowest potency, FP2, was the one containing intact domains II, Ib, and III. In designing the fusion proteins, all or part of PE domain II and Ib was included in several of the constructs because it could not be assumed that the translocation functions possessed by PA and LF would be able to correctly traffic PE domain III to the cytosol. The combination of domains II, Ib, and III, termed PE40, has been used in a large number of toxic hybrid proteins, by fusion to growth factors, monoclonal antibodies, and other proteins (Pastan et al. 1991; Oeltmann, T. N. and Frankel, A. E. *FASEB J.* 5:2334–2337, 1991), and some of these fusions have shown substantial potency. Domain II was found to be essential in these hybrid proteins to provide a translocation function not present in the receptor-binding domain to which it was fused. The potency of many of these PE40 fusion proteins appears to require that they be trafficked through the Golgi and ER and proteolytically activated in the same manner as native PE, so as to achieve delivery of domain III to the cytosol. The fact that inclusion of the entire domain II in the LF fusion protein FP2 instead decreased activity suggests that internalization of the LF fusions occurs through a different route, one that does not easily accommodate all the sequences in domain II.

Evidence that structures within PE residues 251–278 inhibit translocation of the LF fusions comes from the 35-fold lower potency of FP2 compared to FP23. One structure that might inhibit translocation of the fusions is the disulfide loop formed by Cys265 and Cys287. In native PE, this disulfide loop appears to be required for maximum activity. Thus, native PE and TGF-α-PE40 fusions become 10- to 100-fold less toxic if one or both these cysteines are changed to serine. The disulfide loop probably acts to constrain the polypeptide so that Arg276 and Arg279 are susceptible to the intracellular protease involved in the cleavage that precedes translocation. In contrast, the disulfide loop decreases the potency of the LF fusions, perhaps by preventing the unfolding needed for passage through a protein channel, thereby acting in this situation as a "stop transfer" sequence. FP23, which lacks Cys265, would not contain the domain II disulfide, and therefore would not be subject to this effect. LF, like PA and EF, contains no cysteines, and would not be prevented by disulfide loops from the complete unfolding needed to pass through a protein channel. The suggestion that disulfide loops act as stop-transfer signals would predict that the disulfide Cys372-Cys379 in PE domain Ib, which is retained in all four LF fusions would also decrease potency. It should be noted that neither the fusions made here nor the PE40 fusions have been analyzed chemically to determine if the disulfides in domains II and III are actually formed. If the disulfides do form correctly, it would be predicted that the potencies of all of the fusion proteins, and especially that of FP2, would be increased by treatment with reducing agents. These analyses have not yet been performed. This analysis also suggests that future LF fusions might be made more potent by omission of domain Ib.

The other structural feature of PE known to affect intracellular trafficking is the carboxyl terminal sequence, REDLK (SEQ. ID NO: 33), that specifies retention in the ER (Chaudhary et al. 1990; Muro et al. 1987). To determine if the trafficking of the LF fusion proteins was similar to that of PE, two of the fusion proteins were designed so as to differ only in the terminal sequence. Replacement of the native sequence by LDER (SEQ. ID NO: 34), one that does not function as an ER retention signal, produced the most toxic of the four fusion proteins, FP33. FP4, identical except that it retained a functional REDLK (SEQ. ID NO: 33) sequence, was 30-fold less potent. These data suggest that sequestration of the REDLK-ended (SEQ. ID NO: 33) fusions decreased their access to cytosolic EF-2. The implication is that PE may require the REDLK (SEQ. ID NO: 33) terminus to be delivered to the ER for an obligatory processing step, but then be limited in its final toxic potential by sequestration from its cytosolic target. Finally, this comparison strongly argues that internalization of the LF fusions does not follow the same path as PE.

In designing the fusion proteins described here it was hoped that they would have cytotoxic activity against cells that are unaffected by anthrax lethal toxin, and this was successfully realized as shown by the data obtained with CHO cells. However, prior knowledge about LF did not provide a basis for predicting whether the constructs would retain toxicity toward mouse macrophages, the only cells known to be rapidly killed by anthrax lethal toxin. Macrophages are lysed by lethal toxin in 90–120 minutes, long before any inhibition of protein synthesis resulting from ADP-ribosylation of EF-2 leads to decreases in membrane integrity or viability. This kinetic difference made it possible to test directly for LF action. As discussed above, the fusion proteins purified to remove the -89-kDa LF species formed by proteolysis were not toxic to J774A.1 macrophages. This shows that attachment of a bulky group to the carboxyl terminus of LF eliminates its normal toxic activity. In the absence of any assay for the putative catalytic activity of LF, it is not possible to determine the cause of the loss of LF activity. The inability of the fusions to lyse J774A.1 cells also argues against proteolytic degradation of the fusions either in the medium during incubation with cells or after internalization.

An important result of the invention described here is the demonstration that the anthrax toxin proteins constitute an efficient mechanism for protein internalization into animal cells. The high potency of the present fusion proteins argues that this system is inherently efficient, as well as being amenable to improvement. The high efficiency results in part from the apparent direct translocation from the endosome, without a requirement for trafficking through other intracellular compartments. In addition to its efficiency, the system appears able to tolerate heterologous polypeptides.

Macrophage Lysis Assay of Fusion Proteins

Fusion proteins were assayed for LF functional activity on J774A.1 macrophage cell line in the presence of 1 µg/ml PA. One day prior to use, cells were scraped from flasks and plated in 48-well tissue culture dishes. For cytotoxicity tests, the medium was aspirated and replaced with fresh medium containing 1 µg/ml PA and the LF fusion proteins, and the cells were incubated for 3 hr. All data points were performed in duplicate. To measure the viability of the treated cells, 3-[4,5-dimethylthiazol-2-yl]-2,5-diphenyltetrazolium bromide (MTT) was added to the cells to a final concentration of 0.5 mg/ml, and incubation was continued for an additional 45 min to allow the uptake and oxidation of MTT by viable cells. Medium was aspirated and replaced by 200 µl of 0.5% SDS, 40 mM HCl, 90% isopropanol and the plates were vortexed to dissolve the blue pigment. The MTT absorption was read at 570 nm using a UVmax Kinetic Microplate Reader (Molecular Devices Corp.).

The crude periplasmic extracts from which the fusion proteins were purified caused lysis of J774A.1 macrophages when added with PA, indicating the presence of active LF species, probably formed by proteolysis of the fusion proteins. Purification removed this activity, so that none of the final fusion proteins had this activity. This result showed both that the purified proteins were devoid of full size LF or active LF fragments, and that the lytic activity of LF for macrophages is blocked when residues from PE are fused at its carboxyl terminus.

ADP-Ribosylation Assays

For assaying ADP-ribosylation activity, the method of Collier and Kandel (Collier, R. J. and Kandel, J. *J. Biol. Chem.* 246:1496–1503, 1971) was used with some modification. A wheat germ extract enriched for EF-2 was used in the reaction. Briefly, in a 200-µL reaction assay, 20 µL of buffer (500 mM Tris, 10 mM EDTA, 50 mM dithiothreitol and 10 mg/ml bovine serum albumin) was mixed with 30 µL of EF-2, 130 µL of $H_2O$ or sample, and 20 µL of [adenylate-$^{32}$P]NAD (0.4 µCi per assay, ICN Biochemicals) containing 5 µM of non-radioactive NAD. Samples were incubated for 20 min at 23° C., the reactions were stopped by adding 1 ml 10% trichloroacetic acid, and the precipitates were collected and washed on GA-6 filters (Gelman Sciences). The filters were washed twice with 70% ethanol, air dried, and the radioactivity measured.

Table 1 shows that all the fusion proteins were equally capable of ADP-ribosylation of EF-2. FP2, which had little cytotoxic activity on CHO cells, still retained full ADP-ribosylation activity. It was also found that treatment with urea and dithiothreitol under conditions that activate the enzymatic activity of native PE, caused no increase in the ADP-ribosylation activity of the fusion proteins, suggesting that the proteins were not folded so as to sterically block the catalytic site.

Effect of Mutant PA on LF-PE Activity

To verify that uptake of the fusion proteins requires PA, the activity of the fusion proteins was measured in the presence of a mutant PA which is apparently defective in internalization. This mutant, PA-S395C, has a serine to cysteine substitution at residue 395 of the mature protein, and retains the ability to bind to receptor, become proteolytically nicked, and bind LF, but is unable to lyse macrophages. When PA-S395C was substituted for native PA in combination with FP33, no inhibition of protein synthesis inhibition was observed. Similar results were obtained when the other three fusion proteins were tested in combination with PA-S395C.

Effect of Monensin on Activity of the Fusion Proteins

To verify that internalization of the fusion proteins was occurring by passage through acidified endosomes in the same manner as native LF, the ability of monensin to protect cells was examined. Addition of monensin to 1 µM decreased the potency of FP33 by >100-fold. Protection against the other three fusion proteins exceeded 20-fold.

LF Block of LF-PE Fusion Activity

To further verify that the fusion proteins were internalized through the PA receptor, CHO cells were incubated with PA and different amounts of LF to block the receptor and the fusion proteins were added thereafter. Protein synthesis inhibition assays showed that native LF could competitively block LF-PE fusion proteins in a concentration-dependent manner.

The present data suggest that the receptor-bound 63-kDa proteolytic fragment of PA forms a membrane channel and that regions at or near the amino-termini of LF and EF enter this channel first and thereby cross the endosomal membrane, followed by unfolding and transit of the entire polypeptide to the cytosol. This model differs from that for diphtheria toxin in that the orientation of polypeptide transfer is reversed. Since both EF and LF have large catalytic domains, extending to near their carboxyl termini, it appears probable that the entire polypeptide crosses the membrane. In the LF fusion proteins, the attached PE sequences would be carried along with the LF polypeptide in transiting the channel to the cytosol. Thus, the PA63 protein channel must tolerate diverse amino acid residues and sequences. The data presented is consistent with the mechanism of direct translocation of the LF proteins to the cytosol as suggested herein.

TABLE 1

Cytotoxic and catalytic activity of LF-PE fusion proteins

| Protein | Amino acid content | | | Toxicity $(EC_{50})^b$ | ADP-Ribosylation activity |
|---|---|---|---|---|---|
| | LF | Linker | PE | (pM) | ng/ml (relative) |
| PE | none | none | 1–613 | 420 | 23 | 100$^c$ |
| FP2 | 776 | TR | 251–613 | 2700 | 350 | 82 |
| FP4 | 776 | TR | 362–613 | 65 | 8 | 105 |
| FP23 | 776 | TR | 279–613 | 70 | 10 | 108 |
| FP33 | 776 | TR | 362–612$^a$ | 2 | 0.2 | 118 |

$^a$REDLK (SEQ ID NO: 33) at carboxyl terminus is changed to LDER (SEQ ID NO: 34).
$^b$Data is from this example, except for native PE, which is from data not shown, and is equal to a value previously reported (Moehring, T. J. and Moehring, J. M. Cell 11:447–454, 1977).
$^c$ADP-ribosylation was measured using 30 ng of fusion protein in a final volume of 0.200 ml with 5 μM NAD. Results were corrected for the molecular weights of the proteins and normalized to PE.

EXAMPLE 2

Residues 1–254 of Anthrax Toxin Lethal Factor are Sufficient to Cause Cellular Uptake of Fused Polypeptides Reagents and General Procedures Restriction endonucleases and DNA modifying enzymes were purchased from GIBCO/BRL, Boehringer Mannheim or New England Biolabs. Low melting point agarose (Sea Plaque) was obtained from FMC Corporation. Oligonucleotides were synthesized on a PCR Mate (Applied Biosystems) and purified with Oligonucleotide Purification Cartridges (Applied Biosystems). Polymerase chain reactions (PCR) were performed on a thermal cycler (Perkin-Elmer-Cetus) using reagents from U. S. Biochemical Corp. or Perkin-Elmer-Cetus. DNA was amplified as described in Example 1. The DNA was sequenced to confirmed the accuracy of all of the constructs described in the report. SEQUENASE version 2.0 from U.S. Biochemical Corp. was utilized for the sequencing reactions, and DNA sequencing gels were made with Gel Mix 8 from GIBCO/BRL. [$^{35}$S] dATPαS and L-[3,4,5-$^3$H]leucine were purchased from Dupont-New England Nuclear. Chinese hamster ovary cells (CHO) were obtained from Michael Gottesman (NCI, NIH). J774A.1 macrophage cells were obtained from American Type Culture Collection.

Plasmid Construction

Three types of LF protein constructs were made and analyzed in this report. All the constructs were made by PCR amplification of the desired sequences, using the native LF gene as template. LF proteins deleted at the amino- or carboxyl-terminus were constructed by a single PCR amplification reaction that added restriction sites at the ends for incorporation of the construct into the expression vector. LF proteins deleted for one or more of the 19-amino acid repeats that comprise residues 308–383 were constructed by ligating the products of two separate PCR reactions that amplified the regions bracketing the deletion. The third group of constructs were fusions of varying portions of the amino terminus of LF with PE domains Ib and III. Like the internally-deleted LF proteins, these LF-PE fusions were also made by ligation of two separate PCR products. In the latter two types of constructs, the ligation of the PCR products resulted in addition of a linker, ACGCGT, at the junction points. This introduced two non-native residues, Thr-Arg, between the fused domains. The PCR manipulations also added three non-native amino acids, Met-Val-Pro, as an extension to the native amino terminus on all the constructs described in this report. Addition of this sequence is not likely to alter the activity of the constructs (discussed below). It should be noted that the LF-PE fusions described herein contain this three-residue extension.

For PCR reactions to make deletions of 40 and 78 amino acids from the amino-terminus of LF, two different mutagenic oligonucleotide primers were made which were substantially identical to the LF gene template at the intended new termini, and which added KpnI sites at their 5'-ends. Another (non-mutagenic) oligonucleotide primer for introduction of a BamHI site at the 3' end of LF was prepared. Similarly, to make deletions at the carboxyl-terminus of LF, two different mutagenic primers were used which truncated LF at residues 729 and 693 and introduced a BamHI site next to the new 3' ends of the LF gene. A second (non-mutagenic) oligonucleotide primer specific for the amino terminus of LF was made which introduced a KpnI site at the 5' end of the gene. All of the primers noted above were used in PCR reactions on a pLF7 template (Robertson and Leppla, 1986) to synthesize DNA fragments having KpnI and BamHI sites at their 5' and 3' ends, respectively. The amplified LF DNAs containing the amino- and carboxyl-terminal deletions were digested with the appropriate restriction enzymes. The expression vector pVEX115f+T (provided by V. K. Chaudhary, NCI, NIH) was cleaved sequentially with KpnI and BamHI and dephosphorylated. This expression vector contains a T7 promoter, an OmpA signal sequence for protein transport to the periplasm, a multiple cloning site that includes KpnI and BamHI sites, and a T7 transcription terminator. The LF and pVEX115f+T DNA fragments were purified from low melting point agarose, ligated overnight, and transformed into E. coli DH5α. Transformants were screened by restriction digestion to identify the desired recombinant plasmids. Proteins produced by these constructs are designated according to the amino acid residues retained; for example the LF truncated at residue 693 is designated $LF^{1-693}$. All of the mutant LF proteins described above contain three non-native amino acids, Met-Val-Pro, added to the amino-terminus as a result of the PCR manipulations.

To analyze the role of the repeat region of LF, four different constructs were made: 1., removal of the entire repeat region ($LF^{1-307}.TR.LF^{384-776}$), 2., removal of the first repeat ($LF^{1-307}.TR.LF^{327-776}$) 3., removal of the last repeat ($LF^{1-364}.TR.LF^{384-776}$), and 4., removal of repeats 2–4 ($LF^{1-326}.TR.LF^{384-776}$). To construct $LF^{1-307}.TR.LF^{384-776}$, four different primers were used in two separate PCR reactions. To amplify $LF^{1-307}$, one oligonucleotide primer was made at the 5'-end of the LF gene which added a KpnI site, and a second primer was constructed at the end of residue 307, introducing an MluI site.

For amplifying $LF^{384-776}$, a third primer was made at residue 384 with an added MluI site, and the fourth primer was made at the residue 776 which introduced a BamHI site at the end. Two PCR amplifications were done using primers one/two and three/four with pLF7 as template (Robertson and Leppla, 1986). The first amplification reaction was digested with KpnI and MluI separately, and the second amplification reaction was digested with MluI and BamHI. The expression vector pVEX115f+T was digested separately with KpnI and BamHI and dephosphorylated. All three fragments were gel purified, ligated overnight at 16° C. and transformed into E. coli DH5α. The other three constructs were made by similar strategies. Oligonucleotide primers one and four were the same for all four constructs, whereas primers two and three were changed accordingly. All four constructs contain Met-Val-Pro at the amino terminus of LF and Thr-Arg at the site of the repeat region deletion.

To construct LF-PE fusion proteins, fragments of the LF gene extending from the amino terminus to various lengths were amplified from plasmid pLF7 (Robertson and Leppla, 1986) by PCR using a common oligonucleotide primer that added a KpnI site at the 5' end and mutagenic primers which added MluI sites at the intended new 3' ends. The PCR products of the LF gene were digested with KpnI, the DNAs were precipitated, and subsequently digested with MluI. Domains Ib and III of the PE gene (provided by David FitzGerald, NCI, NIH) were amplified by PCR using primers which added MluI and EcoRI sites at the 5' and 3' ends, respectively. The PCR product of PE was digested with MluI and EcoRI. Similarly, the expression vector pVEX115f+T was digested with KpnI and EcoRI. All DNA fragments were purified from low-melting agarose gels, three-fragment ligations were carried out, and the products were transformed into E. coli DH5α. The three constructs described in this example have 254, 198 and 79 amino acids of LF joined with PE domains Ib and III. These fusion proteins are designated $LF^{1-254}.TR.PE^{362-613}$ (SEQ. ID NO: 10), $LF^{1-198}.TR.PE^{362-613}$, and $LF^{1-79}.TR.PE^{362-613}$, respectively. The proteins retain the native carboxyl-terminal sequence of PE, REDLK (SEQ. ID NO: 33). It should be noted that these abbreviations do not specify the entire amino acid content of the proteins, because all the constructs also contain Met-Val-Pro, which was added to the amino-terminus of the LF domain by the PCR manipulations.

Expression and Purification of Deleted LF and Fusion Proteins

Recombinant plasmids were transformed into *E. coli* SA2821 (provided by Sankar Adhya, NCI, NIH), a derivative of BL21(λDE3) (Studier and Moffatt, 1986) that lacks the proteases encoded by the lon, OmpT, and degP genes, and has the T7 RNA polymerase gene under control of the lac promoter (Strauch et al., 1989). Transformants were grown in super broth with 100 μg/ml ampicillin, with shaking at 225 rpm, 37° C., in 2-L cultures. When $A_{600}$ reached 0.8–1.0, isopropyl-1-thio-β-D-galactopyranoside was added to a final concentration of 1 mM, and cultures were incubated for an additional 2 h. EDTA and 1,10-o-phenanthroline were added to 5 and 0.1 mM, respectively, and periplasmic protein was extracted as described in Example 1. The supernatant fluids were concentrated by CENTRIPREP®-30 units (Amicon) and proteins were purified to near homogeneity by gel filtration SEPHACRYL® S-200 (a cross-linked co-polymer of alkyl dextron and N,N,'-methylenebisacrylanide Pharmacia-LKB) and anion exchange chromatography (Mono Q®, Pharmacia-LKB) as described in Example 1. To determine the percentage of full length protein, SDS gels stained with Coomassie Brilliant Blue were scanned with a laser densitometer (Pharmacia-LKB Ultrascan XL). Western blots were performed as described previously (Singh et al., 1991).

The LF proteins having terminal deletions and the LF-PE fusion proteins were obtained from periplasmic extracts and purified to near homogeneity by gel filtration and anion exchange chromatography. The migration of the proteins was consistent with their expected molecular weights. Immunoblots confirmed that the LF proteins had reactivity with LF antisera, and the LF-PE fusion proteins had reactivity with both LF and PE antisera. Fusion proteins and terminally-deleted LF proteins differed in their susceptibility to proteolysis as judged by the appearance of peptide fragments on the immunoblots, and this was also reflected in the different amounts of purified proteins obtained. Thus, from 2-L cultures the yields of purified proteins were $LF^{41-776}$, 39 μg; $LF^{79-776}$, 32 μg; $LF^{1-729}$, 50 μg; $LF^{1-693}$, 46 μg; $LF^{1-254}$.TR.$PE^{362-613}$, 184 μg; $LF^{1-198}$.TR.$PE^{362-613}$, 80 μg; $LF^{1-79}$.TR.$PE^{362-613}$, 127 μg.

LF proteins deleted in the repeat region were found to be unstable and full size product could not be purified. Therefore, the activities of these proteins were determined by assay of crude periplasmic extracts, and immunoblots were used to estimate the amount of the full size proteins present.

Cytotoxicity on Macrophages of LF Proteins Having Terminal and Internal Deletions Deleted LF proteins were assayed for LF functional activity on the J774A.1 macrophage cell line in the presence of native PA as described in Example 1. Briefly, cells were plated in 24- or 48-well dishes in Dulbecco's modified Eagle medium (DMEM) containing 10% fetal bovine serum, and allowed to grow for 18 h. PA (1 μg/ml) and the mutant LF proteins were added and cells were incubated for 3 h. To measure the viability of the treated cells, 3-[4,5-dimethylthiazol-2-yl]-2,5-diphenyltetrazolium bromide (MTT) was added to the cells to a final concentration of 0.5 mg/ml. After incubating for 45 min, the medium was aspirated and cells were dissolved in 90% isopropanol, 0.5% SDS, 40 mM HCl, and read at 540 nm using a UVmax Kinetic Microplate Reader (Molecular Devices Corp.).

To determine the extent of essential sequences at the amino terminus of LF, the toxicities of the two LF proteins deleted at the amino-terminus were measured in combination with PA in the macrophage lysis assay. Purified $LF^{41-776}$ and $LF^{79-776}$ were unable to lyse J774A.1 macrophage cells. This indicates that some portion of the sequence preceding residue 41 is needed to maintain an active LF protein.

To examine the role of the carboxyl terminus of LF, two proteins truncated in this region were prepared and analyzed. The proteins $LF^{1-693}$ and $LF^{1-729}$ were assayed on J774A.1 cells and found to be inactive. This is presumed to be due to inactivation of the putative catalytic domain.

To begin study of the role of the repeat region of LF, four constructs were made having deletions in this region. The proteins expressed from these mutants were unstable. Of the four deleted proteins, only $LF^{1-307}$.TR.$LF^{327-776}$ had immunoreactive material at the position expected of intact fusion protein. The amount of intact $LF^{1-307}$.TR.$LF^{327-776}$ was similar to that of native LF expressed in the same vector. When these unpurified periplasmic extracts were tested in J774A.1 macrophages, only the native LF control was toxic. $LF^{1-307}$.TR.$LF^{327-776}$ did not lyse macrophages even when present at 50-fold higher concentration than that of crude periplasmic protein of LF. Conclusions cannot be drawn about the toxicities of the other three constructs because full size fusion proteins were not present in the periplasmic extracts.

Cell Culture Techniques and Protein Synthesis Inhibition Assay of Fusion Proteins CHO cells were maintained as monolayers in α-modified minimum essential medium (α-MEM) supplemented with 5% fetal bovine serum, 10 mM HEPES (pH 7.3), and penicillin/streptomycin. Protein synthesis assays were carried out in 24- or 48-well dishes as described in Example 1. CHO cells were incubated with PA (0.1 ug/ml) and varying concentrations of LF, which is expected to block the receptor. Fusion proteins were added at fixed concentrations, as follows: FP4, 100 ng/ml, FP23, 100 ng/ml, and FP33, 5 ng/ml. Cells were incubated for 20 hr and protein synthesis inhibition was evaluated by [$^3$H]leucine incorporation.

Cytotoxicity of the LF-PE Fusion Proteins on CHO Cells

The use of fusion proteins provides a more defined method for measuring the translocation of LF, as demonstrated in Example 1 showing that fusions of LF with domains Ib and III of PE are highly toxic. Translocation of these fusions is conveniently measured because domain III blocks protein synthesis by ADP-ribosylation of elongation factor 2. The new fusions containing varying portions of LF fused to PE domains Ib and III were designed to identify the minimum LF sequence able to promote translocation. The EC$_{50}$ of LF$^{1-254}$.TR.PE$^{362-613}$ (SEQ. ID NO: 10) was 1.7 ng/ml, whereas LF$^{1-198}$.TR.PE$^{362-613}$ and LF$^{1-79}$.TR.PE$^{362-613}$ did not kill 50% of the cells even at a 1200-fold higher concentration. Other constructs were also made and analyzed, containing larger portions of LF fused to PE domains Ib and III, and found those to be equal in potency to LF$^{1-254}$.TR.PE$^{362-613}$. These results show that residues 1-254 contain all the sequences essential for binding to PA63. The fusion proteins had no toxicity in the absence of PA, proving that their internalization absolutely requires interaction with PA.

Binding of Fusion Proteins and Deleted LF Proteins to PA

Binding of LF proteins to cell bound PA was determined by competition with radiolabeled $^{125}$I-LF. Native LF was radiolabeled (3.1×10$^6$ cpm/μg protein) using the Bolton-Hunter reagent. Binding studies employed the L6 rat myoblast cell line, which has approximately twice as many receptors as the J774A.1 macrophage line (Singh et al., 1989). For convenience, cells were chemically fixed by a gentle procedure that preserves the binding activity of the receptor as well as the ability of the cell-surface protease to cleave PA to produce receptor-bound PA63. Assays were carried out in 24-well dishes using cells plated in DMEM with 10% fetal bovine serum one day before the experiment. Cell monolayers were washed twice with Hanks' balanced salt solution (HBSS) containing 25 mM HEPES and were chemically fixed for 30 min at 23° in 10 mM N-hydroxysuccinimide and 30 mM 1-ethyl-3-[3-dimethyl [aminopropyl] carbodiimide, in buffer containing 10 mM HEPES, 140 mM NaCl, 1 mM CaCl$_2$, and 1 mM MgCl$_2$. Monolayers were washed with HBSS containing 25 mM HEPES and the fixative was inactivated by incubating 30 min at 23° in DMEM (without serum) containing 25 mM HEPES. Native PA was added at 1 μg/ml in minimum essential medium containing Hanks' salts, 25 mM HEPES, 1% bovine serum albumin, and a total of 4.5 mM NaHCO$_3$. Cells were incubated overnight at room temperature to allow binding and cleavage of PA. Cells were washed twice in HBSS and mutant LF proteins (0-5000 ng/ml) along with 50 ng/ml $^{125}$I-LF was added to each well. Cells were further incubated for 5 h, washed three times in HBSS, dissolved in 0.5 ml 1N NaOH, and counted in a gamma counter (Beckman Gamma 9000).

Using this assay, the LF mutant proteins having amino-terminal deletions were found incapable of binding to PA, thereby explaining their lack of toxicity. Carboxyl-terminal deleted LF proteins did bind to PA in a dose dependent manner, although they had slightly lower affinity than LF. The proteins deleted in the repeat region could not be tested for competitive binding because their instability prevented purification of intact protein.

The EC$_{50}$ for LF$^{1-254}$.TR.PE$^{362-613}$ binding was found to be 220 ng/ml, which is similar to that of LF, 300 ng/ml. Therefore the binding data correlate well with the toxicity of this construct. In contrast, neither LF$^{1-198}$.TR.PE$^{362-613}$ nor LF$^{1-79}$.TR.PE$^{362-613}$ bound to PA63 on cells, thereby explaining their lack of toxicity.

EXAMPLE 3

Construction of Genes Encoding PA Fusion Proteins

The genes encoding PA (or PA truncated at the carboxyl terminus to abrogate binding to the PA receptor) and an alternative targeting moiety (a single-chain antibody, growth factor, or other cell type-specific domain) are spliced using conventional molecular biological techniques. The PA gene is readily available, and the genes encoding alternative targeting domains are derived as described below.

Single-chain antibodies (sFv)

See Example 4, below.

Growth Factors and Other Targeting Proteins

The nucleotide sequences of genes encoding a number of growth factors and other proteins that are targeted to specific cell types or classes are reported in freely accessible databases (e.g., GenBank), and in many cases the genes are available. In circumstances where this is not the case, genes can be cloned from genomic or cDNA libraries, using probes based on the known nucleotide sequence of the gene that codes for the growth factor, or derived from a partial amino acid sequence of the protein (see, e.g. Sambrook, supra. ). Alternatively, genes encoding the growth factor or other targeting moiety can be produced de novo from chemically synthesized overlapping oligonucleotides, using the preferred codon usage of the expression host. For example, the gene for human epidermal growth factor urogastrone was synthesized from the known amino acid sequence of human urogastrone using yeast preferred codons. The cloned DNA, under control of the yeast GAPDH promoter and yeast ADH-1 terminator, expresses a product having the same properties as natural human urogastrone. The product of this synthesized gene is nearly identical to that of the natural urogastrone, the only difference being that the product of the synthetic gene has a trptophan at amino acid 13, while the other has a tyrosine (Urdea et al. *Proc. Natl. Acad. Sci. USA* 80:7461-7465, 1983).

Expression of PA Fusion Proteins

Once constructed, genes encoding PA-fusion proteins are expressed in *Bacillus anthracis*, and recombinant proteins are purified by one of the following methods: (i) size-based chromatographic separation; (ii) affinity chromatography. In the case of PA-sFv fusions, immobilized metal chelate affinity chromatography may be the purification method of choice, because addition of a string of six histidine residues at the carboxyl terminus of the sFv will have no detrimental effect on binding to antigen. Additional methods of expression of PA-fusion proteins utilize an in vitro rabbit reticulocyte lysate-based coupled transcription/translation system, which has been demonstrated to accurately refold chimeric proteins consisting of an sFv fused to diphtheria toxin, or Pseudomonas exotoxin A as demonstrated in Example 4.

Functional Testing of PA Fusion Proteins

After expression and purification, functionality of PA-fusion proteins are tested by determining their ability to act in concert with an LF-PE fusion protein to inhibit protein synthesis in an appropriate cell line. Using a PA-anti human transferrin receptor sFv fusion as a model, the following properties are examined: (i) Cell type-specificity (protein synthesis should be inhibited in cell lines which express the human transferrin receptor, but not in those which do not); (ii) Independence of toxicity from PA receptor binding (excess free PA should have no effect on toxicity of the PA-sFv/LF-PE complex); (iii) Competitive inhibition by excess free antibody (toxicity should be abrogated in the presence of excess sFv, or the monoclonal antibody from which it was derived). For example such tests are described in Examples 4 and 5. These studies and other studies are used to confirm that PA has been successfully re-routed to an alternative receptor to permit the use of the present anthrax toxin-based cell type-specific cytotoxic agents for the treatment of disease.

EXAMPLE 4

Generating Fusion Proteins with Single-Chain Antibodies Reagents

Methionine-free rabbit reticulocyte lysate-based coupled transcription/translation reagents, recombinant ribonuclease inhibitor (rRNasin), and cartridges for the purification of plasmid DNA were purchased from Promega (Madison, Wis.). Tissue culture supplies were from GIBCO (Grand Island, N.Y.) and Biofluids (Rockville, Md.). OKT9 monoclonal antibody was purchased from Ortho Diagnostic Systems (Raritan, N.J.). PCR reagents were obtained from by Perkin-Elmer Cetus Instruments (Norwalk, Conn.), and restriction and nucleic acid modifying enzymes (including M-MLV reverse transcriptase) were from GIBCO-BRL (Gaithersburg, Md.). A Geneclean kit for the recovery of DNA from agarose gels was supplied by BIO 101 (La Jolla, Calif.). Hybridoma mRNA was isolated using a Fast Trak mRNA isolation kit (Invitrogen, San Diego, Calif.). All isotopes were purchased from Du Pont-New England Nuclear (Boston, Mass.), except [Adenylate-$^{32}$P]NAD, which was supplied by ICN Biomedicals (Costa Mesa, Calif.). Pseudomonas exotoxin A was obtained from List Biologicals (Campbell, Calif.). Oligonucleotides were synthesized on a dual column Milligen-Biosearch Cyclone Plus DNA synthesizer (Burlington, Mass.), and purified using OPC cartridges (Applied Biosystems, Foster City, Calif.). DNA templates were sequenced using a Sequenase II kit (United States Biochemical Corp., Cleveland, Ohio), and SDS-polyacrylamide gel electrophoresis (PAGE) was performed using 10–20% gradient gels (Daiichi, Tokyo, Japan). After electrophoresis, gels were fixed in 10% methanol/7% acetic acid, and soaked in autoradiography enhancer (Amplify, Amersham Arlington Heights, Ill.). After drying, autoradiography was performed overnight using X-OMAT AR2 film (Eastman Kodak, Rochester, N.Y.).

Plasmids

The vector pET-11d is available from Novagen, Inc., Madison, Wis. Plasmids were maintained and propagated in *E. coli* strain XL1-Blue (Stratagene, La Jolla, Calif.).

Cell Lines

K562, a human erythroleukemia-derived cell line [ATCC CCL 243] known to express high levels of the human transferrin receptor at the cell surface, was cultured in RPMI 1640 medium containing 24 mM NaHCO$_3$, 10% fetal calf serum, 2 mM glutamine, 1 mM sodium pyruvate, 0.1 mM nonessential amino acids, and 10 μg/ml gentamycin. An African green monkey kidney line, Vero (ATCC CCL 81), was grown in Dulbecco's modified Eagle's medium (DMEM) supplemented as indicated above. The OKT9 hybridoma (ATCC CRL 8021), which produces a MoAb (IgG1) reactive to the human transferrin receptor, was maintained in Iscove's modified Dulbecco's medium containing 20% fetal calf serum, in addition to the supplements described above. All cell lines were cultured at 37° C. in a 5% CO$_2$ humidified atmosphere.

Construction of sFv from Hybridomas

Antibody V$_L$ and V$_H$ genes were cloned using a modification of a previously described technique (Larrick et al. *Biotechniques* 7:360, 1989; Orlandi et al. *Proc. Natl. Acad. Sci. USA* 86:3833, 1989; Chaudhary et al., 1990). Briefly, mRNA was isolated from 1×10$^8$ antibody producing hybridoma cells, and approximately 3 μg was reverse transcribed with M-MLV reverse transcriptase, using random hexanucleotides as primers. The resulting cDNA was screened with two sets of PCR primer pairs designed to ascertain from which Kabat gene family the heavy and light chains were derived (Kabat et al. *Sequences of proteins of immunological interest*. Fifth Edition. (Bethesda, Maryland: U.S. Public Health Service, 1991). Having identified the most effective primer pairs, cDNA's encoding V$_L$ and V$_H$ were spliced, separated by a region encoding a 15 amino acid peptide linker, using a previously described PCR technique known as gene splicing by overlap extension (SOE) (Johnson & Bird *Methods Enzymol*. 203:88, 1991). The sFv gene was then cloned into pET-11d, in frame and on the 5'-side of the PE40 gene, such that expression of the construct should generate an sFv-PE40 fusion protein approximately 70 kDa in size.

Design of Primers for PCR Amplification of V Regions Genes

The first and third complementarity determining regions (CDRs) of terminally rearranged immunoglobulin variable region genes are flanked by conserved sequences (the first framework region, FR1 on the 5' side of CDR1, and the fourth framework region, FR4, on the 3' side of CDR3).

Although murine variable region genes have been successfully cloned, regardless of family, with just two pairs of highly degenerate primers (one pair for V$_L$ and another for V$_H$) (Gussow et al. *Cold Spring Harbor Symp. Quant. Biol.* 54:265, 1989; Orlandi et al., 1989; Chaudhary et al., 1990; Batra et al., 1991), the method may not be effective in cases where the number of mismatches between primers and the target sequence is extensive. With this in mind, using the Kabat database of murine V gene sequences the present invention provides a set of ten FR1-derived primers (six for V$_L$ and four for V$_H$), such that any of the database sequences selected at random would have a maximum of three mismatches with the most homologous primer. This set of primers can be used effectively to clone V region genes from a number of MoAb secreting cell lines.

Assembly of the OKT9 sFv Gene mRNA isolated from the hybridoma secreting the OKT9 MoAb was converted to cDNA as described previously (Larrick et al., 1989; Orlandi et al., 1989; Chaudhary et al., 1990). Despite the fact that CL-UNI is the partnering oligonucleotide in each case, a product the required size (approximately 400 bp) is not produced by V$_L$ primers IV/VI, IIa or IIb. This suggests that mismatches between these primers and the target sequence were too extensive to allow efficient amplification. A similar argument can be used to explain the failure of V$_H$ primers I and III to produce the required product. It is clear that primers V$_L$-I/III and V$_H$-V are most effective at amplifying the OKT9 $V_L$ and $V_H$ genes respectively. PCR amplified OKT9 $V_L$ and $V_H$ genes were spliced together using the SOE technique, as previously described (Johnson & Bird, 1991). A synthetic DNA sequence encoding a 15 amino acid linker, was inserted between the variable regions; this linker has been used very effectively in the production of functional sFv (Huston et al., 1991; Johnson & Bird, 1991), and appears to allow the variable chains to assume the optimum orientation for antigen binding. Following splicing of V region genes by the SOE procedure, the DNA fragment encoding the OKT9 sFv was electrophoresed through a 1.5% agarose gel, purified by the Geneclean technique, digested with the appropriate pair of restriction enzymes, and cloned into the pET-11d expression vector in frame and on the 5' side of the PE40 gene.

In Vitro Expression of sFv-PE40 Fusion Proteins

Plasmid templates were transcribed and translated using a rabbit reticulocyte lysate-based transcription/translation system, according to the instructions of the manufacturer, in 96-well microtiter plate format L-[$^{35}$S]methionine-labeled proteins (for analysis by SDS-PAGE) and unlabeled proteins (for enzymatic analysis and bioassay), were produced in similar conditions, except that the isotope was replaced with 20 µM unlabeled L-methionine in the latter case. Control lysate was produced by adding all reagents except plasmid DNA. After translation, unlabeled samples were dialysed overnight at 4° C. against phosphate-buffered saline (PBS), pH 7.4 in Spectra/Por 6 MWCO (molecular weight cutoff) 50,000 tubing (Spectrum, Houston, Tex.).

Constructs incorporating the aberrant kappa transcript will contain a translation termination codon in the $V_L$ chain as previously described, and would therefore be expected to generate a translation product approximately 12 kDa in size. On the other hand, constructs which have incorporated the productive $V_L$ gene contain no such termination codon, and a full-length fusion protein (approximately 70 kDa in size) should be produced.

In vitro expression studies were used to determine the size of the protein encoded by the OKT9 sFv-PE40 gene. The constructs tested in this experiment clearly produce a protein of approximately 70 kDa, indicating that the clones do not contain the aberrant $V_L$ gene, and are devoid of frameshift mutations. Of several OKT9 sFv constructs tested, none apparently incorporated the incorrect VL gene. However, in the case of another sFv generated by this method (1B7 sFv, derived from a MoAb which binds to pertussis toxin), the majority of the clones tested produced a 12 kDa protein, and were found to contain the aberrant transcript on DNA sequencing. It should be noted that the 12 kDa fragment is frequently obscured in 10–20% gradient gels by unincorporated $^{35}$S-methionine which co-migrates with the dye front.

Determination of Protein Concentration

The enzymatic activities of fusion proteins were compared with those of known concentrations of PE in an ADP-ribosyl transferase assay, allowing molarities to be determined (Johnson et al. *J. Biol. Chem.* 263:1295–1399, 1988). Samples were adjusted to contain equivalent concentrations of lysate, thus maintaining an identical amount of substrate (elongation factor 2) in all cases.

Protein Synthesis Inhibition Assay for Functional sFv-PE40 Binding

Binding of the OKT9 sFv to the human transferrin receptor was qualitatively determined by assessing the ability of the OKT9 sFv-PE40 fusion protein to inhibit protein synthesis in the K562 cell line. Pseudomonas exotoxin A is a bacterial protein which is capable of inhibiting de novo protein synthesis in a variety of eukaryotic cell types. The toxin binds to the cell surface, and ultimately translocates to the cytosol where it enzymatically inactivates elongation factor 2. PE40 is a mutant form of exotoxin A which lacks a binding domain, but is enzymatically active, and capable of translocation. Fusion proteins containing PE40 and an alternative binding domain (for example, an sFv to a cell surface receptor) will inhibit protein synthesis in an appropriate cell line only if the sFv binds to a cell-surface antigen which subsequently internalizes into an acidified endosome (Chaudhary et al., 1989). The TfnR is such an antigen, so a qualitative assessment of binding may be determined by measuring the ability of the OKT9 sFv-PE40 fusion protein to inhibit protein synthesis in a cell line like K562, which expresses the TfnR. Protein synthesis inhibition assays were performed as described previously (Johnson et al., 1988). Briefly, samples were serially diluted in ice cold PBS, 0.2% BSA, and 11 µl volumes were added to the appropriate well of a 96-well microtiter plate (containing $10^4$ cells/100 µl/well in leucine-free RPMI 1640). After carefully mixing the contents of each well, the plate was incubated for the indicated time at 37° C. in a 5% $CO_2$ humidified atmosphere. Each well was then pulsed with 20 µl of L-[$^{14}$C(U)]leucine (0.1 µCi/20 µl), incubated for 1 hour, and harvested onto glass fiber filters using a PHD cell harvester (Cambridge Technology, Cambridge, Mass.). Results are expressed as a percentage of the isotope incorporation in cells treated with appropriate concentrations of control dialyzed lysate.

The results of this assay, clearly indicate that OKT9 sFv-PE40 is capable of inhibiting protein synthesis with an $IC_{50}$ (the concentration of a reagent which inhibits protein synthesis by 50%) of approximately $2 \times 10^{-9}$M. The toxicity of the fusion protein, but not of PE, was abrogated in the presence of excess OKT9 MoAb (12 µg/ml), indicating that binding is specific for the TfnR. No toxicity was observed when K562 was substituted with Vero (an African Green monkey cell line which expresses the simian version of the transferrin receptor), indicating that the OKT9 sFv retains the human receptor-specific antigen binding properties of the parent antibody.

Having demonstrated binding of the OKT9 sFv to TfnR, its nucleotide sequence was determined using dideoxynucleotide chain-terminating methods, confirming extensive homology with the respective regions of immunoglobulins of known sequence.

EXAMPLE 5

Characterization of Single-Chain Antibody (sFv)-Toxin Fusion Proteins Produced in Vitro in Rabbit Reticulocyte Lysate The present invention provides in vitro production of proteins containing a toxin domain (derived from Diphtheria toxin (DT) or PE) fused to a domain encoding a single-chain antibody directed against the human transferrin receptor (TfnR). The expression of this antigen on the cell surface is coordinately regulated with cell growth; TfnR exhibits a limited pattern of expression in normal tissue, but is widely distributed on carcinomas and sarcomas (Gatter, et al. *J. Clin. Pathol.* 36:539–545, 1983), and may therefore be a suitable target for immunotoxin-based therapeutic strategies (Johnson, V. G. and Youle, R. J. "Intracellular Trafficking of Proteins" Cambridge Univ. Press, Cambridge England, Steer and Hover eds., pp. 183–225; Batra et al., 1991; Johnson et al., 1988).

Proteins consisting of a fusion between an sFv directed against the TfnR and either the carboxyl-terminus 40 kDa of PE, or the DT mutant CRM 107 [S(525)F] were expressed in rabbit reticulocyte lysates, and found to be specifically cytotoxic to K562, a cell line known to express TfnR. In comparison, a chimeric protein consisting of a fusion between a second DT mutant, DTM1 [S(508)F, S(525)F] and the E6 sFv exhibited significantly lower cytotoxicity. Legal restrictions imposed on manipulating toxin genes in vivo previously prevented expression of potentially interesting toxin-containing fusion proteins (*Federal Register* 51(88)(III):16961 and Appendix F:16971); the present invention provides a novel procedure for in vitro gene construction and expression which satisfies the regulatory requirements, facilitating the first study of the potential of non-truncated DT mutants in fusion protein ITs. The present data also demonstrates that functional recombinant antibodies can be generated in vitro.

Reagents

DT and PE were purchased from List Biologicals (Campbell, Calif.). Nuclease treated, methionine-free rabbit reticulocyte lysate and recombinant ribonuclease inhibitor (rRNasin) were obtained from Promega (Madison, Wis.). Tissue culture supplies were from GIBCO (Grand Island, N.Y.) and Biofluids (Rockville, Md.). Reagents for PCR were provided by Perkin-Elmer Cetus (Norwalk, Conn.). Restriction and nucleic acid modifying enzymes were from Stratagene (La Jolla, Calif.), as was the mCAP kit used to produce capped mRNA in vitro. Geneclean and RNaid kits (for the purification of DNA and RNA respectively) were supplied by BIO 101 (La Jolla, Calif.). L-[$^{35}$S]methionine, L-[$^{14}$C(U)]leucine and 5'-(alpha-thio)-[$^{35}$S]dATP were from New England Nuclear (Boston, Mass.). [Adenylate-$^{32}$P] NAD was supplied by ICN Biomedicals (Costa Mesa, Calif.).

Oligonucleotide Synthesis

Oligonucleotides were synthesized (0.2 µM scale), using cyanoethylphosphoramidites supplied by Milligen-Biosearch (Burlington, Mass.) on a dual column Cyclone Plus DNA synthesizer. Post-synthesis purification was achieved using OPC cartridges (Applied Biosystems, Foster City, Calif.).

Plasmids pET-11d was the generous gift of Dr. F. William Studier, Brookhaven National Laboratory (Upton, N.Y.). pHB21-PE40, a derivative of pET-11d containing the gene for PE40, was kindly supplied by Dr. David FitzGerald (NIH, Bethesda, Md.). All plasmids were maintained and propagated in *E. coli* strain XL1-Blue (Stratagene, La Jolla, Calif.).

Cell Lines

*Corynebacterium diphtheriae* strain C7$_s$(β)$^{tox+}$(ATCC 27012) was obtained from the ATCC (Rockville, Md.), and the strain producing the binding-deficient DT mutant CRM 103 was the generous gift of Dr. Neil Groman, University of Washington (Seattle, Wash.). Both strains were propagated in LB broth. K562 (a human erythroleukemia-derived cell line, ATCC CCL 243) was cultured in RPMI 1640 medium containing 24 mM NaHCO$_3$, 10% fetal calf serum, 2 mM glutamine, 1 mM sodium pyruvate, 0.1 mM nonessential amino acids, and 10 µg/ml gentamycin. Vero (an African green monkey kidney line, ATCC CCL 81) was grown in Dulbecco's modified Eagle's medium supplemented as described above. All eukaryotic cells were cultured at 37° C. in a 5% CO$_2$ humidified atmosphere.

Splicing Genes using PCR

Genes encoding antibody V$_L$ and V$_H$ were spliced, separated by a region encoding a 15 amino acid peptide linker, using a previously described PCR technique known as gene splicing by overlap extension (SOE) (Horton et al. *Gene* 77:61–68, 1989; Horton et al. *Biotechniques* 8:528–535, 1990). For studies requiring in vitro expression of PCR products, tox gene-derived fragments were linked to those encoding sFv using a similar method, without the use of restriction enzymes.

Construction of Plasmids Encoding Toxin-sFv Fusion Proteins

The gene encoding PE40 was obtained as an insert in pET-11d, and the sFv gene was cloned on the 5' side of this insert as indicated. To clone the gene encoding the DT binding-site mutant DTM1 [S(508)F, S(525)F], genomic DNA was isolated from the *C. diphtheriae* strain which produces CRM 103. DNA was extracted by a modification of the cetyltrimethylammonium bromide extraction procedure (Wilson, K. "Current Protocols in Molecular Biology" Asubel et al. eds. John Wiley & Sons New York, 2.4.1–2.4.5, 1988) and subjected to 20 cycles of PCR amplification. Primers were designed to: (i) amplify the 1605 bp region encoding CRM 103, concomitantly mutating the codon at position 525 from TCT to TTT, and (ii) incorporate restriction sites appropriate for cloning. The mutations present in CRM 107 and CRM 103 were thus combined on a single gene.

In Vitro Transcription of DNA Templates

For transcription, DNA templates required a T7 RNA polymerase promoter immediately upstream of the gene of interest (Oakley, J. L. and Coleman, J. E. *Proc. Acad. Sci. U.S.A.* 74:4266–4270, 1977). Such a promoter was conveniently present in pET-11d (Studier et al. *Enzymol* 185:60–89, 1990). In the case of PCR products, the upstream primer (a 57-mer, T7-DT) was used to introduce all of the elements necessary for in vitro transcription/translation. T7-DT includes a consensus T7 RNA polymerase promoter, together with the first seven codons of mature DT (Greenfield et al. *Proc. Natl. Acad. Sci. U.S.A.* 80:6853–6857, 1983) immediately preceded by an ATG translation initiation codon in the optimum Kozak context (Kozak, M. *J. Biol. Chem.* 266:19867–19870, 1991). m$^7$G (5')ppp(5')G-capped RNA was produced by transcription from linearized plasmids or PCR products using an mCAP kit, according to the manufacturer's protocol. Prior to translation, RNA was purified using an RNaid kit, recovered in nuclease free water, and analyzed by formaldehyde gel electrophoresis.

In Vitro Expression of Fusion Proteins

L-[$^{35}$S]methionine-labelled proteins (for analysis by SDS-PAGE) were produced from capped RNA in methionine-free, nuclease treated rabbit reticulocyte lysate, according to the supplier's instructions. Unlabeled proteins (for bioassay), were produced in similar conditions, except that the isotope was replaced with 20 µM unlabeled L-methionine. Control lysate was produced by adding all reagents except exogenous RNA. After translation, samples were dialysed overnight at 4° C. against PBS, pH 7.4 in Spectra/Por 6 MWCO 50,000 tubing (Spectrum, Houston, Tex.).

Prior to transcription, plasmids were linearized at the BglII site and treated with proteinase K to destroy ribonucleases that may contaminate the sample. After phenol/chloroform extraction and ethanol precipitation, DNA was dissolved in nuclease free water to a concentration of approximately 0.2 µg/µl. m$^7$G(5')ppp(5')G-capped RNA was synthesized by T7 RNA polymerase using the conditions recommended by the manufacturer, and its integrity was confirmed by formaldehyde gel electrophoresis. Capped RNA was translated in a commercially available rabbit reticulocyte lysate, according to the instructions of the manufacturer. It is clear from the gel that the major band in each case has a molecular weight corresponding to that of the protein of interest, and that relatively large molecules (approximately 120 kDa in the case of DTM1-E6 sFv-PE40) can be synthesized in the lysate using the conditions described.

Immediately following translation, samples were extensively dialyzed overnight at 4° C. against PBS, pH 7.4. The dialysis step was found to be essential, because non-dialyzed rabbit reticulocyte lysate resulted in the incorporation of significantly lower amounts of $^{14}$C-leucine upon assay by protein synthesis inhibition in all cell lines tested. After determining the concentration of the newly synthesized protein using a standard assay for measuring ADP-ribosyltransferase activity (Johnson et al., 1988), the cytotoxic activity of samples was immediately determined.

ADP-ribosyl Transferase Assay

The enzymatic activity (and therefore molarity) of fusion proteins was determined by comparison with DT or PE standard curves, as described previously (Johnson et al., 1988). Appropriate volumes of control lysate were added to each standard curve sample, in order to control for the presence of significant levels of EF-2 in reticulocyte lysate.

Other Methods

SDS-PAGE was performed as previously described (Laemmli, U. K. *Nature* 227:680–685, 1970), using 10–20% gradient gels (Daiichi, Tokyo, Japan). Once electrophoresis was complete, gels were fixed for 15 minutes in 10% methanol, 7% acetic acid, and then soaked for 30 minutes in autoradiography enhancer (Amplify, Amersham Arlington Heights, IL). After drying, autoradiography was performed overnight using X-OMAT AR2 film (Eastman Kodak, Rochester, N.Y.), in the absence of intensifying screens. Dideoxynucleotide chain-termination sequencing of double-stranded DNA templates was performed using a Sequenase II kit (United States Biochemical Corp., Cleveland, Ohio), according to the manufacturer's protocol.

Cytotoxicity of Toxin-sFv Fusion Proteins Expressed in Reticulocyte Lysates

The cytotoxic activity of fusion proteins was determined by their ability to inhibit protein synthesis in relevant cell lines (e.g., K562). Assays were performed as described previously (Johnson et al., 1988). Briefly, samples were serially diluted in ice cold PBS, 0.2% BSA, and 11 µl volumes were added to the appropriate well of a 96-well microtiter plate (containing 10$^4$ cells/well in leucine-free RPMI 1640). After carefully mixing the contents of each well, the plate was incubated for the indicated time at 37° C. in a 5% CO$_2$ humidified atmosphere. Each well was then pulsed with 20 µl of L-[$^{14}$C(U)]leucine (0.1 µCi/20 µl), incubated for 1 hour, and harvested onto glass fiber filters using a PHD cell harvester (Cambridge Technology, Cambridge, Mass.). Results were expressed as a percentage of the isotope incorporation in cells treated with appropriate concentrations of control dialyzed lysate.

The results of the protein synthesis inhibition assay clearly indicate that PE40-containing fusion proteins synthesized in cell-free reticulocyte lysates are highly cytotoxic to this cell line (IC$_{50}$ 1×10$^{-10}$M). In contrast, DTM1-E6 sFv was at least ten-fold less toxic to K562 than the PE40-containing fusion protein, despite the fact that it exhibited ADP-ribosyl transferase activity indistinguishable from that of wt DT synthesized from an equivalent amount of RNA in an identical reticulocyte lysate mix. Since the decreased toxicity of DTM1-E6 sFv is clearly not due to a deficit in enzymatic activity, the binding and/or translocation process is implicated. Possible mechanisms by which the sFv-antigen interaction could be inhibited include: (i) misfolding of the sFv domain or (ii) steric interactions with other regions of the fusion protein preventing close association of sFv with the TfnR. It is of interest that a tripartite protein, DTM1-E6 sFv-PE40 was significantly cytotoxic to K562 (IC$_{50}$ around 1×10$^{-10}$M, similar to that of PE40-E6 sFv), and the toxic effect was clearly mediated via the TfnR, since this activity was blocked by addition of excess E6 Mab. Although it is possible that the inclusion of the PE40 moiety at the carboxyl end of the tripartite molecule results in a significant conformational change in domains more proximal to the amino terminus, it seems unlikely that the sFv binding domain of DTM1-E6 is misfolded, or unavailable to interact with the TfnR. Interactions of DTM1-E6 sFv with the cell surface could be measured in a direct binding assay (Greenfield et al. *Science* 238:536–539, 1987), but these studies were not performed in the course of this investigation. Nevertheless, it appears likely that the lack of toxicity of the DTM1-E6 sFv fusion protein is due to a deficit in its translocation function.

The expression system developed is rapid and easy, and facilitates the manipulation of a number of samples at once. No complicated protein purification or refolding procedures are required, and the method can be used to express proteins which, due to restrictions imposed on the manipulation of toxin-encoding genes, could not be produced by more conventional methods. The technique is ideal for ascertaining the suitability of new sFv for IT development; it is theoretically possible to assemble the sFv-encoding gene (and that encoding the IT itself) by splicing of PCR products derived directly from the hybridoma, without the necessity for cloning. This would facilitate the selection of the most promising candidate molecule, prior to investing considerable effort and expense in large scale protein production and purification. Toxins and toxin-containing fusion proteins are proving to be powerful aids in our understanding of receptor mediated endocytosis and intracellular routing, and are providing valuable insight into normal cell function (reviewed in ref. 2). The method described simplifies the generation of such molecules, and facilitates their production and use in laboratories in which the application of more conventional expression methods would be impractical.

EXAMPLE 6

Cassette Mutagenesis to Produce PAHIV Mutants

Three pieces of DNA are joined together. Piece A has vector sequences and encodes the "front half" (5' end of the gene) of PA protein, B is short piece of DNA (referred to as a cassette) and encodes a small middle piece of PA protein and piece C which encodes the "back half" (3' end of the gene) of PA.

PA with alternate HIV-1 cleavage sites were created by a cassette mutagenesis procedure. Eight deoxyoligonucleotides were synthesized for construction of cassettes coding for specifically designed amino acid sequences. All four cassettes were generated by annealing two synthetic oligonucleotides (primers).

| | |
|---|---|
| Primer 1A CG CAA GTA TCA CAA AAT TAT CCG ATC GTG CAA AAC ATA CTG CAG G | (SEQ ID NO: 18) |
|         Q   V   S   Q   N   Y   P   I   V   Q   N   I   L   Q | (SEQ ID NO: 19) |
| Primer 1B G TTC CTG CAG TAT GTT TTG CAC GAT CGG ATA ATT TTG TGA TAC TTG | (SEQ ID NO: 20) |
| Primer 2A CG AAC ACT GCC ACT ATC ATG ATG CAA CGT GGT AAT TTT CTG CAG G | (SEQ ID NO: 21) |
|         N   T   A   T   I   M   M   Q   R   G   N   F   L   Q | (SEQ ID NO: 22) |
| Primer 2B G TCC CTG CAG AAA ATT ACC ACG TTG CAT CAT GAT AGT GGC AGT GTT | (SEQ ID NO: 23) |
| Primer 3A CG ACT GTC TCT TTT AAC TTC CCG CAA ATC ACG CTT TGG CTG CAG G | (SEQ ID NO: 24) |
|         T   V   S   F   N   F   P   Q   I   T   L   W   L   Q | (SEQ ID NO: 25) |
| Primer 3B G TCC CTG CAG CCA AAG CGT GAT TTG CGG GAA GTT AAA AGA GAC AGT | (SEQ ID NO: 26) |
| Primer 4A CG GGC GGT TCT GCC TTT AAC TTC CCG ATC GTC ATG GGA GGT CTG CAG G | (SEQ ID NO: 27) |
|         G   G   S   A   F   N   F   P   I   V   M   G   G   L   Q | (SEQ ID NO: 28) |
| Primer 4B G TCC CTG CAG ACC TCC CAT GAC GAT CGG GAA GTT AAA GGC AGA ACC GCC | (SEQ ID NO: 29) |

The underlined portion of each protein sequence is recognized and cleaved by the HIV-1 protease.

Primer pair 1 encodes a protein sequence which duplicates part of the cleavage site found between the membrane associated protein and the capsid protein.

Primer pair 2 encodes a protein sequence which duplicates part of the cleavage site between the capsid and the nucleocapsid protein.

Primer pair 3 encodes a protein sequence which duplicates part of the cleavage site between the protease and the p6 protein. Like the protease, p6 is a portion of the large protein produced by HIV.

Primer pair 4 encodes a protein sequence which should be cleaved by the protease. It was created by examining several protein sequences which are recognized by the HIV protease and using the common residues from each sequence. Glycine residues were added to each end to make the molecule more flexible.

The mutagenic cassettes were ligated with the BamHI/BstBI fragment from plasmid pYS5 and the PpuMI-BamI-II fragment from plasmid pYS6. Plasmids shown to have correct restriction maps were transformed into the *E. coli* dam– dcm– strain GM2163 (available from New England Bio-Labs, Beverly, Mass.). Unmethylated plasmid DNA was purified from each mutant and used to transform *B. anthracis*. For methods, see Klimpel, et al. *Proc. Natl. Acad. Sci.* 89:10277–10281 (1992). pYS5 and pYS6 construction are described in Singh, et al. *J. Bio. Chem.* 264:19103–19107 (1989).

The nucleotide and amino acid sequence of the mature PA protein after alteration with primer set 2 are shown below. Nucleotides residues 482 to 523 were replaced with cassette 2 resulting in replacement of amino acid residues 162–171 of PA with residues NTATIMMQRGNFLQ (SEQ. ID NO: 22), PAHIV#2. The altered DNA sequence and the new amino acid residues are underlined.

Sequence Range: 1 to 2220
Nucleic acid sequences = (SEQ ID NO: 30); Amino acid sequence = (SEQ ID NO: 31)

```
                                                                                            60
                                                                                             *
GAA GTT AAA CAG GAG AAC CGG TTA TTA AAT GAA TCA GAA TCA AGT TCC CAG GGG TTA CTA
CTT CAA TTT GTC CTC TTG GCC AAT AAT TTA CTT AGT CTT AGT TCA AGG GTC CCC AAT GAT
Glu Val Lys Gln Glu Asn Arg Leu Leu Asn Glu Ser Glu Ser Ser Ser Gln Gly Leu Leu>
                                                                                           120
                                                                                             *
GGA TAC TAT TTT AGT GAT TTG AAT TTT CAA GCA CCC ATG GTG GTT ACC TCT TCT ACT ACA
CCT ATG ATA AAA TCA CTA AAC TTA AAA GTT CGT GGG TAC CAC CAA TGG AGA AGA TGA TGT
Gly Tyr Tyr Phe Ser Asp Leu Asn Phe Gln Ala Pro Met Val Val Thr Ser Ser Thr Thr>
                                                                                           180
                                                                                             *
GGG GAT TTA TCT ATT CCT AGT TCT GAG TTA GAA AAT ATT CCA TCG GAA AAC CAA TAT TTT
CCC CTA AAT AGA TAA GGA TCA AGA CTC AAT CTT TTA TAA GGT AGC CTT TTG GTT ATA AAA
Gly Asp Leu Ser Ile Pro Ser Ser Glu Leu Glu Asn Ile Pro Ser Glu Asn Gln Tyr Phe>
                                                                                           240
                                                                                             *
CAA TCT GCT ATT TGG TCA GGA TTT ATC AAA GTT AAG AAG AGT GAT GAA TAT ACA TTT GCT
GTT AGA CGA TAA ACC AGT CCT AAA TAG TTT CAA TTC TTC TCA CTA CTT ATA TGT AAA CGA
Gln Ser Ala Ile Trp Ser Gly Phe Ile Lys Val Lys Lys Ser Asp Glu Tyr Thr Phe Ala>
                                                                                           300
                                                                                             *
ACT TCC GCT GAT AAT CAT GTA ACA ATG TGG GTA GAT GAC CAA GAA GTG ATT AAT AAA GCT
TGA AGG CGA CTA TTA GTA CAT TGT TAC ACC CAT CTA CTG GTT CTT CAC TAA TTA TTT CGA
Thr Ser Ala Asp Asn His Val Thr Met Trp Val Asp Asp Gln Glu Val Ile Asn Lys Ala>
                                                                                           360
                                                                                             *
TCT AAT TCT AAC AAA ATC AGA TTA GAA AAA GGA AGA TTA TAT CAA ATA AAA ATT CAA TAT
AGA TTA AGA TTG TTT TAG TCT AAT CTT TTT CCT TCT AAT ATA GTT TAT TTT AAG TTA ATA
Ser Asn Ser Asn Lys Ile Arg Leu Glu Lys Gly Arg Leu Tyr Gln Ile Lys Ile Gln Tyr>
                                                                                           420
                                                                                             *
CAA CGA GAA AAT CCT ACT GAA AAA GGA TTG GAT TTC AAG TTG TAC TGG ACC GAT TCT CAA
```

-continued

Sequence Range: 1 to 2220
Nucleic acid sequences = (SEQ ID NO: 30); Amino acid sequence = (SEQ ID NO: 31)

| GTT | GCT | CTT | TTA | GGA | TGA | CTT | TTT | CCT | AAC | CTA | AAG | TTC | AAC | ATG | ACC | TGG | CTA | AGA | GTT |
|-----|-----|-----|-----|-----|-----|-----|-----|-----|-----|-----|-----|-----|-----|-----|-----|-----|-----|-----|-----|
| Gln | Arg | Glu | Asn | Pro | Thr | Glu | Lys | Gly | Leu | Asp | Phe | Lys | Leu | Tyr | Trp | Thr | Asp | Ser | Gln> |

480

| AAT | AAA | AAA | GAA | GTG | ATT | TCT | AGT | GAT | AAC | TTA | CAA | TTG | CCA | GAA | TTA | AAA | CAA | AAA | TCT |
| TTA | TTT | TTT | CTT | CAC | TAA | AGA | TCA | CTA | TTG | AAT | GTT | AAC | GGT | CTT | AAT | TTT | GTT | TTT | AGA |
| Asn | Lys | Lys | Glu | Val | Ile | Ser | Ser | Asp | Asn | Leu | Gln | Leu | Pro | Glu | Leu | Lys | Gln | Lys | Ser> |

540

| TCG | AAC | ACT | GCC | ACT | ATC | ATG | ATG | CAA | CGT | GGT | AAT | TTT | CTG | CAG | GGA | CCT | ACG | GTT | CCA |
| AGC | TTG | TGA | CGG | TGA | TAG | TAC | TAC | GTT | GCA | CCA | TTA | AAA | GAC | GTC | CCT | GGA | TGC | CAA | GGT |
| Ser | Asn | Thr | Ala | Thr | Ile | Met | Met | Gln | Arg | Gly | Asn | Phe | Leu | Gln | Gly | Pro | Thr | Val | Pro> |

600

| GAC | CGT | GAC | AAT | GAT | GGA | ATC | CCT | GAT | TCA | TTA | GAG | GTA | GAA | GGA | TAT | ACG | GTT | GAT | GTC |
| CTG | GCA | CTG | TTA | CTA | CCT | TAG | GGA | CTA | AGT | AAT | CTC | CAT | CTT | CCT | ATA | TGC | CAA | CTA | CAG |
| Asp | Arg | Asp | Asn | Asp | Gly | Ile | Pro | Asp | Ser | Leu | Glu | Val | Glu | Gly | Tyr | Thr | Val | Asp | Val> |

660

| AAA | AAT | AAA | AGA | ACT | TTT | CTT | TCA | CCA | TGG | ATT | TCT | AAT | ATT | CAT | GAA | AAG | AAA | GGA | TTA |
| TTT | TTA | TTT | TCT | TGA | AAA | GAA | AGT | GGT | ACC | TAA | AGA | TTA | TAA | GTA | CTT | TTC | TTT | CCT | AAT |
| Lys | Asn | Lys | Arg | Thr | Phe | Leu | Ser | Pro | Trp | Ile | Ser | Asn | Ile | His | Glu | Lys | Lys | Gly | Leu> |

720

| ACC | AAA | TAT | AAA | TCA | TCT | CCT | GAA | AAA | TGG | AGC | ACG | GCT | TCT | GAT | CCG | TAC | AGT | GAT | TTC |
| TGG | TTT | ATA | TTT | AGT | AGA | GGA | CTT | TTT | ACC | TCG | TGC | CGA | AGA | CTA | GGC | ATG | TCA | CTA | AAG |
| Thr | Lys | Tyr | Lys | Ser | Ser | Pro | Glu | Lys | Trp | Ser | Thr | Ala | Ser | Asp | Pro | Tyr | Ser | Asp | Phe> |

780

| GAA | AAG | GTT | ACA | GGA | CGG | ATT | GAT | AAG | AAT | GTA | TCA | CCA | GAG | GCA | AGA | CAC | CCC | CTT | GTG |
| CTT | TTC | CAA | TGT | CCT | GCC | TAA | CTA | TTC | TTA | CAT | AGT | GGT | CTC | CGT | TCT | GTG | GGG | GAA | CAC |
| Glu | Lys | Val | Thr | Gly | Arg | Ile | Asp | Lys | Asn | Val | Ser | Pro | Glu | Ala | Arg | His | Pro | Leu | Val> |

840

| GCA | GCT | TAT | CCG | ATT | GTA | CAT | GTA | GAT | ATG | GAG | AAT | ATT | ATT | CTC | TCA | AAA | AAT | GAG | GAT |
| CGT | CGA | ATA | GGC | TAA | CAT | GTA | CAT | CTA | TAC | CTC | TTA | TAA | TAA | GAG | AGT | TTT | TTA | CTC | CTA |
| Ala | Ala | Tyr | Pro | Ile | Val | His | Val | Asp | Met | Glu | Asn | Ile | Ile | Leu | Ser | Lys | Asn | Glu | Asp> |

900

| CAA | TCC | ACA | CAG | AAT | ACT | GAT | AGT | GAA | ACG | AGA | ACA | ATA | AGT | AAA | AAT | ACT | TCT | ACA | AGT |
| GTT | AGG | TGT | GTC | TTA | TGA | CTA | TCA | CTT | TGC | TCT | TGT | TAT | TCA | TTT | TTA | TGA | AGA | TGT | TCA |
| Gln | Ser | Thr | Gln | Asn | Thr | Asp | Ser | Glu | Thr | Arg | Thr | Ile | Ser | Lys | Asn | Thr | Ser | Thr | Ser> |

960

| AGG | ACA | CAT | ACT | AGT | GAA | GTA | CAT | GGA | AAT | GCA | GAA | GTG | CAT | GCG | TCG | TTC | TTT | GAT | ATT |
| TCC | TGT | GTA | TGA | TCA | GTT | CAT | GTA | CCT | TTA | CGT | CTT | CAC | GTA | CGC | AGC | AAG | AAA | CTA | TAA |
| Arg | Thr | His | Thr | Ser | Glu | Val | His | Gly | Asn | Ala | Glu | Val | His | Ala | Ser | Phe | Phe | Asp | Ile> |

1020

| GGT | GGG | AGT | GTA | TCT | GCA | GGA | TTT | AGT | AAT | TCG | AAT | TCA | AGT | ACG | GTC | GCA | ATT | GAT | CAT |
| CCA | CCC | TCA | CAT | AGA | CGT | CCT | AAA | TCA | TTA | AGC | TTA | AGT | TCA | TGC | CAG | CGT | TAA | CTA | GTA |
| Gly | Gly | Ser | Val | Ser | Ala | Gly | Phe | Ser | Asn | Ser | Asn | Ser | Ser | Thr | Val | Ala | Ile | Asp | His> |

1080

| TCA | CTA | TCT | CTA | GCA | GGG | GAA | AGA | ACT | TGG | GCT | GAA | ACA | ATG | GGT | TTA | AAT | ACC | GCT | GAT |
| AGT | GAT | AGA | GAT | CGT | CCC | CTT | TCT | TGA | ACC | CGA | CTT | TGT | TAC | CCA | AAT | TTA | TGG | CGA | CTA |
| Ser | Leu | Ser | Leu | Ala | Gly | Glu | Arg | Thr | Trp | Ala | Glu | Thr | Met | Gly | Leu | Asn | Thr | Ala | Asp> |

1140

| ACA | GCA | AGA | TTA | AAT | GCC | AAT | ATT | AGA | TAT | GTA | AAT | ACT | GGG | ACG | GCT | CCA | ATC | TAC | AAC |
| TGT | CGT | TCT | AAT | TTA | CGG | TTA | TAA | TCT | ATA | CAT | TTA | TGA | CCC | TGC | CGA | GGT | TAG | ATG | TTG |
| Thr | Ala | Arg | Leu | Asn | Ala | Asn | Ile | Arg | Tyr | Val | Asn | Thr | Gly | Thr | Ala | Pro | Ile | Tyr | Asn> |

1200

| GTG | TTA | CCA | ACG | ACT | TCG | TTA | GTG | TTA | GGA | AAA | AAT | CAA | ACA | CTC | GCG | ACA | ATT | AAA | GCT |
| CAC | AAT | GGT | TGC | TGA | AGC | AAT | CAC | AAT | CCT | TTT | TTA | GTT | TGT | GAG | CGC | TGT | TAA | TTT | CGA |
| Val | Leu | Pro | Thr | Thr | Ser | Leu | Val | Leu | Gly | Lys | Asn | Gln | Thr | Leu | Ala | Thr | Ile | Lys | Ala> |

1260

| AAG | GAA | AAC | CAA | TTA | AGT | CAA | ATA | CTT | GCA | CCT | AAT | AAT | TAT | TAT | CCT | TCT | AAA | AAC | TTG |
| TTC | CTT | TTG | GTT | AAT | TCA | GTT | TAT | GAA | CGT | GGA | TTA | TTA | ATA | ATA | GGA | AGA | TTT | TTG | AAC |
| Lys | Glu | Asn | Gln | Leu | Ser | Gln | Ile | Leu | Ala | Pro | Asn | Asn | Tyr | Tyr | Pro | Ser | Lys | Asn | Leu> |

Sequence Range: 1 to 2220
Nucleic acid sequences = (SEQ ID NO: 30); Amino acid sequence = (SEQ ID NO: 31)

```
                                                                                                        1320
GCG CCA ATC GCA TTA AAT GCA CAA GAC GAT TTC AGT TCT ACT CCA ATT ACA ATG AAT TAC
CGC GGT TAG CGT AAT TTA CGT GTT CTG CTA AAG TCA ACA TGA GGT TAA TGT TAC TTA ATG
Ala Pro Ile Ala Leu Asn Ala Gln Asp Asp Phe Ser Ser Thr Pro Ile Thr Met Asn Tyr>
                                                                                                        1440
GGG AAT ATA GCA ACA TAC AAT TTT GAA AAT GGA AGA GTG AGG GTG GAT ACA GGC TCG AAC
CCC TTA TAT CGT TGT ATG TTA AAA CTT TTA CCT TCT CAC TCC CAC CTA TGT CCG AGC TTG
Gly Asn Ile Ala Thr Tyr Asn Phe Glu Asn Gly Arg Val Arg Val Asp Thr Gly Ser Asn
                                                                                                        1500
TGG AGT GAA GTG TTA CCG CAA ATT CAA GAA ACA ACT GCA CGT ATC ATT TTT AAT GGA AAA
ACC TCA CTT CAC AAT GGC GTT TAA GTT CTT TGT TGA CGT GCA TAG TAA AAA TTA CCT TTT
Trp Ser Glu Val Leu Pro Gln Ile Gln Glu Thr Thr ALa Arg Ile Ile Phe Asn Gly Lys
                                                                                                        1560
GAT TTA AAT CTG GTA GAA AGG CGG ATA GCG GCG GTT AAT CCT AGT GAT CCA TTA GAA ACG
CTA AAT TTA GAC CAT CTT TCC GCC TAT CGC CGC CAA TTA GGA TCA CTA GGT AAT CTT TGC
Asp Leu Asn Leu Val Glu Arg Arg Ile Ala Ala Val Asn Pro Ser Asp Pro Leu Glu Thr
                                                                                                        1620
ACT AAA CCG GAT ATG ACA TTA AAA GAA GCC CTT AAA ATA GCA TTT GGA TTT AAC GAA CCG
TGA TTT GGC CTA TAC TGT AAT TTT CTT CGG GAA TTT TAT CGT AAA CCT AAA TTG CTT GGC
Thr Lys Pro Asp Met Thr Leu Lys Glu Ala Leu Lys Ile Ala Phe Gly Phe Asn Glu Pro
                                                                                                        1680
AAT GGA AAC TTA CAA TAT CAA GGG AAA GAC ATA ACC GAA TTT GAT TTT AAT TTC GAT CAA
TTA CCT TTG AAT GTT ATA GTT CCC TTT CTG TAT TGG CTT AAA CTA AAA TTA AAG CTA GTT
Asn Gly Asn Leu Gln Tyr Gln Gly Lys Asp Ile Thr Glu Phe Asp Phe Asn Phe Asp Gln
                                                                                                        1740
CAA ACA TCT CAA AAT ATC AAG AAT CAG TTA GCG GAA TTA AAC GCA ACT AAC ATA TAT ACT
GTT TGT AGA GTT TTA TAG TTC TTA GTC AAT CGC CTT AAT TTG CGT TGA TTG TAT ATA TGA
Gln Thr Ser Gln Asn Ile Lys Asn Gln Leu Ala Glu Leu Asn Ala Thr Asn Ile Tyr Thr
                                                                                                        1800
GTA TTA GAT AAA ATC AAA TTA AAT GCA AAA ATG AAT ATT TTA ATA AGA GAT AAA CGT TTT
CAT AAT CTA TTT TAG TTT AAT TTA CGT TTT TAC TTA TAA AAT TAT TCT CTA TTT GCA AAA
Val Leu Asp Lys Ile Lys Leu Asn Ala Lys Met Asn Ile Leu Ile Arg Asp Lys Arg Phe
                                                                                                        1860
CAT TAT GAT AGA AAT AAC ATA GCA GTT GGG GCG GAT GAG TCA GTA GTT AAG GAG GCT CAT
GTA ATA CTA TCT TTA TTG TAT CGT CAA CCC CGC CTA CTC AGT CAT CAA TTC CTC CGA GTA
His Tyr Asp Arg Asn Asn Ile Ala Val Gly Ala Asp Glu Ser Val Val Lys Glu Ala His
                                                                                                        1920
AGA GAA GTA ATT AAT TCG TCA ACA GAG GGA TTA TTG TTA AAT ATT GAT AAG GAT ATA AGA
TCT CTT CAT TAA TTA AGC AGT TGT CTC CCT AAT AAC AAT TTA TAA CTA TTC CTA TAT TCT
Arg Glu Val Ile Asn Ser Ser Thr Glu Gly Leu Leu Leu Asn Ile Asp Lys Asp Ile Arg
                                                                                                        1980
AAA ATA TTA TCA GGT TAT ATT GTA GAA ATT GAA GAT ACT GAA GGG CTT AAA GAA GTT ATA
TTT TAT AAT AGT CCA ATA TAA CAT CTT TAA CTT CTA TGA CTR CCC GAA TTT CTT CAA TAT
Lys Ile Leu Ser Gly Tyr Ile Val Glu Ile Glu Asp Thr Glu Gly Leu Lys Glu Val Ile
                                                                                                        2040
AAT GAC AGA TAT GAT ATG TTG AAT ATT TCT AGT TTA CGG CAA GAT GGA AAA ACA TTT ATA
TTA CTG TCT ATA CTA TAC AAC TTA TAA AGA TCA AAT GCC CTT CTA CCT TTT TGT AAA TAT
Asn Asp Arg Tyr Asp Met Leu Asn Ile Ser Ser Leu Arg Gln Asp Gly Lys Thr Phe Ile
                                                                                                        2100
GAT TTT AAA AAA TAT AAT GAT AAA TTA CCG TTA TAT ATA AGT AAT CCC AAT TAT AAG GTA
CTA AAA TTT TTT ATA TTA CTA TTT AAT GGC AAT ATA TAT TCA TTA GGG TTA ATA TTC CAT
Asp Phe Lys Lys Tyr Asn Asp Lys Leu Pro Leu Tyr Ile Ser Asn Pro Asn Tyr Lys Val
                                                                                                        2160
AAT GTA TAT GCT GTT ACT AAA GAA AAC ACT ATT ATT AAT CCT AGT GAG AAT GGG GAT ACT
TTA CAT ATA CGA CAA TGA TTT CTT TTG TGA TAA TAA TTA GGA TCA CTC TTA CCC CTA TGA
Asn Val Tyr Ala Val Thr Lys Glu Asn Thr Ile Ile Asn Pro Ser Glu Asn Gly Asp Thr
                                                                                                        2220
AGT ACC AAC GGG ATC AAG AAA ATT TTA ATC TTT TCT AAA AAA GGC TAT GAG ATA GGA TAA
TCA TGG TTG CCC TAG TTC TTT TAA AAT TAG AAA AGA TTT TTT CCG ATA CTC TAT CCT ATT
Ser Thr Asn Gly Ile Lys Lys Ile Leu Ile Phe Ser Lys Lys Gly Tyr Glu Ile Gly***
```

The above procedure was followed for PAHIV#1, 3 and 4.

EXAMPLE 7

Cleavage of Mutant PAHIV Proteins in vitro

The mutated proteins were treated with purified HIV-1 protease and evaluated for their degree of cleavage with respect to time. The purified protease was obtained from the NIH AIDS Research and Reference Reagent Program, Division of AIDS, NIAID, Bethesda, Md. Alternatively, the protease can be purified following the method of Louis, et al., *Euro. J. Biochem.*, 199:361 (1991).

Extended incubation (12 hours) of PA or the mutated PA proteins with the purified HIV-1 protease resulted in the appearance of two additional protein fragments that were not anticipated. These two fragments are approximately 53 kilodaltons and 30 kilodaltons in size. This may represent cleavage of PA and mutant PA proteins at a site recognized by the HIV-1 protease between PA residues $y^{259}$ and $p^{260}$. The residues around this cleavage site, $^{256}VAAYPIVHV^{264}$ (SEQ. ID NO: 35), have not previously been identified as a potential HIV-1 protease cleavage site.

Incubation of RAW 264.7 cells (ATCC No. TIB 71) with lethal factor (LF) and HIV-1 protease-cleaved PAHIV#1 or PAHIV#4 caused cell death, demonstrating that the mutated PA proteins are capable of binding to LF and thus the toxic LF/PE fusion proteins. PAHIV, PAHIV#2 and PAHIV#3 have not yet been tested.

EXAMPLE 8

Evaluation of Cytotoxic Agents in Cell Cultures

The ability of the PA constructs containing the HIV-1-protease cleavage site to promote killing of HIV-1 infected cells is being evaluated in COS-1 cells (ATCC No. CRL 1650) transfected with the vector HIV-gpt. When COS cells are transfected with this plasmid vector they express all the genes for the production of HIV-1 virus particles except the envelope protein, gp160 (Page, K. A., et al., 1990. *J. Virol.* 64:5270–5276). Without the envelope protein the particles are not infectious. These cells express the HIV-1 proteases and properly cleave the viral protein gp55 to gp24 (Page, K. A., et al., 1990. *J. Virol.* 64:5270–5276). These properties make the transfected cells an excellent model system in which to evaluate the ability of protein constructs of the invention to eliminate HIV-1 infected cells from culture.

The COS-1 cells were transfected with the plasmid vector and the resulting cultures are being selected for stable transfectents. The mutated PA proteins (PAHIV#1, PAHIV#2, PAHIV#3 and PAHIV#4) are added to the culture media of growing HIV-gpt transfected COS-1 cells in the presence of the lethal factor fusion protein FP53 (Arora, N. et al. *J. Biol. Chem.* 267:15542 (1992)). Only cells which properly cleave the mutated PA proteins are able to bind the toxin LF fusion protein. The cultures are evaluated for protein expression (an indirect measure of viability) after 36 hours (Arora, N. and S. H. Leppla. 1992. *J. Biol. Chem.* 268:3334).

EXAMPLE 9

Treatment of an HIV-1 infected patient

A human patient who is infected with HIV-1 is selected for treatment. Although infected, this particular patient is asymptomatic. The patient weighs 70 kilograms. A dose of 10 micrograms per kilogram or 700 micrograms of a PAHIV in normal saline is prepared. This dosage is injected into the patient intravenously as a bolus. The dose is repeated weekly for a total of 4 to 6 dosages. The patient is evaluated regularly, such as weekly, in terms of his symptoms, physical exam and laboratory analysis according to the clinician's judgment. Tests of particular interest include the patient's complete blood count and examination for the presence of HIV infection. The treatment regimen can be repeated with or without alterations at the discretion of the clinician.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

It is understood that the examples and embodiments described herein are for illustrative purposes only and that various modifications or changes in light thereof will be suggested to persons skilled in the art and are to be included within the spirit and purview of this application and scope of the appended claims.

---

We claim:

1. A method for targeting compounds having a desired biological activity not present on native anthrax lethal factor (LF) to a specific cell population, comprising:
   a) administering to the cell population a first compound comprising a first protein consisting essentially of:
      i) the translocation domain and the anthrax lethal factor (LF) binding domain of the native anthrax protective antigen (PA) protein, and
      ii) a ligand domain that specifically binds the first protein to a target on the surface of the cell population to bind the first compound to said surface; and
   b) administering to the resultant cell population a second compound comprising a fusion protein or conjugate consisting essentially of:
      i) the anthrax protective antigen (PA) binding domain of the native anthrax lethal factor (LF) protein, chemically attached to
      ii) a biological activity-inducing polypeptide to bind the second compound to the first compound on the surface of the cell population, internalize the second compound into the cell population, and effect the activity of the polypeptide therein.

2. A method according to claim 1, wherein the anthrax protective antigen (PA) binding domain of said second compound comprises at least the first 254 amino acid residues but less than all of the amino acid residues of the anthrax lethal factor (SEQ. ID NO: 2).

3. A method according to claim 1, wherein the ligand domain of said first compound is the ligand domain of the native anthrax protective antigen (PA) protein.

4. A method according to claim 1, wherein said second compound comprises the anthrax protective antigen (PA) binding domain of the native anthrax lethal factor (LF) protein chemically attached to a polypeptide through a peptide bond.

5. The method of claim 1, wherein the polypeptide of said second compound is a toxin.

6. The method of claim 1, wherein the polypeptide of said second compound is an enzyme.

7. The method of claim 1, wherein the ligand domain of said first compound is an antibody.

8. The method of claim 1, wherein the ligand domain of said first compound is a growth factor.

9. The method of claim 5, wherein the polypeptide of said second compound is Pseudomonas exotoxin A (PE).

10. The method of claim 5, wherein the polypeptide of said second compound is the A chain of Diptheria toxin.

11. The method of claim 5, wherein the polypeptide of said second compound is shiga toxin.

12. The method of claim 7, wherein the ligand domain of said first compound is a single chain antibody.

* * * * *

UNITED STATES PATENT AND TRADEMARK OFFICE
CERTIFICATE OF CORRECTION

PATENT NO. : 5,677,274
DATED : October 14, 1997
INVENTOR(S) : Stephen H. Leppla, et al It is certified that error appears in the above-identified patent and that said Letters Patent is hereby corrected as shown below:

Title page, item [75] Inventors; please delete --Peter J. Nichols--.

Signed and Sealed this

Seventh Day of April, 1998

Attest:

BRUCE LEHMAN

*Attesting Officer*   *Commissioner of Patents and Trademarks*